United States Patent
Itoh et al.

(10) Patent No.: US 6,329,399 B1
(45) Date of Patent: Dec. 11, 2001

(54) ANTIFUNGAL AMINE DERIVATIVES AND PROCESSING FOR PRODUCING THE SAME

(75) Inventors: Takao Itoh; Takuji Nakashima; Akira Nozawa; Kouji Yokoyama; Hiroyuki Takimoto; Masayuki Yuasa; Yukio Kawazu; Toshimitsu Suzuki; Toshiro Majima, all of Kanagawa (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

(21) Appl. No.: 09/485,309

(22) PCT Filed: Aug. 5, 1998

(86) PCT No.: PCT/JP98/03487

§ 371 Date: May 18, 2000

§ 102(e) Date: May 18, 2000

(87) PCT Pub. No.: WO99/07666

PCT Pub. Date: Feb. 18, 1999

(30) Foreign Application Priority Data

Aug. 5, 1997 (JP) .................................... 9-223087
Apr. 6, 1998 (JP) .................................... 10-93567

(51) Int. Cl.[7] ...................... A61K 31/445; A61K 31/278; C07C 211/26; C07C 209/60
(52) U.S. Cl. .......................... 514/331; 514/319; 514/579; 514/647; 514/649; 514/650; 514/657; 546/205; 546/229; 546/235; 546/237; 564/316; 564/321; 564/347; 558/411; 558/415
(58) Field of Search .................. 514/579, 647, 514/649, 650, 657, 319, 331; 546/205, 229, 235, 237; 558/411, 415; 564/316, 321, 347

(56) References Cited

U.S. PATENT DOCUMENTS 3,966,814 * 6/1976 Schromm et al. ............ 564/361
5,296,612 * 3/1994 Nakagawa et al. ........... 549/49
6,015,925 * 1/2000 Kawazu et al. .............. 546/216

FOREIGN PATENT DOCUMENTS

| 1501436 | * 4/1975 | (GB) . |
| 2-502465 | 8/1990 | (JP) . |
| 4-213308 | 8/1992 | (JP) . |
| 5-92910 | 4/1993 | (JP) . |
| 5-124929 | 5/1993 | (JP) . |
| 6-116287 | 4/1994 | (JP) . |
| 8-176085 | 7/1996 | (JP) . |
| 8-311004 | 11/1996 | (JP) . |
| WO 88/07062 | 9/1888 | (WO) . |
| 91/09594 | * 7/1991 | (WO) . |

OTHER PUBLICATIONS

Stutz et al. "Synthesis and structure=activity relationships of naftifine related allylamine antimycotics" J. Med. chem. v. 29, p. 112–125 (1986).*

* cited by examiner

*Primary Examiner*—Ceila Chang
(74) *Attorney, Agent, or Firm*—Knobbe, Martens, Olson & Bear, LLP

(57) ABSTRACT

Novel amine derivatives having an excellent antimycotic effect represented by general formula (1) below and salts thereof are provided.

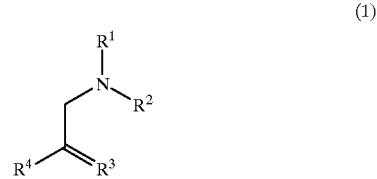

[in the formula (1, $R^1$ represents a $C_{1-5}$ alkyl group which may be halogenated, $R^2$ represents 4-(1,1-dimethylalkyl)benzyl group, 4-(1-methyl-phenylethyl)benzyl group, 1-or 2-naphthylmethyl group, or a hydrocarbon group having 3,3-dimethyl-1-butynyl group or a phenyl group at its terminal and 1 to 3 double bonds; $R^3$ represents oxygen atom or a methylene group which may be substituted by a $C_{1-4}$ alkyl group; and $R^4$ represents 1-or 2 naphthyl group or a phenyl group which may be substituted.

13 Claims, No Drawings

ANTIFUNGAL AMINE DERIVATIVES AND PROCESSING FOR PRODUCING THE SAME

This is a 35 U.S.C. §371 application of PCT/JP98/03487, filed Aug. 5, 1998, which claims priority based on Japanese Patent Applications No. 9-223087, filed Aug. 5, 1997, and No. 10-93567, filed Apr. 6, 1998.

TECHNICAL FIELD

The present invention relates to novel amine derivatives having an excellent antimycotic effect and to a method for producing the same.

BACKGROUND ART

An increasing number of patients are suffering from superficial mycosis, whose representative example is athlete's foot (tinea pedis), due to a prolonged time in which shoes are put on. However, no certain therapeutical method or remedy therefor has been found and currently it is enumerated as one of diseases that remain to be overcome. So far, great effort has been made to find their remedy and many compounds have been subjected to screening for their antimycotic effect. Although, some substances show antimycotic activity in vitro or vivo using animals, most of them do not show the antimycotic activity in real clinical tests, resulting in stopping the development of the remedy. Therefore, only a limited number of substances showed satisfactory antimycotic results.

DISCLOSURE OF THE INVENTION

An object of the present invention is to provide novel compounds having an excellent antimycotic effect and a pharmaceutical composition containing them.

Under the circumstances, the present inventors have made intensive investigation, and as a result of which, the present inventors have found that the amine derivatives represented by general formula (1) set forth below have an excellent antimycotic effect, thus completing the present invention.

That is, the present invention provides amine derivatives represented by general formula (1) below or salts thereof:

[in the formula (1) above, $R^1$ represents a linear $C_{1-5}$ alkyl group, a branched $C_{1-5}$ alkyl group, or a cyclic $C_{1-5}$ alkyl group, said $C_{1-5}$ alkyl group may be halogenated;
$R^2$ represents a group represented by the formula (a), (b), (c), (d), or (e)

("⁓") indicates that the arrangement of double bond may be either cis or trans) (provided that $R^5$ in the formula (a) is a linear $C_{1-4}$ alkyl group or a phenyl group and n in the formula (d) or (e) is an integer of 1 to 3);
$R^3$ is an oxygen atom or a group represented by the formula (f) below;

$R^6$ and $R^7$ independently represent a hydrogen atom, a linear $C_{1-4}$ alkyl group, a branched $C_{1-4}$ alkyl group or a cyclic $C_{1-4}$ alkyl group; $R^4$ represents a group represented by the formula (g), (h), or (i), in the formula (i), $R^8$ is a substituent group which substitutes a hydrogen atom in the phenyl group in the formula and represents a linear $C_{1-7}$ alkyl group, a branched $C_{1-7}$ alkyl group, a cyclic $C_{1-7}$ alkyl group, a halogen atom, a linear $C_{1-4}$ alkoxy group, a branched $C_{1-4}$ alkoxy group, a cyclic $C_{1-4}$ alkoxy group, a nitro group, an amino group may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO$—; and $R^9$ represents a linear $C_{1-4}$ alkyl group, a branched $C_{1-4}$ alkyl group or a cyclic $C_{1-4}$ alkyl group, in which three of $R^9$ may be the same or different; and m of $R^8$ may be the same or different; m is an integer of 0 to 5.].

The amine derivatives or salts thereof of the present invention specifically include: amine derivatives represented by the general formula (1) in which $R^1$ is a linear $C_{1-5}$ alkyl group, a branched $C_{1-5}$ alkyl group or a cyclic $C_{1-5}$ alkyl group; $R^2$ is a group represented by the formula (d) or (e); $R^4$ is a group represented by the formula (i); and $R^3$, $R^8$ in the formula (i), m, and n in the formula (d) or (e) are as defined above (hereinafter, referred to as "the first amine derivatives of the invention") or salts thereof; or amine derivatives represented by the general formula (1) in which $R^1$ is a linear $C_{1-4}$ alkyl group, a branched $C_{1-4}$ alkyl group or a cyclic $C_{1-4}$ alkyl group, said $C_{1-4}$ alkyl group may be halogenated, $R^2$ is a group represented by the formula (a), (b) or (c); $R^8$, when $R^4$ is represented by the formula (i), is a linear $C_{1-4}$ alkyl group, a branched $C_{1-4}$ alkyl group, a cyclic $C_{1-4}$ alkyl group, a halogen atom, a liner $C_{1-4}$ alkoxy group, a branched $C_{1-4}$ alkoxy group, a cyclic $C_{1-4}$ alkoxy group, a nitro group, an amino group may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO$—, $R^9$ represents a linear $C_{1-4}$ alkyl group, a branched $C_{1-4}$ alkyl group or a cyclic $C_{1-4}$ alkyl group, in which three of $R^9$ may be the same or different, m is an integer of 0 to 5, m of $R^8$ may be the same or different; $R^3$, and $R^5$ in the formula (a) are as defined above (hereinafter, referred to as "the second amine derivatives of the invention")

Further, the present invention provides a method for producing amine derivatives represented by general formula (1) or salts thereof.

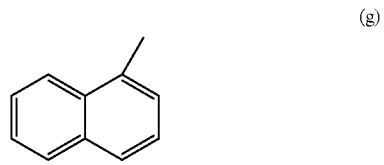

(1)

(in the formula (1), $R^1$, $R^2$, $R^3$, and $R^4$ represent the same meanings as those in formulae (2) and (3) below] comprising condensing a compound represented by general formula (2)

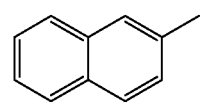

(2)

[in the formula (2), $R^1$ represents a linear $C_{1-5}$ alkyl group, a branched $C_{1-5}$ alkyl group, or a cyclic $C_{1-5}$ alkyl group, said $C_{1-5}$ alkyl group may be halogenated; $R^3$ represents an oxygen atom or a group represented by the formula (f) below;

(f)

$R^6$ and $R^7$ independently represent a hydrogen atom or a linear $C_{1-4}$ alkyl group, a branched $C_{1-4}$ alkyl group or a cyclic $C_{1-4}$ alkyl group; $R^4$ represents a group represented by the formula (g), (h), or (i), (g)

(h)

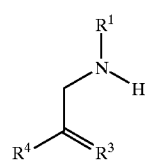

(i)

in the formula (i), $R^8$ is a substituent group which substitutes a hydrogen atom in the phenyl group in the formula and represents a linear $C_{1-7}$ alkyl group, a branched $C_{1-7}$ alkyl group, a cyclic $C_{1-7}$ alkyl group, a halogen atom, a liner $C_{1-4}$ alkoxy group, a branched $C_{1-4}$ alkoxy group, a cyclic $C_{1-4}$ alkoxy group, a nitro group, an amino group may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO$—, $R^9$ represents a linear $C_{1-4}$ alkyl group, a branched $C_{1-4}$ alkyl group or cyclic $C_{1-4}$ alkyl group, in which three of $R^9$ may be the same or different; and m of $R^8$ may be the same or different; m is an integer of 0 to 5.] with a compound represented by general formula (3)

(3)

[in the formula (3), $R^2$ represents a group represented by the formula (a), (b), (c), (d), or (e)

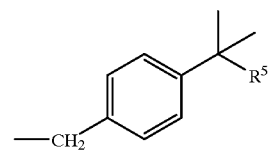

(a)

-continued

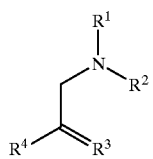
(b)

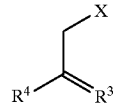
(c)

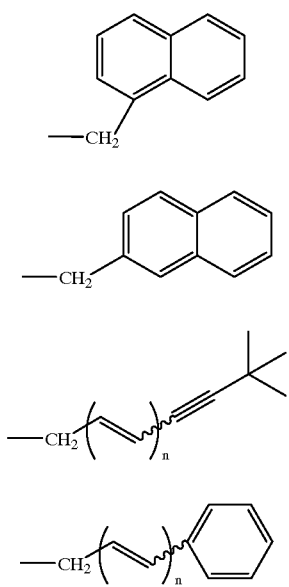
(d)

(e)

("〜〜") indicates that the arrangement of double bond may be either cis or trans) (provided that $R^5$ in the formula (a) is a linear $C_{1-4}$ alkyl group or a phenyl group and n in the formula (d) or (e) is an integer of 1 to 3); and X represents a halogen atom].

Still further, the present invention provides a method for producing amine derivatives represented by general formula (1) or salts thereof

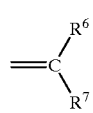
(1)

[in the formula (1), $R^1$, $R^2$, $R^3$, and $R^4$ represent the same meanings as those in formulae (4) and (5)] comprising condensing a compound represented by general formula (4)

(4)

[in the formula (4), $R^3$ represents an oxygen atom or a group represented by the formula (f) below;

(f)

$R^6$ and $R^7$ independently represent a hydrogen atom, a linear $C_{1-4}$ alkyl group, a branched $C_{1-4}$ alkyl group or a cyclic $C_{1-4}$ alkyl group, $R^4$ is a group represented by the formula (g), (h), or (i),

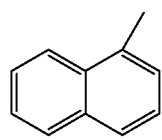
(g)

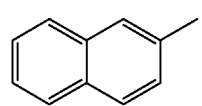
(h)

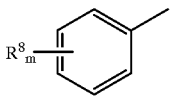
(i)

in the formula (i), $R^8$ is a substituent group which substitutes a hydrogen atom in the phenyl group in the formula and represents a linear $C_{1-7}$ alkyl group, a branched $C_{1-7}$ alkyl group, a cyclic $C_{1-7}$ alkyl group, a halogen atom, a linear $C_{1-4}$ alkoxy group, a branched $C_{1-4}$ alkoxy group, a cyclic $C_{1-4}$ alkoxy group, a nitro group, an amino group which may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO—$, $R^9$ represents a linear $C_{1-4}$ alkyl group, a branched $C_{1-4}$ alkyl group or a cyclic $C_{1-4}$ alkyl group, in which three of $R^9$ may be the same or different; m of $R^8$ may be the same or different; m is an integer of 0 to 5; and X represents a halogen atom.]
with a compound represented by general formula (5)

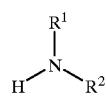
(5)

[in the formula (5), $R^1$ represents a linear $C_{1-5}$ alkyl group, a branched $C_{1-5}$ alkyl group, or a cyclic $C_{1-5}$ alkyl group, said $C_{1-5}$ alkyl group may be halogenated; $R^2$ represents a group represented by the formula (a), (b), (c), (d), or (e)

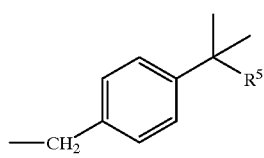
(a)

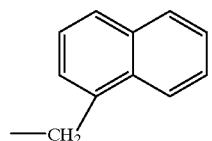
(b)

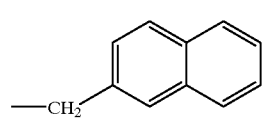
(c)

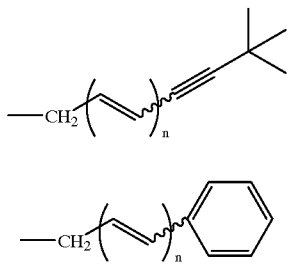

("~~~") indicates that the arrangement of double bond may be either cis or trans) (provided that $R^5$ in the formula (a) is a linear $C_{1-4}$ alkyl group or a phenyl group and n in the formula (d) or (e) is an integer of 1 to 3)].

The present invention provides an antimycotic agent comprising the amine derivatives or salts thereof.

The present invention provides an antimycotic composition comprising the amine derivatives or salts thereof.

The present invention provides a pharmaceutical composition comprising, as an active ingredient, the amine derivatives or salts thereof.

BEST MODE FOR CARRYING OUT THE INVENTION

Hereinafter, the present invention will be described in detail. First, the amine derivatives of the present invention and salts thereof will be explained.

(1) Amine Derivatives of the Present Invention and Salts thereof

The amine derivatives of the present invention are compounds represented by the general formula (1) above. $R^1$, $R^2$, $R^3$, and $R^4$ in the formula (1) can be selected without restriction from the atoms or groups within the above-described ranges. The amine derivatives of the present invention specifically include the first amine derivatives of the invention and the second amine derivatives of the invention described above. Hereinafter, more detailed description will be made on the first amine derivatives of the invention and the second amine derivatives of the invention.

(i) The First Amine Derivatives of the Present Invention

The first amine derivatives of the invention are compounds represented by the general formula (1) above in which $R^1$, $R^2$, $R^3$, and $R^4$ are selected from the atoms or groups set forth below.

$R^1$ represents a linear $C_{1-5}$ alkyl group, a branched $C_{1-5}$ alkyl group, or a cyclic $C_{1-5}$ alkyl group and specific examples thereof include a methyl group, an ethyl group, an n-propyl group, an i-propyl group, a cyclopropyl group, an n-butyl group, an i-butyl group, a sec-butyl group, a tert-butyl group, a cyclobutyl group, etc. Among these, a $C_{1-3}$ alkyl group are preferred, in particular, a methyl group, an ethyl group, an i-propyl group, or a cyclopropyl group.

$R^2$ is a group represented by the formula (d) or (e) above, n in the formula (d) or (e) is an integer of 1 to 3, and preferably n is 1. Of the groups represented by the formulae (d) and (e), the group represented by the formula (d) is more preferred.

$R^3$ is an oxygen atom or a group represented by the formula (f). In the formula (f), $R^6$ and $R^7$ independently represent a hydrogen atom, or a linear $C_{1-4}$ alkyl group, a branched $C_{1-4}$ alkyl group, or a cyclic $C_{1-4}$ alkyl group. Specific examples of $R^3$ include, preferably, a carbon atom to which an oxygen atom and two hydrogen atoms are added, a carbon atom to which a hydrogen atom and a methyl group are added, and a carbon atom to which two methyl groups are added. Of these, a carbon atom to which an oxygen atom and two hydrogen atoms are added is particularly preferred.

$R^4$ is a group represented by the formula (i). In the formula (i), $R^8$ is a substituent group which substitutes for hydrogen atom(s) of the phenyl group in the formula (i) and represents a linear $C_{1-7}$ alkyl group, a branched $C_{1-7}$ alkyl group, a cyclic $C_{1-7}$ alkyl group, a halogen atom, a linear $C_{1-4}$ alkoxy group, a branched $C_{1-4}$ alkoxy group, a cyclic $C_{1-4}$ alkoxy group, a nitro group, an amino group which may have a substituent group, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO-$. $R^9$ represents a $C_{1-4}$ alkyl group, a branched $C_{1-4}$ alkyl group or a cyclic $C_{1-4}$ alkyl group, in which three of $R^9$ may be the same or different; m is 0 or an integer of 1–5; and m of $R^8$ may be the same or different. In the present specification, the number of carbons in "$C_{2-5}$ alkoxycarbonyl group" is counted as including that of carbonyl group part.

More specifically, preferred examples of $R^8$ include a methyl group, a tert-butyl group, a fluorine atom, a chlorine atom, a bromine atom, a methoxy group, a nitro group, an amino group, a cyano group, an ethoxycarbonyl group, a hydroxyl group, a tert-butyldimethylsilyl group, and so forth.

Preferred specific examples of the first amine derivatives of the invention as described above include the following compounds:

Trans-2-[N-(6,6-dimethyl-2-hepten-4-ynyl)-N-methylamino]acetophenone (hereinafter, sometimes referred to as "Compound PR-1130". Similarly, abbreviation will be described after the name of substance.);

Trans-N-(6,6-dimethyl-2-hepten-4-ynyl)-N-methyl-2-phenyl-2-propenylamine (Compound PR-1257);

Trans-2-[N-(6,6-dimethyl-2-hepten-4-ynyl)-N-methylamino]-2'-methylacetophenone (Compound PR-1531);

Trans-N-(6,6-dimethyl-2-hepten-4-ynyl)-N-methyl-[2-(o-tolyl)-2-propenyl]amine ("Compound PR-1532");

Trans-2-[N-(6,6-dimethyl-2-hepten-4-ynyl)-N-methylamino]-3'-methylacetophenone (Compound PR-1538);

Trans-N-(6,6-dimethyl-2-hepten-4-ynyl)-N-methyl-[2-(m-tolyl)-2-propenyl]amine (Compound PR-1539);

Trans-2-[N-(6,6-dimethyl-2-hepten-4-ynyl)-N-methylamino]-4'-methylacetophenone (Compound PR-1413);

Trans-N-(6,6-dimethyl-2-hepten-4-ynyl)-N-methyl-[2-(p-tolyl)-2-propenyl]amine (Compound PR-1414);

Trans-2-[N-(6,6-dimethyl-2-hepten-4-ynyl)-N-methylamino]-2'-fluoroacetophenone (Compound PR-1489);

Trans-N-(6,6-dimethyl-2-hepten-4-ynyl)-N-methyl-[2-(2-fluorophenyl)-2-propenyl]amine (Compound PR-1490);

Trans-2-[N-(6,6-dimethyl-2-hepten-4-ynyl)-N-methylamino]-3'-fluoroacetophenone (Compound PR-1468);

Trans-N-(6,6-dimethyl-2-hepten-4-ynyl)-N-methyl-[2-(3-fluorophenyl)-2-propenyl]amine (Compound PR-1469);

Trans-2-[N-(6,6-dimethyl-2-hepten-4-ynyl)-N-methylamino]-4'-fluoroacetophenone (Compound PR-1428);

Trans-N-(6,6-dimethyl-2-hepten-4-ynyl)-N-methyl-[2-(4-fluorophenyl)-2-propenyl]amine (Compound PR-1429);

Trans-2'-bromo-2-[N-(6,6-dimethyl-2-hepten-4-ynyl)-N-methylamino]acetophenone (Compound PR-1503);

Trans-N-(6,6-dimethyl-2-hepten-4-ynyl)-N-methyl-[2-(2-bromophenyl)-2-propenyl]amine (Compound PR-1504);

Trans-3'-bromo-2-[N-(6,6-dimethyl-2-hepten-4-ynyl)-N-methylamino]acetophenone (Compound PR-1482);

Trans-N-(6,6-dimethyl-2-hepten-4-ynyl)-N-methyl-[2-(3-bromophenyl)-2-propenyl]amine (Compound PR-1483);

Trans-4'-bromo-2-[N-(6,6-dimethyl-2-hepten-4-ynyl)-N-methylamino]acetophenone (Compound PR-1437);

Trans-N-(6,6-dimethyl-2-hepten-4-ynyl)-N-methyl-[2-(4-bromophenyl)-2-propenyl]amine (Compound PR- 1438);

Trans-2'-chloro-2-[N-(6,6-dimethyl-2-hepten-4-ynyl)-N-methylamino]acetophenone (Compound PR-1496);

Trans-N-(6,6-dimethyl-2-hepten-4-ynyl)-N-methyl-[2-(2-chlorophenyl)-2-propenyl]amine (Compound PR-1497);

Trans-4'-chloro-2-[N-(6,6-dimethyl-2-hepten-4-ynyl)-N-methylamino]acetophenone (Compound PR-1416);

Trans-N-(6,6-dimethyl-2-hepten-4-ynyl)-N-methyl-[2-(4-chlorophenyl)-2-propenyl]amine (Compound PR-1417);

Trans-2-[N-(6,6-dimethyl-2-hepten-4-ynyl)-N-methylamino]-2'-methoxyacetophenone (Compound PR-1632);

Trans-N-(6,6-dimethyl-2-hepten-4-ynyl)-N-methyl-[2-(2-methoxyphenyl)-2-propenyl]amine (Compound PR-1633);

Trans-2-[N-(6,6-dimethyl-2-hepten-4-ynyl)-N-methylamino]-3'-methoxyacetophenone (Compound PR-1388);

Trans-N-(6,6-dimethyl-2-hepten-4-ynyl)-N-methyl-[2-(3-methoxyphenyl)-2-propenyl]amine (Compound PR-1389);

Trans-2-[N-(6,6-dimethyl-2-hepten-4-ynyl)-N-methylamino]-2'-nitroacetophenone (Compound PR-1639);

Trans-N-(6,6-dimethyl-2-hepten-4-ynyl)-N-methyl-[2-(2-nitrophenyl)-2-propenyl]amine (Compound PR-1640);

Trans-2-[N-(6,6-dimethyl-2-hepten-4-ynyl)-N-methylamino]-3'-nitroacetophenone (Compound PR-1646);

Trans-N-(6,6-dimethyl-2-hepten-4-ynyl)-N-methyl-[2-(3-nitrophenyl)-2-propenyl]amine (Compound PR-1647);

Trans-2-[N-(6,6-dimethyl-2-hepten-4-ynyl)-N-methylamino]-4'-nitroacetophenone (Compound PR-1393);

Trans-N-(6,6-dimethyl-2-hepten-4-ynyl)-N-methyl-[2-(4-nitrophenyl)-2-propenyl]amine (Compound PR-1394);

Trans-3'-cyano-2-[N-(6,6-dimethyl-2-hepten-4-ynyl)-N-methylamino]acetophenone (Compound PR-1552);

Trans-3-{1-[N-(6,6-dimethyl-2-hepten-4-ynyl)-N-methylamino]methyl}vinylbenzonitrile (Compound PR-1553);

Trans-4'-cyano-2-[N-(6,6-dimethyl-2-hepten-4-ynyl)-N-methylamino]acetophenone (Compound PR-1559);

Trans-4-{1-[N-(6,6-dimethyl-2-hepten-4-thylamino]methyl}vinylbenzonitrile (Compound PR-1560);

Ethyl trans-4-{2-[N-(6,6-dimethyl-2-hepten-4-ynyl)-N-methylamino]acetyl}benzoate (Compound PR- 1685);

Ethyl trans-4-{1-[N-(6,6-dimethyl-2-hepten-4-ynyl)-N-methylamino]methyl}vinylbenzoate (Compound PR-1686);

Trans-2',4'-dichloro-2-[N-(6,6-dimethyl-2-hepten-4-ynyl)-N-methylamino]acetophenone (Compound PR-1517);

Trans-N-(6,6-dimethyl-2-hepten-4-ynyl)-N-methyl-[2-(2,4-dichlorophenyl)-2-propenyl]amine (Compound PR-1518);

Trans-3',4'-dichloro-2-[N-(6,6-dimethyl-2-hepten-4-ynyl)-N-methylamino]acetophenone (Compound PR-1510);

Trans-N-(6,6-dimethyl-2-hepten-4-ynyl)-N-methyl-[2-(3,4-dichlorophenyl)-2-propenyl]amine (Compound PR-1511);

Trans-2',4'-dimethyl-2-[N-(6,6-dimethyl-2-hepten-4-ynyl)-N-methylamino]acetophenone (Compound PR-1710);

Trans-N-(6,6-dimethyl-2-hepten-4-ynyl)-N-methyl-[2-(2,4-dimethylphenyl)-2-propenyl]amine (Compound PR-1711);

Trans-3',4'-dimethyl-2-[N-(6,6-dimethyl-2-hepten-4-ynyl)-N-methylamino]acetophenone (Compound PR-1703);

Trans-N-(6,6-dimethyl-2-hepten-4-ynyl)-N-methyl-[2-(3,4-dimethylphenyl)-2-propenyl]amine (Compound PR-1704);

Trans-3',4'-difluoro-2-[N-(6,6-dimethyl-2-hepten-4-ynyl)-N-methylamino]acetophenone (Compound PR-2171);

Trans-N-(6,6-dimethyl-2-hepten-4-ynyl)-N-methyl-[2-(3,4-difluorophenyl)-2-propenyl]amine (Compound PR-2172);

Trans-3',5'-difluoro-2-[N-(6,6-dimethyl-2-hepten-4-ynyl)-N-methylamino]acetophenone (Compound PR-2157);

Trans-N-(6,6-dimethyl-2-hepten-4-ynyl)-N-methyl-[2-(3,5-difluorophenyl)-2-propenyl]amine (Compound PR-2158);

Trans-4'-tert-butyl-2-[N-(6,6-dimethyl-2-hepten-4-ynyl)-N-methylamino]acetophenone (Compound PR-1717);

Trans-N-(6,6-dimethyl-2-hepten-4-ynyl)-N-methyl-[2-(4-tert-butylphenyl)-2-propenyl]amine (Compound PR-1718);

Trans-2-[N-(6,6-dimethyl-2-hepten-4-ynyl)-N-methylamino]-2'-hydroxyacetophenone (Compound PR-1619);

Trans-4'-tert-butyldimethylsilyloxy-2-[N-(6,6-dimethyl-2-hepten-4-ynyl)-N-methylamino]acetophenone (Compound PR-1604);

Trans-N-(6,6-dimethyl-2-hepten-4-ynyl)-N-methyl-[2-(4-tert-butyldimethylsilyloxyphenyl)-2-propenyl]amine (Compound PR-1605);

Trans-N-(6,6-dimethyl-2-hepten-4-ynyl)-N-methyl-[2-(4-hydroxyphenyl)-2-propenyl]amine (Compound PR-1606);

Trans-N-(6,6-dimethyl-2-hepten-4-ynyl)-N-methyl-[2-(2-aminophenyl)-2-propenyl]amine (Compound PR-1672);

Trans-N-(6,6-dimethyl-2-hepten-4-ynyl)-N-methyl-[2-(3-aminophenyl)-2-propenyl]amine (Compound PR-1676);

N-Cinnamyl-N-methyl-2-phenyl-2-propenylamine (Compound PR-1806);

Trans-N-(6,6-dimethyl-2-hepten-4-ynyl)-N-ethyl-2-phenyl-2-propenylamine (Compound PR-1853);

Trans-N-(6,6-dimethyl-2-hepten-4-ynyl)-N-isopropyl-2-phenyl-2-propenylamine (Compound PR-1855); and Trans-N-cyclopropyl-N-(6,6-dimethyl-2-hepten-4-ynyl)-2-phenyl-2-propenylamine (Compound PR-1930).

Of these, further preferred examples include the following:

Trans-N-(6,6-dimethyl-2-hepten-4-ynyl)-N-methyl-2-phenyl-2-propenylamine (Compound PR-1257), Trans-N-(6,6-dimethyl-2-hepten-4-ynyl)-N-methyl-[2-(o-tolyl)-2-propenyl]amine ("Compound PR-1532"), Trans-N-(6,6-dimethyl-2-hepten-4-ynyl)-N-methyl-[2-(m-tolyl)-2-propenyl]amine (Compound PR-1539), Trans-N-(6,6-dimethyl-2-hepten-4-ynyl)-N-methyl-[2-(2-fluorophenyl)-2-propenyl]amine (Compound PR-1490), Trans-N-(6,6-dimethyl-2-hepten-4-ynyl)-N-methyl-[2-(4-fluorophenyl)-2-propenyl]amine (Compound PR-1429), Trans-N-(6,6-dimethyl-2-hepten-4-ynyl)-N-methyl-[2-(2-bromophenyl)-2-propenyl]amine (Compound PR-1504), Trans-N-(6,6-dimethyl-2-hepten-4-ynyl)-N-methyl-[2-(3-bromophenyl)-2-propenyl]amine (Compound PR-1483), Trans-N-(6,6-dimethyl-2-hepten-4-ynyl)-N-methyl-[2-(4-bromophenyl)-2-propenyl]amine (Compound PR-1438), Trans-N-(6,6-dimethyl-2-hepten-4-ynyl)-N-methyl-[2-(4-chorophenyl)-2-propenyl]amine (Compound PR-1417), Trans-N-(6,6-dimethyl-2-hepten-4-ynyl)-N-methyl-[2-(2-nitrophenyl)-2-propenyl]amine (Compound PR-1640), Trans-3-{1-[N-(6,6-dimethyl-2-hepten-4-ynyl)-N-methylamino]methyl}vinylbenzonitrile (Compound PR-1553), Trans-N-(6,6-dimethyl-2-hepten-4-ynyl)-N-methyl-[2-(2,4-dimethylphenyl)-2-propenyl]amine (Compound PR-1711), Trans-N-(6,6-dimethyl-2-hepten-4-ynyl)-N-methyl-[2-(3,4-dimethylphenyl)-2-propenyl]amine (Compound PR-1704), Trans-N-(6,6-dimethyl-2-hepten-4-ynyl)-N-methyl-[2-(3,4-difluorophenyl)-2-propenyl]amine (Compound PR-2172), Trans-N-(6,6-dimethyl-2-hepten-4-ynyl)-N-methyl-[2-(3,5-difluorophenyl)-2-propenyl]amine (Compound PR-2158), Trans-2-[N-(6,6-dimethyl-2-hepten-4-ynyl)-N-methylamino]-2'-hydroxyacetophenone (Compound PR-1619), Trans-N-(6,6-dimethyl-2-hepten-4-ynyl)-N-methyl-[2-(4-hydroxyphenyl)-2-propenyl]amine (Compound PR-1606), and Trans-N-(6,6-dimethyl-2-hepten-4-ynyl)-N-methyl-[2-(2-aminophenyl)-2-propenyl]amine (Compound PR-1672).

(ii) Second Amine Derivatives of the Present Invention

The second amine derivatives of the invention are compounds represented by the general formula (1) above in which $R^1$, $R^2$, $R^3$, and $R^4$ are selected from atoms or groups set forth below.

$R^1$ represents a linear $C_{1-4}$ alkyl group, a branched $C_{1-4}$ alkyl group or a cyclic $C_{1-4}$ alkyl group, said $C_{1-4}$ alkyl group which may be halogenated, and specific examples thereof include a methyl group, an ethyl group, an n-propyl group, an iso-propyl group, a cyclopropyl group, an n-butyl group, an isobuthyl group, a sec-butyl group, a tert-butyl group, a cyclobuthyl group, a trifluoromethyl group, 2,2,2-trifluoroethyl group, and so forth. Among these, a $C_{1-3}$ alkyl group are preferred, in particular, a methyl group, an ethyl group, an isopropyl group, a cyclopropyl group, or a 2,2,2-trifluoroethyl group.

$R^2$ is a group represented by the formula (a), (b), or (c) above, in particular, a group represented by the formula (a) is preferred. In the formula (a), $R^5$ is a linear chain $C_{1-4}$ alkyl group or phenyl group. Specific examples of $R^5$ include a methyl group, an ethyl group, an n-propyl group, an n-butyl group, a phenyl group, etc. of these, a methyl group, a phenyl group and so forth are preferred.

$R^3$ is an oxygen atom or a group represented by the formula (f). In the formula (f), $R^6$ and $R^7$ independently represent a hydrogen atom or a linear $C_{1-4}$ alkyl group, a branched $C_{1-4}$ alkyl group or a cyclic $C_{1-4}$ alkyl group. Specific examples of $R^3$ include, preferably, a carbon atom to which an oxygen atom and two hydrogen atoms are added, and a carbon atom to which two methyl groups are added. Of these, a carbon atom to which an oxygen atom and two hydrogen atoms are added is particularly preferred.

$R^4$ is a group represented by the formula (g), (h) or (i). In the formula (i), $R^8$ is a substituent group which substitutes for hydrogen atom(s) in the phenyl group in the formula and represents a linear $C_{1-4}$ alkyl group, a branched $C_{1-4}$ alkyl group, a cyclic $C_{1-4}$ alkyl group, a halogen atom, a linear $C_{1-4}$ alkoxy group, a branched $C_{1-4}$ alkoxy group, a cyclic $C_{1-4}$ alkoxy group, a nitro group, an amino group which may be substuted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO$—. $R^9$ represents a linear $C_{1-4}$ alkyl group, a branched $C_{1-4}$ alkyl group or a cyclic $C_{1-4}$ alkyl group, in which three of $R^9$ may be the same or different; m is an integer of 0 to 5; and m of $R^8$ may be the same or different.

Of the atoms or groups represented by $R^8$ in the formula (i), a linear $C_{1-4}$ alkyl group, a branched $C_{1-4}$ alkyl group or a cyclic $C_{1-4}$ alkyl group specifically includes a methyl group, an ethyl group, an n-propyl group, an iso-propyl group, a cyclopropyl group, an n-butyl group, a sec-butyl group, an isobutyl group, a tert-butyl group and so forth. Among these, a methyl group and a tert-butyl group are preferred.

The above-described halogen atom includes, for example, a fluorine atom, a chlorine atom, a bromine atom, an iodine atom and so forth. Among these, a fluorine atom, a chlorine atom, and a bromine atom are preferred.

Further, a linear $C_{1-4}$ alkoxy group, a branched $C_{1-4}$ alkoxy group or a cyclic $C_{1-4}$ alkoxy group includes, for example, a methoxy group, an ethoxy group, an n-propoxy group, an isopropoxy group, a cyclopropoxy group, an n-butoxy group, a sec-butoxy group, an isobutoxy group, a tert-butoxy group and so forth. Among these, a methoxy group is preferred.

The amino group which may be substituted includes, for example, an amino group, a piperidino group and so forth.

Further, examples of the above-described a linear $C_{2-5}$ alkoxycarbonyl group, a branched $C_{2-5}$ alkoxycarbonyl group or a cyclic $C_{2-5}$ alkoxycarbonyl group (the number of carbons being indicated as including that of the carbonyl group part) include a methoxycarbonyl group, an ethoxycarbonyl group, an n-propoxycarbonyl group, an isopropoxycarbonyl group, a cyclopropoxycarbonyl group, an n-butoxycarbonyl group, a sec-butoxycarbonyl group, an isobutoxycarbonyl group, a tert-butoxycarbonyl group and so forth. Among these, an ethoxycarbonyl group is preferred.

The group represented by above-described $R^9{}_3SiO$— includes, for example, a trimethylsilyloxy group, a tert-butyldimethylsilyloxy group and so forth. Among these, a tert-butyldimethylsilyloxy group is preferred.

Among the above-described atoms or groups, particularly preferred examples of $R^8$ include a fluorine atom, a chlorine atom, a bromine atom, a methyl group, a tert-butyl group, a methoxy group, a hydroxyl group, a tert-butyldimethylsilyloxy group, a nitro group, a cyano group, an amino group, a piperidino group, a carboxyl group, and an ethoxycarbonyl group.

Preferred specific examples of the second amine derivatives of the invention as described above include the following compounds:

2-[N-(4-tert-butylbenzyl)-N-methylamino]acetophenone (hereinafter, sometimes referred to as "Compound AD-001". Similarly, abbreviation will be described after the name of substance.), N-(4-tert-butylbenzyl)-N-methyl-2-phenyl-2-propenylamine (Compound AD-003);

4'-bromo-2-([N-(4-tert-butylbenzyl)-N-methylamino]acetophenone (Compound AD-005);

N-(4-tert-butylbenzyl)-N-methyl-[2-(4-bromophenyl-2-propenyl]amine (Compound AD-006);

2-[N-(4-tert-butylbenzyl)-N-methylamino]-4'-chloroacetophenone (Compound AD-008);

N-(4-tert-butylbenzyl)-N-methyl-[2-(4-chlorophenyl)-2-propenyl]amine (Compound AD-009);

2-[N-(4-tert-butylbenzyl)-N-methylamino]-4'-fluoroacetophenone (Compound AD-011);

N-(4-tert-butylbenzyl)-N-methyl-[2-(4 -fluorophenyl-2-propenyl]amine (Compound AD-012);

2-[N-(4-tert-butylbenzyl)-N-methylamino]-2'-fluoroacetophenone (Compound AD-014);

N-(4-tert-butylbenzyl)-N-methyl-[2-(2-fluorophenyl-2-propenyl]amine (Compound AD-015);

2-[N-(4-tert-butylbenzyl)-N-methylamino]-2'-bromoacetophenone (Compound AD-017);

N-(4-tert-butylbenzyl)-N-methyl-[2-(2-bromophenyl-2-propenyl]amine (Compound AD-018);

2-[N-(4-tert-butylbenzyl)-N-methylamino]-3'-bromoacetophenone (Compound AD-020);

N-(4-tert-butylbenzyl)-N-methyl-[2-(3-bromophenyl)-2-propenyl]amine (Compound AD-021);

2-[N-(4-tert-butylbenzyl)-N-methylamino]-3'-methylacetophenone (Compound AD-023);

N-(4-tert-butylbenzyl)-N-methyl-[2-(3-methylphenyl)-2-propenyl]amine (Compound AD-024);

2-[N-(4-tert-butylbenzyl)-N-methylamino]-2'-methylacetophenone (Compound AD-026);

N-(4-tert-butylbenzyl)-N-methyl-[2-(2-methylphenyl)-2-propenyl]amine (Compound AD-027);

2-[N-(4-tert-butylbenzyl)-N-methylamino]-2'-methoxyacetophenone (Compound AD-029);

N-(4-tert-butylbenzyl)-N-methyl-[2-(2-methoxyphenyl)-2-propenyl]amine (Compound AD-030);

N-(4-tert-butylbenzyl)-N-methyl-[2-(2-nitrophenyl)-2-propenyl]amine (Compound AD-032);

N-(4-tert-butylbenzyl)-N-methyl-[2-(4-nitrophenyl)-2-propenyl]amine (Compound AD-034);

N-(4-tert-butylbenzyl)-N-methyl-[2-(3-nitrophenyl)-2-propenyl]amine (Compound AD-036);

N-(4-tert-butylbenzyl)-N-methyl-[2-(3-aminophenyl)-2-propenyl]amine (Compound AD-038);

N-(4-tert-butylbenzyl)-N-methyl-[2-(2-aminophenyl)-2-propenyl]amine (Compound AD-040);

2-[N-(4-tert-butylbenzyl)-N-methylamino]-3',4'-dimethylacetophenone (Compound AD-041);

N-(4-tert-butylbenzyl)-N-methyl-[2-(3,4-dimethylphenyl)-2-propenyl]amine (Compound AD-042);

2-[N-(4-tert-butylbenzyl)-N-methylamino]-2',4'-dimethylacetophenone (Compound AD-044);

N-(4-tert-butylbenzyl)-N-methyl-[2-(2,4-dimethylphenyl)-2-propenyl]amine (Compound AD-045);

4'-tert-butyl-2-[N-(4-tert-butylbenzyl)-N-methylamino]acetophenone (Compound AD-047);

N-(4-tert-butylbenzyl)-N-methyl-[2-(4-tert-butylphenyl)-2-propenyl]amine (Compound AD-048);

2-[N-(4-tert-butylbenzyl)-N-methylamino]-3'-cyanoacetophenone (Compound AD-050);

3-[1-{N-(4-tert-butylbenzyl)-N-methylamino}methyl]vinylbenzonitrile (Compound AD-051);

2-[N-(4-tert-butylbenzyl)-N-methylamino]-4'-tert-butyldimethylsilyloxyacetophenone (Compound AD-053);

N-(4-tert-butylbenzyl)-N-methyl-[2-(4-tert-butyldimethylsilyloxyphenyl)-2-propenyl]amine (Compound AD-054);

N-(4-tert-butylbenzyl)-N-methyl-[2-(4-hydroxyphenyl)-2-propenyl]amine (Compound AD-055);

2-[N-(4-tert-butylbenzyl)-N-methylamino]-2'-hydroxyacetophenone (Compound AD-056);

N-methyl-N-(1-naphthylmethyl)-2-phenyl-2-propenylamine (Compound AD-058);

N-methyl-N-(2-naphthylmethyl)-2-phenyl-2-propenylamine (Compound AD-060);

4'-tert-butyl-2-[N-methyl-N-(2-naphthylmethyl)amino]acetophenone (Compound AD-062);

N-methyl-N-(2-naphthylmethyl)-[2-(4-tert-butylphenyl)-2-propenyl]amine (Compound AD-063);

4'-tert-butyl-2-[N-methyl-N-(1-naphthylmethyl)amino]acetophenone (Compound AD-065);

N-methyl-N-(1-naphthylmethyl)-[2-(4-tert-butylphenyl)-2-propenyl]amine (Compound AD-066);

2-[N-(4-tert-butylbenzyl)-N-methylamino]-2'-acetonaphthone (Compound AD-068);

N-(4-tert-butylbenzyl)-N-methyl-[2-(2-naphthyl)-2-propenyl]amine (Compound AD-069);

N-(4-tert-butylbenzyl)-N-(2,2,2-trifluoroethyl)-2-phenyl-2-propenylamine (Compound AD-071);

2-[N-(4-tert-butylbenzyl)-N-methylamino]-3',5'-difluoroacetophenone (Compound AD-072);

N-(4-tert-butylbenzyl)-N-methyl-[2-(3,5-difluorophenyl)-2-propenyl]amine (Compound AD-073);

2-[N-(4-tert-butylbenzyl)-N-methylamino]-3',4'-difluoroacetophenone (Compound AD-075);

N-(4-tert-butylbenzyl)-N-methyl-[2-(3,4-difluorophenyl)-2-propenyl]amine (Compound AD-076);

N-[4-(1-methyl-1-phenylethyl)benzyl]-N-methyl-2-phenyl-2-propenylamine (Compound AD-078);

2-[N-(4-tert-butylbenzyl)-N-methylamino]-4'-methylacetophenone (Compound AD-080);

N-(4-tert-butylbenzyl)-N-methyl-[2-(4-methylphenyl)-2-propenyl]amine (Compound AD-081);

2-[N-(4-tert-butylbenzyl)-N-methylamino]-3'-fluoroacetophenone (Compound AD-083);

N-(4-tert-butylbenzyl)-N-methyl-[2-(3-fluorophenyl)-2-propenyl]amine (Compound AD-084);

2-[N-(4-tert-butylbenzyl)-N-methylamino]-2',4'-dichloroacetophenone (Compound AD-086);

N-(4-tert-butylbenzyl)-N-methyl-[2-(2,4-dichlorophenyl)-2-propenyl]amine (Compound AD-087);

N-(4-tert-butylbenzyl)-N-methyl-3-methyl-2-phenyl-2-butenylamine (Compound AD-089);

2-[N-(4-tert-butylbenzyl)-N-methylamino]-2'-chloroacetophenone (Compound AD-091);

N-(4-tert-butylbenzyl)-N-methyl-[2-(2-chlorophenyl)-2-propenyl]amine (Compound AD-092);

2-[N-(4-tert-butylbenzyl)-N-methylamino]-3',4'-dichloroacetophenone (Compound AD-094);

N-(4-tert-butylbenzyl)-N-methyl-[2-(3,4-dichlorophenyl)-2-propenyl]amine (Compound AD-095);

2-[N-(4-tert-butylbenzyl)-N-methylamino]-3'-methoxyacetophenone (Compound AD-097);

N-(4-tert-butylbenzyl)-N-methyl-[2-(3-methoxyphenyl)-2-propenyl]amine (Compound AD-098);

2-[N-(4-tert-butylbenzyl)-N-methylamino]-4'-piperidinoacetophenone (Compound AD-100);

N-(4-tert-butylbenzyl)-N-methyl-[2-(4-piperidinophenyl)-2-propenyl]amine (Compound AD-101);

2-[N-(4-tert-butylbenzyl)-N-methylamino]-4'-cyanoacetophenone (Compound AD-103);

4-[1-{N-(4-tert-butylbenzyl)-N-methylamino}methyl]vinylbenzonitrile (Compound AD-104);

Ethyl 4-[2-{N-(4-tert-butylbenzyl)-N-methylamino}acetyl]benzoate (Compound AD-106);

Ethyl 4-[1-{N-(4-tert-butylbenzyl)-N-methylamino}methyl]vinylbenzoate (Compound AD-107);

4-[1-{N-(4-tert-butylbenzyl)-N-methylamino}methyl]vinylbenzoic acid (Compound AD-109);

N-(4-tert-butylbenzyl)-N-ethyl-2-phenyl-2-propenylamine (Compound AD-111);

N-(4-tert-butylbenzyl)-N-isopropyl-2-phenyl-2-propenylamine (Compound AD-113); and N-(4-tert-butylbenzyl)-N-cyclopropyl-2-phenyl-2-propenylamine (Compound AD-115).

(iii) Salts of Amine Derivatives represented by General Formula (1)

In the present invention, the salts of the amine derivatives represented by the general formula (1) above are not limited particularly so far as they are physiologically acceptable.

Preferably they include, for example, mineral acid salts such as hydrochloride, sulfate, nitrate, and phosphate, organic acid salts such as citrates, oxalates, fumarates, maleates, formates, acetates, methanesulfonates, benzenesulfonates, and paratoluenesulfonates, and carbonates. Among these, hydrochloride is preferred. These salts can be obtained by a conventional method by using the amine derivative (1) and an acid. For example, they can be obtained by mixing the amine derivative (1) and an acid in a polar or non-polar solvent.

The amine derivatives represented by the general formula (1) of the present invention can be produced, for example, by the method for producing an amine derivatives according to the present invention shown below.

(2) Method for Producing Amine Derivatives of the Present Invention

The method for producing amine derivatives of the present invention is characterized by following one of the reaction schemes (Method I) or (Method II) set forth below to produce the amine derivatives represented by the general formula (1) above.

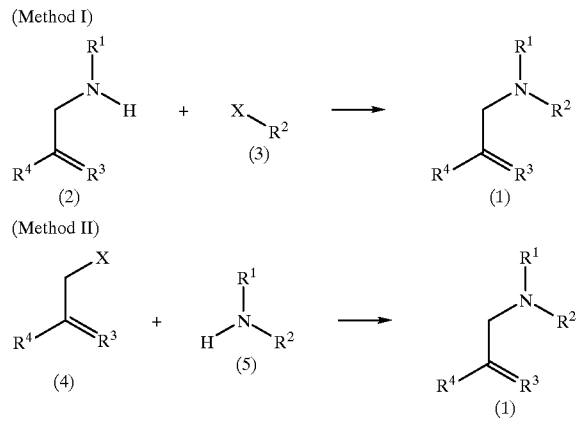

[in the formula, $R^1$, $R^2$, $R^3$, and $R^4$ represent the same meanings as explained above concerning the amine derivatives of the present invention represented by the general formula (1) and X represents a halogen atom.]

More specifically, the compounds (1) of the invention can be produced by condensing a secondary amine derivative represented by general formula (2) or salts thereof with a halogenated compound represented by general formula (3) (Method I) or condensing a halogenated compound represented by general formula (4) with a secondary amine derivative represented by general formula (5) or salts thereof (Method II). The condensing reactions can be carried out, for example, by using a condensing agent in the presence of a solvent.

The secondary amine derivatives represented by the general formulae (2), (3), (4), and (5), salts thereof and halogenated compounds can be easily obtained by one skilled in the art by production, purchase, or the like or can be obtained by conversion of substituent group(s) by general techniques.

In (Method I) or (Method II), the ratio of the secondary amine derivative and halogenated-compound used as raw materials, is usually 0.1 to 10.0 moles, particularly preferably 1.0 to 2.5 moles of the secondary amine derivative per mole of the halogenated compound. As the condensing agent for the reaction, tertiary organic amines and inorganic bases can be used. Specific examples thereof include triethylamine, N,N-diisopropylethylamine, anhydrous potassium carbonate, anhydrous sodium carbonate and so forth. The condensing agents are used in amounts of usually 0.1 to 30.0 moles, preferably 2.0 to 5.0 moles, for the total mole of the secondary amine and halogenated compound. The reaction can be proceeded in the absence of condensing agents.

The solvent to be used in the reaction is not limited particularly so far as it is non-aqueous solvent which can dissolve the two raw materials and specifically includes N,N-dimethylformamide (hereinafter, sometimes referred to as "DMF") and so forth. The amount of solvent to be used is preferably 5 to 100 times of the total weight of the secondary amine and the halogenated compound. The solvents may be used solely or more than two of them can be used in combination. The solvent may be selected so as to be suited to the physical properties of raw materials and condensing agent used in the reaction.

The reaction temperature may be any temperature of from room temperature to a temperature near the boiling point of the solvent used. Room temperature is preferred. The reaction time may vary depending on various conditions but usually it takes 10 minutes to 30 days. Post-treatment of the reaction and purification method may be carried out by general methods, for example, appropriate combinations of quenching with water, solvent extraction, column chromatography, recrystallization and so forth, Before or after (Method I) and (Method II), conversion of substituent groups may be carried out, if desired, to obtain other compounds represented by the general formula (1). Specific examples of the conversion of substituent groups include the following:

Halogenation using N-bromosuccinimide, bromine, copper dibromide and so forth;

Conversion of a primary amino group into a secondary amino group using a halogenated alkyl;

Conversion into an acid halide compound by reacting a carboxyl group with a halogenating agent such as thionyl chloride and subsequent reaction with an amine derivative to form an amide bond;

Conversion into an amine derivative by reacting an amide bond with a reducing agent such as lithium aluminum hydride;

Conversion of a nitro group into an amino group using a reducing agent such as zinc metal and so forth;

Conversion of a carbonyl group into a carbon-carbon double bond using wittig reaction;

Silylation using tert-butyldimethylchlorosilane and so forth;

Desilylation using n-butylammonium fluoride and so forth;

Introduction of a formyl group using hexamethylenetetramine and so forth;

Conversion into a secondary amine derivative by reacting a formyl group with a primary amine derivative and subsequent reduction;

Conversion of an alkoxycarbonyl group into carboxyl group by hydrolysis reaction; and the like. One skilled in the art can carry out the conversion of substituent groups by using general techniques.

The amine derivatives represented by the general formula (1) above and salts thereof according to the present invention are excellent in antimycotic effects and are highly useful as an antimycotic agent comprising the same, an antimycotic composition comprising the same, and a pharmaceutical composition containing the same as an active ingredient.

Hereinafter, explanation will be made of an antimycotic agent comprising the amine derivative or salts thereof of the present invention and an antimycotic composition and a pharmaceutical composition comprising the amine derivative or salts thereof of the present invention.

(3) Antimycotic Agent, Antimycotic Composition, and Pharmaceutical Composition of the Present Invention The antimycotic agent of the present invention comprises the amine derivative represented by the general formula (1)

above or salts thereof according to the present invention. The antimycotic agent of the present invention, like conventionally known antimycotic agents, can be used, for example, by compounding a generally used composition which an antimycotic agent is to be added as a compounding ingredient with the antimycotic agent of the present invention, instead of a conventionally known antimycotic agent, with appropriately selecting its compounding amount.

The antimycotic composition and pharmaceutical composition of the present invention (hereinafter, both are sometimes referred to as "the composition of the present invention") can be produced by compounding one or more of the compounds represented by the general formula (1) or salts thereof. The composition of the present invention can be formulated as any type of composition without a particular limit so far as it is known to contain an antimycotic agent, and includes for example, pharmaceutical composition such as external formulations for skin and external formulations for cleaning/sterilization, cloths such as stockings and underwear, plastic products such as a toothbrush and a ball-point pens. Pharmaceutical compositions, in particular, external formulations for skin are most preferred. The compound represented by the general formula (1) or salts thereof can be introduced into the composition of the present invention by a conventional technique. For example, in case of pharmaceutical compositions, the compound (1) or salts thereof together with other ingredients may be emulsified, solubilized-or mixed with powder ingredient. For cloths, the compound (1) or salts thereof may be melt-mixed with other ingredients and spun in the step of producing fiber or dipping to cloths. For plastic products, the compound (1) or salts thereof may be melt-mixed. Further, the compound (1) or salts thereof can be dipped to wood for preventing molds.

The composition of the present invention may optionally contain any ingredients that may be usually contained in compositions of these types in addition to the compound represented by the general formula (1) or salts thereof as required. Though such optional ingredients are not limited particularly, in the present invention generally include, for example, when the composition is pharmaceutical formulations, excipients, coloring agents, taste/odor correcting agent, binders, disintegrating agents, coating agents, stabilizers, pH adjusting agents, sweetening agents, and emulsifying/dispersing/solubilizing agents. Particularly, for external formulations for skin, there can be cited, for example, hydrocarbons such as liquid paraffin and vaseline, esters such as spermaceti and beeswax, triglycerides such as olive oil and beef tallow, higher alcohols such as cetanol and oleyl alcohol, fatty acids such as stearic acid and oleic acid, polyhydric alcohols such as propylene glycol and glycerol, nonionic surfactants, anionic surfactants, cationic surfactants, thickening agents, etc. For cloths or plastics, there can be cited, for example, plasticizers, crosslinking agents, coloring agents, antioxidants, ultraviolet absorbents, etc. The amount of the compound represented by the general formula (1) or salts thereof to be compounded in the inventive composition is not limited particularly but the amount is preferred from 0.001 to 20% by weight, more preferred 0.01 to 15% by weight, practically preferred 0.1 to 10% by weight.

EXAMPLES

Hereinafter, the present invention will be described in more detail by examples. However, the present invention should not be limited thereto.

Preparation Examples for Raw Material

The novel compounds of the present invention can be produced by various halogen compounds and secondary amines as raw materials. Hereinafter, preparation examples for the various halogen compounds and secondary amines which can be used as raw materials of the novel compounds of the invention will be described.

Preparation Example 1

Preparation of 2-Bromo-4'-Fluoro-acetophenone

In 25 ml of diethyl ether was dissolved 5.00 g (36.2 mmol) of p-fluoroacetophenone and while stirring the solution on an ice bath, 5.8 g (36.2 mmol) of bromine was dropped. After dropping, the mixture was stirred for 5 minutes and then the solvent was distilled off under reduced pressure. The residue thus obtained was purified by silica gel column chromatography (chloroform 100%). The results of NMR measurement revealed that it contained the target compound, and in addition, the raw materials and a dibromo form as a side product. Yield after adjustment was 6.21 g and % yield was 79.0%.

$^1$H-NMR (CDCl$_3$, ppm) 4.42 (s, 2 H), 7.12~8.18 (m, 4 H)

Preparation Example 2

Preparation of 2-bromo-2'-fluoro-acetophenone

2'-fluoroaceetophenone was used as a raw material and the target compound was obtained in the same manner as in Preparation Example 1.

$^1$H-NMR (CDCl$_3$, ppm) 4.54 (dd, J=2.34 Hz. 1.08 Hz, 2 H), 7.11~7.29 (m, 2 H), 7.59 (m, 1 H), 7.96 (m, 1 H)

Preparation Example 3

Preparation of 2,2'-dibromoacetophenone

2'-bromoacetophenone was used as a raw material and the target compound was obtained in the same manner as in Preparation Example 1.

$^1$H-NMR (CDCl$_3$, ppm) 4.95 (s, 2 H), 7.32~7.66 (m, 4 H)

Preparation Example 4

Preparation of 2,3'-dibromoacetophenone

3'-bromoacetophenone was used as a raw material and the target compound was obtained in the same manner as in Preparation Example 1.

$^1$H-NMR (CDCl$_3$, ppm)
4.42 (s, 2 H), 7.39 (t, J=7.83 Hz, 1 H) 7.72~7.76 (m, 1 H), 7.92 (m, 1 H), 8.13 (t, J=1.89 Hz, 1 H)

Preparation Example 5

Preparation of 2-bromo-3'-methylacetophenone 31-methylacetophenone was used as a raw material and the target compound was obtained in the same manner as in Preparation Example 1.

$^1$H-NMR (CDCl$_3$, ppm) 2.43 (s, 3 H), 4.45 (s, 2 H), 7.35~7.44 (m, 3 H), 7.80 (s, 1 H)

Preparation Example 6

Preparation of 2-bromo-2'-methylacetophenone

2'-methylacetophenone was used as a raw material, synthesis was carried out in the same manner as in Preparation Example 1 and the product was used as it was in subsequent reaction without isolation and purification.

Preparation Example 7

Preparation of 2-bromo-2'-methoxyacetophenone

2'-methoxyacetophenone was used as a raw material and the target compound was obtained in the same manner as in Preparation Example 1.

¹H-NMR (CDCl₃, ppm) 3.95 (s, 3 H), 4.61 (s, 2 H), 6.96~7.11 (m, 2 H), 7.52 (m, 1 H), 7.85 (m, 1 H)

Preparation Example 8

Preparation of 2-bromo-4'-nitroacetophenone

4'-nitroacetophenone was used as a raw material and the target compound was obtained in the same manner as in Preparation Example 1.

¹H-NMR (CDCl₃, ppm) 5.45 (s, 2 H), 8.16 (d, J=8.91 Hz, 2 H), 8.35 (d, J=8.91 Hz, 2 H)

Preparation Example 9

Preparation of 2-bromo-3'-nitroacetophenone m-nitroacetophenone was used as a raw material and the target compound was obtained in the same manner as in Preparation Example 1.

¹H-NMR (CDCl₃), ppm) 4.50 (s, 2 H), 7.74 (t, J=8.10 Hz, 1 H), 8.33 (d, J=8.10 Hz, 1 H), 8.48 (d, J=8.10 Hz, 1 H), 8.82 (s, 1 H)

Preparation Example 10

Preparation of 2-bromo-3',4'-dimethylacetophenone

3',4'-dimethylacetophenone was used as a raw material and the target compound was obtained in the same manner as in Preparation Example 1.

¹H-NMR (CDCl₃, ppm)
2.33 (s, 6 H), 4.43 (s, 2 H), 7.24 (d, J=9.45 Hz, 1 H), 7.71 (dd, J=7.83 Hz, 1.89 Hz, 1 H), 7.76 (s, 1 H)

Preparation Example 11

Preparation of 2-bromo-2',4'-dimethylacetophenone

2',4'-dimethylacetophenone was used as a raw material and the target compound was obtained in the same manner as in Preparation Example 1.

¹H-NMR (CDCl₃, ppm) 2.37 (s, 3 H, 2.47 (s, 3 H, 4.41 (s, 2 H) 7.06~7.14 (m, 2 H), 7.62 (d, J=8.64 Hz, 1 H)

Preparation Example 12

Preparation of 2-bromo-4'-tert-butylacetophenone

4'-tert-butylacetophenone was used as a raw material and the target compound was obtained in the same manner as in Preparation Example 1.

¹H-NMR (CDCl₃, ppm) 1.23 (s, 9 H), 4.44 (s, 2 H), 7.51 (d, J=8.64 Hz, 2 H), 7.93 (d, J=8.64 Hz, 2 H)

Preparation Example 13

Preparation of 2-bromo-3'-cyanoacetophenone m-cyanoacetophenone was used as a raw material and the target compound was obtained in the same manner as in Preparation Example 1.

¹H-NMR (CDCl₃, ppm) 4.42 (s, 2 H), 7.66 (t, J=8.10 Hz, 1 H), 7.90 (d, J=8.10 Hz, 1 H), 8.22 (t, J=8.10 Hz, 1 H), 8.28 (s, 1 H)

Preparation Example 14

Preparation of 4'-tert-butyldimethylsilyloxyacetophenone

N,N-dimethylformamide (70 ml), was mixed with 5.00 g (36.7 mmol), of 4'-hydroxyacetophenone, 6.64 g (44.1 mmol), of tert-butyldimethylchlorosilane, and 6.00 g (88.1 mmol), of imidazole and the mixture was stirred for 12 hours at room temperature. The reaction mixture was poured onto ice water to stop the reaction and extracted with 100 ml of ethyl acetate. The organic extract was washed with 100 ml of water ten times and then with saturated saline and dried with anhydrous sodium sulfate. The solvent was distilled off under reduced pressure and the resulting residue was purified by silica gel column chromatography (chloroform 100%), to obtain 5.23 g (yield: 56.9%), of the target compound.

¹H-NMR (CDCl₃, ppm) 0.23 (s, 3 H×2), 0.98 (s, 9 H), 2.55 (s, 3 H), 6.87 (dd, J=7.02 Hz, 1.89 Hz, 2 H), 7.88 (dd, J=7.02 Hz, 1.89 Hz, 2 H)

Preparation Example 15

Preparation of 2-bromo-4'-tert-butydilmethylsilyloxyacetophenone

Using 4'-tert-butyldimethylsilyloxyacetophenone obtained in Preparation Example 14 above as a raw material, the target compound was obtained in the same manner as in Preparation Example 1.

¹H-NMR (CDCl₃, ppm) 0.25 (s, 3 H×2), 0.99 (s, 9 H), 4.40 (s, 2 H), 6.90 (d, J=8.91 Hz, 2 H), 7.93 (d, J=8.91 Hz, 2 H)

Preparation Example 16

Preparation of 2-bromo-2'-hydroxyacetophenone

Ethyl acetate (40 ml), was mixed with 13.8 g (61.8 mmol), of copper dibromide, and a solution of 5.00 g (37.0 mmol), of o-hydroxyacetophenone in 40 ml of chloroform was dropped while refluxing with heating, the mixture being refluxed for additional 4 hours. White crystals precipitated were filtered and the filtrate was washed with water and with saturated saline and dried with anhydrous sodium sulfate. Then the solvent was distilled off under reduced pressure. The raw material, o-hydroxyacetophenone, was removed from the resulting residue by distillation under reduced pressure to obtain 4.12 g (yield: 51.8%), of the target compound as a pale yellow oily substance.

¹H-NMR (CDCl₃, ppm) 4.45 (s, 2 H), 6.91~7.01 (m, 2 H), 7.53 (m3 1 H), 7.74 (m, 1 H), 11.7 (s, 1 H)

Preparation Example 17

Preparation of 2-bromo-3',5'-difluoroacetophenone

3',5'-difluoroacetophenone was used as a raw material and the target compound was obtained in the same manner as in Preparation Example 1.

¹H-NMR (CDCl₃, ppm) 4.38 (s, 2 H), 7.07 (m, 1 H), 7.47~7.54 (m, 2 H)

Preparation Example 18

Preparation of 2-bromo-3',4'-difluoroacetophenone

3',4'-difluoroacetophenone was used as a raw material and the target compound was obtained in the same manner as in Preparation Example 1.

H-NMR (CDCl₃, ppm) 4.38 (s 2 H), 7.11 (m, 1 H), 7.65~8.02 (m, 2 H)

Preparation Example 19

Preparation of α-bromomethyl-styrene

Benzene (120 ml), was mixed with 9.00 g (76.2 mmol), of α-methylstyrene, 14.2 g (80.0 mmol), of N-bromosuccinimide, and 300 mg of benzoyl peroxide and the mixture was refluxed for 24 hours. After the solvent was distilled off under reduced pressure, carbon tetrachloride was added and the resulting crystals were filtered. The filtrate was concentrated under reduced pressure and the resulting residue was purified by silica gel column chromatography (n-hexane 100%), to obtain the target compound. The yield, % yield and NMR spectrum were as follows. Yield: 7.72 g, % yield: 51.5%.

$^1$H-NMR (CDCl$_3$, ppm) 4.39 (s, 2 H), 5.49 (s, 1 H), 5.56 (s, 1 H) 7.25~7.55 (m, 5 H)

Preparation Example 20

Preparation of N-ethyl-2-phenyl-2-propenylamine 12.42 g (152 mmol), of ethylamine hydrochloride is dissolved in 50 ml of methanol, and 15.42 g (152 mmol) of triethylamine was dropped into the solution under ice cooling while stirring. Further, 5 ml of the methanol solution containing 3.0 g (15.2 mmol), of α-bromomethylstyrene obtained in Preparation Example 19 was dropped. Then, after heating to room temperature, the mixture was stirred for 91 hours. After concentration, pH of the reaction mixture was changed to alkaline with sodium hydrogen carbonate and extracted with 150 ml and 100 ml of chloroform. After drying with magnesium sulfate, the solvent was distilled off under reduced pressure and the resulting residue was purified by silica gel column chromatography (chloroform:methanol=100:1→100:2), to obtain 890 mg (yield: 36.3%) of the target compound.

$^1$H-NMR (CDCl$_3$, ppm) 1.10 (t, J=7.29 Hz, 3 H), 2.68 (q, J=7.29 Hz, 2 H), 3.67 (s, 2 H), 5.23 (s, 1 H), 5.39 (s, 1 H), 7.22~7.48 (m, 5 H)

Preparation Example 21

Preparation of 2-bromo-4'-methylacetophenone

4'-methylacetophenone was used as a raw material and the target compound was obtained in the same manner as in Preparation Example 1.

$^1$H-NMR (CDCl$_3$, ppm) 2.43 (S, 3 H), 4.43 (s, 2 H), 7.29 (d, J=8.10 Hz, 2 H), 7.88 (d, J=8.10 Hz, 2 H)

Preparation Example 22

Preparation of 2-bromo-3'-fluoro-acetophenone

3'-fluoroacetophenone was used as a raw material and the target compound was obtained in the same manner as in Preparation Example 1.

$^1$H-NMR (CDCl$_3$, ppm) 4.43 (s, 2 H), 7.32 (m, 1 H), 7.49 (m, 1 H) 7.68 (m, 1 H), 7.77 (m, 1 H)

Preparation Example 23

Preparation of 2-bromo-2'-chloroacetophenone

2'-chloroacetophenone was used as a raw material and the target compound was obtained in the same manner as in Preparation Example 1.

$^1$H-NMR (CDCl$_3$, ppm) 4.53 (s, 2 H), 7.30~7.52 (m, 3 H), 7.57 (d, J=7.56 Hz, 1 H)

Preparation Example 24

Preparation of 2-bromo-4'-cyanoacetophenone

4'-cyanoacetophenone was used as a raw material and the target compound was obtained in the same manner as in Preparation Example 1.

$^1$H-NMR (CDCl$_3$, ppm) 4.43 (s, 2 H), 7.83 (d, J=7.02 Hz, 1 H), 8.09 (d, J=7.02 Hz, 2 H)

Preparation Example 25

Preparation of ethyl 4-(2-bromoacetyl)benzoate

Ethyl 4-acetylbenzoate was used as a raw material and the target compound was obtained in the same manner as in Preparation Example 1.

$^1$H-NMR (CDCl$_3$, ppm) 1.42 (t, J=7.29 Hz, 3 H), 4.42 (q, J=7.29 Hz, 2 H), 4.47 (s, 2 H), 8.04 (d, J=8.91 Hz, 2 H), 8.16 (d, J=8.91 Hz, 2 H)

Preparation Example 26

Preparation of 2-bromo-2',4'-dichloroacetophenone

2',4'-dichloroacetophenone was used as a raw material and the target compound was obtained in the same manner as in Preparation Example 1.

$^1$H-NMR (CDCl$_3$, ppm) 4.50 (s, 2 H), 7.37 (dd, J=7.02 Hz, 1.89 H z, 1 H), 7.48 (d, J=1.89 Hz, 1 H), 7.57 (d, J=7.02 Hz, 1 H)

Preparation Example 27

Preparation of 2-bromo-3',4'-dichloroacetophenone

3',4'-dichloroacetophenone was used as a raw material and the target compound was obtained in the same manner as in Preparation Example 1.

$^1$H-NMR (CDCl$_3$, ppm) 4.38 (s, 2 H), 7.59 (d, J=8.37 Hz, 1 H), 7.82 (dd, J=8.37 Hz, 1.89 Hz, 1 H), 8.07 (d, J=1.89 Hz, 1 H)

Preparation Example 28

Preparation of N-isopropyl-2-phenyl-2-propenylamine 9 g of isopropylamine was dissolved in 20 ml of methanol under stirring with ice cooling, and 5 ml of the methanol containing 3.0 g (15.2 mmol), of α bromomethylstyrene obtained in Preparation Example 19 was dropped into the solution. After heating to room temperature and stirring for 18 hours, the solution was washed by concentration under reduced pressure. 150 ml of chloroform was added to the residue and the solution was washed with saturated sodium hydrogen carbonate. After drying the solution with magnesium sulfate, the solvent was distilled off. Purification was performed by silica gel column chromatography (chloroform~chloroform:methanol=50:1). Yield: 2.14 g, % yield: 80.3%.

$^1$H-NMR (CDCl$_3$, ppm) 1.06 (d, J=6.48 Hz, 6 H), 2.85 (7 doublets, J=6.48 Hz, 1 H), 3.66 (s, 2 H), 5.24 (s, 1 H) 5.39 (s, 1 H), 7.25~7.50 (m, 5 H)

Preparation Example 29

Preparation of N-cyclopropyl-2-phenyl-2-propenylamine

Using cyclopropylamine instead of isopropylamine as a raw material, the target compound was obtained in the same manner as in Preparation Example 28.

$^1$H-NMR (CDCl$_3$, ppm)

0.30~0.50 (m, 4 H), 2.15 (m, 1 H), 3.73 (s, 2 H), 5.23 (s, 1 H), 5.39 (s, 1 H), 7.23~7.52 (m, 5 H)

Preparation Example 30

Preparation of N-(6,6-dimethyl-2-hepten-4-ynyl) methylamine (Compound PR-1133)

First, 1-bromo-6,6-dimethyl-2-hepten-4-yne was synthesized by the method described in J. Med. Chem. 1984, Vol.

27, page 1539 and used for the synthesis of the target compound below. 2.02 g of triethylamine was added to 40 ml of a 40% methylamine-methanol solution under ice cooling and while stirring the mixture, 3.5 ml of the methanol solution containing 4.02 g of 1-bromo-6,6-dimethyl-2-hepten-4-yne obtained as above was dropped. After dropping, the ice bath was removed and the reaction mixture was stirred at room temperature for 88 hours. Then, under reduced pressure, the residue obtained by distilling off methanol from the reaction mixture was dissolved in an aqueous 1N hydrochloric acid solution, then was washed with ether. pH of the water extract after washing was changed to alkaline with an aqueous 2N sodium hydroxide solution and extracted with 100 ml of chloroform twice. The organic extract thus obtained was dried with magnesium sulfate and then the solvent was distilled off under reduced pressure. The residue after the distilling off the solvent was purified by silica gel column chromatography (chloroform~chloroform:methanol=100:1~10:1) to obtain the target compound as an oily substance.

The yield, % yield and results of measurement on NMR are shown below. Analysis of NMR spectrum revealed that N-(6,6-dimethyl-2-hepten-4-ynyl)methylamine obtained in this Preparation Example was a mixture of a trans-form and a cis-form (trans:cis=3:1). Yield: 2.02 g, % yeild: 66.9%

$^1$H-NMR (CDCl$_3$, ppm), trans form corresponding peak 1.24 (s, 9 H), 2.41 (s, 3 H), 3.23 (dd, J=6.48 Hz, 1.35 Hz, 2 H), 5.62 (dt, J=15.93 Hz, 1.35 Hz, 1 H), 6.07 (dt, J=15.93 Hz, 6.48 Hz, 1 H), 1.53 (broad s, estimated N–H+H$_2$O)

$^1$H-NMR (CDCl$_3$, ppm), cis form corresponding peak 1.26 (s, 9 H), 2.44 (s, 3 H), 3.43 (dd, J=6.75 Hz, 1.35 Hz, 2 H), 5.57 (dt, J=10.53 Hz, 1.35 Hz, 1 H), 5.89 (dt, J=10.53 Hz, 6.75 Hz, 1 H), 1.53 (broad s, estimated N–H+H$_2$O)

Preparation Example 31

Preparation of N-(4-tert-butylbenzyl)methylamine

Chloroform (100 ml), was mixed with 10.1 g (56.6 mmol), of p-tert-butylbenzoic acid and 20.2 g of thionyl chloride, and the mixture was refluxed for 5 hours. The solvent and excess thionyl chloride were distilled off under reduced pressure and the residue was dissolved in a small amount of methanol. The solution was dropped to 17 ml of a 40% methylamine-methanol solution cooled on an ice bath. After dropping, the solution was taken out of the ice bath and stirred at room temperature for 48 hours. Then, 100 ml of 2N hydrochloric acid was added to the reaction mixture, which was extracted with dichloromethane, and after washing with water and saturated saline, respectively, the organic layer was dried with magnesium sulfate. After distilling off the solvent under reduced pressure, the resulting white crystals were dissolved in dichloromethane and the solution was washed with 1 liter of a saturated aqueous sodium hydrogen carbonate solution to remove p-tert-butylbenzoic acid, raw material. After the organic extract was dried with magnesium sulfate, the solvent was distilled off under reduced pressure to obtain 8.15 g (yield: 74.9%), of N-methyl-4-tert-butylbenzamide as white crystals. This was mixed with 110 ml of diethyl ether, 8.15 g (42.6 mmol), of N-methyl-4-tert-butylbenzamide and 2.88 g (85.2 mmol), of lithium aluminum hydride, and refluxed in nitrogen atmosphere for 6 hours. After the reflux, the reaction mixture was ice cooled and water was added thereto to decompose excess lithium aluminum hydride. Aluminum hydroxide deposited was filtered off and the filtrate was extracted with diethyl ether. After washing with water and saturated saline, respectively, the organic extract was dried with magnesium sulfate. The solvent was distilled off under reduced pressure and the resulting yellow oily substance was distilled under reduced pressure (115 to 118°C./10 mmHg), to obtain 3.69 g (yield: 48.9%), of the target compound as yellow oily substance.

$^1$H-NMR (CDCl$_3$, ppm) 1.31 (9H, s), 2.45 (3H, s), 7.24 (2H, d, J=8.37 Hz), 7.35 (2H, d, J=8.37 Hz)

Preparation Example 32

Preparation of N-(4-tert-butylbenzyl)methylamine (2)

14.8 g (0.10 mol), of p-tert-butyltoluene was dissolved in carbon tetrachloride, and 17.8 g (0.10 mol), of N-bromosuccinimide and 200 mg of benzoyl peroxide are added to the solution, and the mixture was refluxed for 2 hours. After cooling, insoluble matter was filtered off. The residue was washed with carbon tetrachloride and the filtrate was concentrated under reduced pressure. The residue was dissolved in n-hexane and the solution was dried with magnesium sulfate. Thereafter, the solvent was distilled off under reduced pressure to obtain 22.7 g (yield: 100%, however, the results of $^1$H-NMR revealed that the product was a mixture of the target compound:raw material:dibromo form=10:1:1), of p-tert-butylbenzylbromide. 10.6 g (0.10 mol), of sodium carbonate was added to 200 ml of a 40% methylamine-methanol solution, and 20 ml of the methanol containing 22.7 g (0.10 mol), of p-tert-butylbenzyl bromide was dropped in an ice bath. After taking out of the ice bath, the solution was stirred at room temperature for 41 hours. The methanol was distilled off under reduced pressure and water was added to the residue, followed by extraction with 400 ml of ether. The ether part was extracted twice with 200 ml and 100 ml, respectively, of 1N hydrochloric acid and the water part was extracted with ethyl acetate. Then, the water extract was changed to alkaline with an aqueous 2N sodium hydroxide solution and extracted with 400 ml of ether. After drying the extracts with magnesium sulfate, the solvent was distilled off under reduced pressure. The residue was purified by silica gel column chromatography (chloroform:methanol=200:1→100:1→20:1), to obtain the target substance of 9.51 g (yield: 53.7%).

$^1$H-NMR (CDCl$_3$, ppm) 1.31 (9H, s), 2.45 (3H, s), 7.24 (2H, d, J=8.37 Hz), 7.35 (2H, d, J=8.37 Hz)

Preparation Example 33

Preparation of N-methyl-(1-naphthylmethyl)amine 1.14 g (11.3 mmol), of triethylamine was mixed with a 40% methylamine-methanol solution and 5 ml of the methanol containing 2.00 g (11.3 mmol), of 1-chloromethylnaphthalene was dropped while stirring in an ice bath. After dropping, the reaction mixture was taken out of the ice bath and stirred at room temperature for 60 hours. The solvent was distilled off under reduced pressure and extracted with ether-2N hydrochloric acid. The organic extract was washed with saturated saline and dried with sodium sulfate. Then, the solvent was distilled off under reduced pressure to obtain 1.78 g (yield: 91.9%), of the target compound as a pale yellow oil.

$^1$H-NMR (CDCl$_3$, ppm) 2.56 (3 H, s), 4.20 (2 H, s), 7.39~7.57 (4 H, m), 7.77 (1 H, dd, J=2.02 Hz, 7.43 Hz), 7.86 (1 H, dd, J=2.02 Hz, 8.23 Hz), 8.12 (1 H, d, J=7.83 Hz)

Preparation Example 34

Preparation of N-methyl-(2-naphthylmethyl)amine 2-bromomethylnaphthalene was used as a raw material and the target compound was obtained in the same manner as in Preparation Example 19.

$^1$H-NMR (CDCl$_3$, ppm) 2.50 (3 H, s), 3.92 (2 H, s), 7.41~7.50 (3 H, m), 7.80~7.90 (4H, m)

Preparation Example 35

Preparation of 2-bromo-2'-acetonaphthone

2'-acetonaphthone was used as a raw material and the target compound was obtained in the same manner as in Preparation Example 3.

$^1$H-NMR (CDCl$_3$, ppm) 4.59 (2 H, s), 7.26~7.67 (2 H, m), 7.87~8.06 (4H, m), 8.50 (1 H, m)

Preparation Example 36

Preparation of N-(2,2,2-trifluoroethyl)-2-phenyl-2-propenylamine

α-bromomethylstyrene obtained in Preparation Example 19 above was reacted with 2,2,2-trifluoroethylamine in the same manner as in Preparation Example 20 to obtain the target compound.

$^1$H-NMR (CDCl$_3$, ppm) 3.17 (2H, q, J=9.45 Hz), 3.78 (2H, s), 5.26 (1 H, s), 5.45 (1 H, s), 7.22~7.45 (5H, m)

Preparation Example 37

Preparation of 4-(1-methyl-1-phenylethyl) benzaldehyde

Trifluoroacetic acid (35 ml), was mixed with 3.93 g(20.0 mmol), of 2,2-diphenylpropane and 2.80 g (20.0 mmol), of hexamethylenetetramine and heated to reflux for 16 hours. After cooling to room temperature, the reaction mixture was poured into ice water and the mixture was stirred for 1 hour. The solution was adjusted to pH=about 9 and extracted with 100 ml of diethyl ether. The organic extract was washed with saturated saline and dried with sodium sulfate and the solvent was distilled off under reduced pressure. The resulting residue was purified by silica gel column chromatography (n-hexane:ethyl acetate=10:1), to obtain 3.61 g (yield: 80.5%), of the target compound as a pale yellow oily substance.

$^1$H-NMR (CDCl$_3$, ppm) 1.71 (3 H×2, s), 7.17~7.32 (5 H, m), 7.40 (2 H, d, J=8.37 Hz), 7.79 (2H, d, J=8.37 H z), 9.98 (1 H, s)

Preparation Example 38

Preparation of N-methyl-4-(1-1-methyl-phenylethyl) benzylamine 3.61 g (16.1 mmol), of 4-(1-methyl-1-phenylethyl) benzaldehyde obtained in Preparation Example 37 was dissolved in 40 ml of a 40% methylamine-methanol solution, and several particles of molecular sieves (4 Å), was added and the mixture was stirred at room temperature overnight. The reaction mixture was filtered, the filtrate was concentrated under reduced pressure, and the residue was extracted with 100 ml of diethyl ether. The organic extract was washed with saturated saline and dried with sodium sulfate and then the solvent was distilled off under reduced pressure. The residue was dissolved in 25 ml of methanol and 0.70 g of sodium borohydride was added thereto, followed by stirring at 50° C. for 1 hour. The solvent was distilled off under reduced pressure and the residue was extracted with 100 ml of diethyl ether. The organic extract was washed with saturated saline and dried with sodium sulfate and the solvent was distilled off under reduced pressure. The residue was dissolved in 10 ml of ethanol and an excess amount of 4N hydrogen chloride-ethyl acetate solution was added thereto. The solvent was distilled off under reduced pressure, 100 ml of diisopropyl ether was added to the residue and the crystals precipitated were collected by filtration. After neutralizing hydrochloric acid with an aqueous sodium hydroxide solution, the resulting crystals were extracted with ether to obtain 2.49 g (yield: 64.6%) the target compound as an orange oily substance.

$^1$H-NMR (CDCl$_3$, ppm) 1.68 (3 H×2, s), 2.46 (3H, s), 3.71 (2 H, s), 7.08~7.29 (9 H, m)

Examples of the Inventive Novel Compounds

Hereinafter, examples of the compounds represented by the general formula (1), of the present invention will be described. First, for each example, a list of R$^1$, R$^2$, R$^3$ and R$^4$ will be shown in Table 1 for examples of the first amine derivatives of the invention (Examples 1 to 36), and in Table 2 for examples of the second amine derivative of the invention (Examples 37 to 84). In some of the examples, hydrochloride are also described in the column of "Compound No." in Tables 1 and 2.

For the first amine derivative of the invention, because all of R$^4$ in the general formula (1), are groups represented by the formula (i), they were omitted in the list. In Tables 1 and 2, "–" in the column of R$^8$ means that there is no substituent group and the numerals in the round brackets indicate the position of bonding. Further, (a), (b), (c), (g), (h), and (i), mean groups represented by the formulae (a), (b), (c), (g), (h), and (i), respectively. —Ph represents a phenyl group.

Further, "PR-1133'" in Table 1 represents "(6,6-dimethyl-2-hepten-4-ynyl group", the group being represented by the following formula.

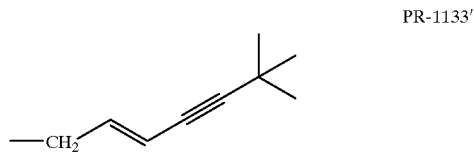

PR-1133'

In addition, "PR-1805'" represents "a cinnamyl group", which is represented by the following formula.

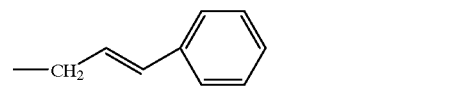

PR-1805'

TABLE 1-1

PR Compounds

| Exp. | Comp. No | R$^1$ | R$^2$ | R$^3$ | R$^8$ | | m |
|---|---|---|---|---|---|---|---|
| 1 | PR-1130 | —CH$_3$ | PR-1133' | =O | — | | 0 |
| 2 | PR-1257 | —CH$_3$ | PR-1133' | =CH$_2$ | — | | 0 |
| 3 | PR-1531 | —CH$_3$ | PR-1133' | =O | —CH$_3$ | (2) | 1 |
| 3 | PR-1532 | —CH$_3$ | PR-1133' | =CH$_2$ | —CH$_3$ | (2) | 1 |
| 4 | PR-1538 | —CH$_3$ | PR-1133' | =O | —CH$_3$ | (3) | 1 |
| 4 | PR-1539 | —CH$_3$ | PR-1133' | =CH$_2$ | —CH$_3$ | (3) | 1 |
| 5 | PR-1413 | —CH$_3$ | PR-1133' | =O | —CH$_3$ | (4) | 1 |
| 5 | PR-1414 | —CH$_3$ | PR-1133' | =CH$_2$ | —CH$_3$ | (4) | 1 |
| 6 | PR-1489 | —CH$_3$ | PR-1133' | =O | —F | (2) | 1 |
| 6 | PR-1490 | —CH$_3$ | PR-1133' | =CH$_2$ | —F | (2) | 1 |
| 7 | PR-1468 | —CH$_3$ | PR-1133' | =O | —F | (3) | 1 |
| 7 | PR-1469 | —CH$_3$ | PR-1133' | =CH$_2$ | —F | (3) | 1 |
| 8 | PR-1428 | —CH$_3$ | PR-1133' | =O | —F | (4) | 1 |
| 8 | PR-1429 | —CH$_3$ | PR-1133' | =CH$_2$ | —F | (4) | 1 |
| 9 | PR-1503 | —CH$_3$ | PR-1133' | =O | —Br | (2) | 1 |
| 9 | PR-1504 | —CH$_3$ | PR-1133' | =CH$_2$ | —Br | (2) | 1 |
| 10 | PR-1482 | —CH$_3$ | PR-1133' | =O | —Br | (3) | 1 |
| 10 | PR-1483 | —CH$_3$ | PR-1133' | =CH$_2$ | —Br | (3) | 1 |
| 11 | PR-1437 | —CH$_3$ | PR-1133' | =O | —Br | (4) | 1 |
| 11 | PR-1438 | —CH$_3$ | PR-1133' | =CH$_2$ | —Br | (4) | 1 |
| 12 | PR-1496 | —CH$_3$ | PR-1133' | =O | —Cl | (2) | 1 |
| 12 | PR-1497 | —CH$_3$ | PR-1133' | =CH$_2$ | —Cl | (2) | 1 |

TABLE 1-2

PR Compounds

| Exp. | Comp. No | $R^1$ | $R^2$ | $R^3$ | $R^8$ | m |
|---|---|---|---|---|---|---|
| 13 | PR-1416 | —$CH_3$ | PR-1133' | =O | —Cl (4) | 1 |
| 13 | PR-1417 | —$CH_3$ | PR-1133' | =$CH_2$ | —Cl (4) | 1 |
| 14 | PR-1632 | —$CH_3$ | PR-1133' | =O | —$OCH_3$ (2) | 1 |
| 14 | PR-1633 | —$CH_3$ | PR-1133' | =$CH_2$ | —$OCH_3$ (2) | 1 |
| 15 | PR-1388 | —$CH_3$ | PR-1133' | =O | —$OCH_3$ (3) | 1 |
| 15 | PR-1389 | —$CH_3$ | PR-1133' | =$CH_2$ | —$OCH_3$ (3) | 1 |
| 16 | PR-1639 | —$CH_3$ | PR-1133' | =O | —$NO_2$ (2) | 1 |
| 16 | PR-1640 | —$CH_3$ | PR-1133' | =$CH_2$ | —$NO_2$ (2) | 1 |
| 17 | PR-1646 | —$CH_3$ | PR-1133' | =O | —$NO_2$ (3) | 1 |
| 17 | PR-1647 | —$CH_3$ | PR-1133' | =$CH_2$ | —$NO_2$ (3) | 1 |
| 18 | PR-1393 | —$CH_3$ | PR-1133' | =O | —$NO_2$ (4) | 1 |
| 18 | PR-1394 | —$CH_3$ | PR-1133' | =$CH_2$ | —$NO_2$ (4) | 1 |
| 19 | PR-1552 | —$CH_3$ | PR-1133' | =O | —CN (3) | 1 |
| 19 | PR-1553 | —$CH_3$ | PR-1133' | =$CH_2$ | —CN (3) | 1 |
| 20 | PR-1559 | —$CH_3$ | PR-1133' | =O | —CN (4) | 1 |
| 20 | PR-1560 | —$CH_3$ | PR-1133' | =$CH_2$ | —CN (4) | 1 |
| 21 | PR-1685 | —$CH_3$ | PR-1133' | =O | —$COOC_2H_5$ (4) | 1 |
| 21 | PR-1686 | —$CH_3$ | PR-1133' | =$CH_2$ | —$COOC_2H_5$ (4) | 1 |
| 22 | PR-1517 | —$CH_3$ | PR-1133' | =O | —Cl (2,4) | 2 |
| 22 | PR-1518 | —$CH_3$ | PR-1133' | =$CH_2$ | —Cl (2,4) | 2 |
| 23 | PR-1510 | —$CH_3$ | PR-1133' | =O | —Cl (3,4) | 2 |
| 23 | PR-1511 | —$CH_3$ | PR-1133' | =$CH_2$ | —Cl (3,4) | 2 |

TABLE 1-3

1-3 PR Compounds

| Exp. | Comp. No | $R^1$ | $R^2$ | $R^3$ | $R^8$ | m |
|---|---|---|---|---|---|---|
| 24 | PR-1710 | —$CH_3$ | PR-1133' | =O | —$CH_3$ (2,4) | 2 |
| 24 | PR-1711 | —$CH_3$ | PR-1133' | =$CH_2$ | —$CH_3$ (2,4) | 2 |
| 25 | PR-1703 | —$CH_3$ | PR-1133' | =O | —$CH_3$ (3,4) | 2 |
| 25 | PR-1704 | —$CH_3$ | PR-1133' | =$CH_2$ | —$CH_3$ (3,4) | 2 |
| 26 | PR-2171 | —$CH_3$ | PR-1133' | =O | —F (3,4) | 2 |
| 26 | PR-2172 | —$CH_3$ | PR-1133' | =$CH_2$ | —F (3,4) | 2 |
| 27 | PR-2157 | —$CH_3$ | PR-1133' | =O | —F (3,5) | 2 |
| 27 | PR-2158 | —$CH_3$ | PR-1133' | =$CH_2$ | —F (3,5) | 2 |
| 28 | PR-1717 | —$CH_3$ | PR-1133' | =O | —$C(CH_3)_3$ (4) | 1 |
| 28 | PR-1718 | —$CH_3$ | PR-1133' | =$CH_2$ | —$C(CH_3)_3$ (4) | 1 |
| 29 | PR-1619 | —$CH_3$ | PR-1133' | =O | —OH (2) | 1 |
| 30 | PR-1604 | —$CH_3$ | PR-1133' | =O | —$OSi(CH_3)_2C(CH_3)_3$ (4) | 1 |
| 30 | PR-1605 | —$CH_3$ | PR-1133' | =$CH_2$ | —$OSi(CH_3)_2C(CH_3)_3$ (4) | 1 |
| 30 | PR-1606 | —$CH_3$ | PR-1133' | =$CH_2$ | —$OSi(CH_3)_2C(CH_3)_3$ (4) | 1 |
| 31 | PR-1672 | —$CH_3$ | PR-1133' | =$CH_2$ | —$NO_2$ (2) | 1 |
| 32 | PR-1676 | —$CH_3$ | PR-1133' | =$CH_2$ | —$NH_2$ (3) | 1 |
| 33 | PR-1806 | —$CH_3$ | PR-1805' | =$CH_2$ | — | 0 |
| 34 | PR-1853 | —$C_2H_5$ | PR-1133' | =$CH_2$ | — | 0 |
| 35 | PR-1855 | —$CH(CH_3)_2$ | PR-1133' | =$CH_2$ | — | 0 |
| 36 | PR-1930 | —$C_3H_5$ | PR-1133' | =$CH_2$ | — | 0 |

TABLE 2-1

2-1 AD Compounds

| Exp. | Comp. No | $R^1$ | $R^2$ | $R^5$ | $R^3$ | $R^4$ | $R^8$ | m |
|---|---|---|---|---|---|---|---|---|
| 37 | AD-001 | —$CH_3$ | (a) | —$CH_3$ | =O | (i) | — | 0 |
| 39 | AD-003 | —$CH_3$ | (a) | —$CH_3$ | =$CH_2$ | (i) | — | 0 |
| 41 | AD-005 | —$CH_3$ | (a) | —$CH_3$ | =O | (i) | —Br(4) | 1 |
| 41 | AD-006 | —$CH_3$ | (a) | —$CH_3$ | =$CH_2$ | (i) | —Br(4) | 1 |
| 42 | AD-008 | —$CH_3$ | (a) | —$CH_3$ | =O | (i) | —Cl(4) | 1 |
| 42 | AD-009 | —$CH_3$ | (a) | —$CH_3$ | =$CH_2$ | (i) | —Cl(4) | 1 |
| 43 | AD-011 | —$CH_3$ | (a) | —$CH_3$ | =O | (i) | —F(4) | 1 |
| 43 | AD-012 | —$CH_3$ | (a) | —$CH_3$ | =$CH_2$ | (i) | —F(4) | 1 |
| 44 | AD-014 | —$CH_3$ | (a) | —$CH_3$ | =O | (i) | —F(2) | 1 |
| 44 | AD-015 | —$CH_3$ | (a) | —$CH_3$ | =$CH_2$ | (i) | —F(2) | 1 |
| 45 | AD-017 | —$CH_3$ | (a) | —$CH_3$ | =O | (i) | —Br(2) | 1 |
| 45 | AD-018 | —$CH_3$ | (a) | —$CH_3$ | =$CH_2$ | (i) | —Br(2) | 1 |
| 46 | AD-020 | —$CH_3$ | (a) | —$CH_3$ | =O | (i) | —Br(3) | 1 |
| 46 | AD-021 | —$CH_3$ | (a) | —$CH_3$ | =$CH_2$ | (i) | —Br(3) | 1 |
| 47 | AD-023 | —$CH_3$ | (a) | —$CH_3$ | =O | (i) | —$CH_3$(3) | 1 |
| 47 | AD-024 | —$CH_3$ | (a) | —$CH_3$ | =$CH_2$ | (i) | —$CH_3$(3) | 1 |
| 48 | AD-026 | —$CH_3$ | (a) | —$CH_3$ | =O | (i) | —$CH_3$(2) | 1 |
| 48 | AD-027 | —$CH_3$ | (a) | —$CH_3$ | =$CH_2$ | (i) | —$CH_3$(2) | 1 |
| 49 | AD-029 | —$CH_3$ | (a) | —$CH_3$ | =O | (i) | —$OCH_3$(2) | 1 |
| 49 | AD-030 | —$CH_3$ | (a) | —$CH_3$ | =$CH_2$ | (i) | —$OCH_3$(2) | 1 |
| 50 | AD-032 | —$CH_3$ | (a) | —$CH_3$ | =$CH_2$ | (i) | —$NO_2$(2) | 1 |
| 51 | AD-034 | —$CH_3$ | (a) | —$CH_3$ | =$CH_2$ | (i) | —$NO_2$(4) | 1 |
| 52 | AD-036 | —$CH_3$ | (a) | —$CH_3$ | =$CH_2$ | (i) | —$NO_2$(3) | 1 |
| 53 | AD-038 | —$CH_3$ | (a) | —$CH_3$ | =$CH_2$ | (i) | —$NH_2$(3) | 1 |
| 54 | AD-040 | —$CH_3$ | (a) | —$CH_3$ | =$CH_2$ | (i) | —$NH_2$(2) | 1 |

TABLE 2-2

2-2 AD Compounds

| Exp. | Comp. No | $R^1$ | $R^2$ | $R^5$ | $R^3$ | $R^4$ | $R^8$ | m |
|---|---|---|---|---|---|---|---|---|
| 55 | AD-041 | —CH$_3$ | (a) | —CH$_3$ | =O | (i) | —CH$_3$(3,4) | 2 |
| 55 | AD-042 | —CH$_3$ | (a) | —CH$_3$ | =CH$_2$ | (i) | —CH$_3$(3,4) | 2 |
| 56 | AD-044 | —CH$_3$ | (a) | —CH$_3$ | =O | (i) | —CH$_3$(2,4) | 2 |
| 56 | AD-045 | —CH$_3$ | (a) | —CH$_3$ | =CH$_2$ | (i) | —CH$_3$(2,4) | 2 |
| 57 | AD-047 | —CH$_3$ | (a) | —CH$_3$ | =O | (i) | —C(CH$_3$)$_3$(4) | 1 |
| 57 | AD-048 | —CH$_3$ | (a) | —CH$_3$ | =CH$_2$ | (i) | —C(CH$_3$)$_3$(4) | 1 |
| 58 | AD-050 | —CH$_3$ | (a) | —CH$_3$ | =O | (i) | —CN(3) | 1 |
| 58 | AD-051 | —CH$_3$ | (a) | —CH$_3$ | =CH$_2$ | (i) | —CN(3) | 1 |
| 59 | AD-053 | —CH$_3$ | (a) | —CH$_3$ | =O | (i) | —OSi(CH$_3$)$_2$C(CH$_3$)$_3$(4) | 1 |
| 59 | AD-054 | —CH$_3$ | (a) | —CH$_3$ | =CH$_2$ | (i) | —OSi(CH$_3$)$_2$C(CH$_3$)$_3$(4) | 1 |
| 60 | AD-055 | —CH$_3$ | (a) | —CH$_3$ | =CH$_2$ | (i) | -OH(4) | 1 |
| 61 | AD-056 | —CH$_3$ | (a) | —CH$_3$ | =O | (i) | -OH(2) | 1 |
| 62 | AD-058 | —CH$_3$ | (b) | — | =CH$_2$ | (i) | — | 0 |
| 63 | AD-060 | —CH$_3$ | (c) | — | =CH$_2$ | (i) | — | 0 |
| 64 | AD-062 | —CH$_3$ | (c) | — | =O | (i) | —C(CH$_3$)$_{3(4)}$ | 1 |
| 64 | AD-063 | —CH$_3$ | (c) | — | =CH$_2$ | (i) | —C(CH$_3$)$_{3(4)}$ | 1 |
| 65 | AD-065 | —CH$_3$ | (b) | — | =O | (i) | —C(CH$_3$)$_{3(4)}$ | 1 |
| 65 | AD-066 | —CH$_3$ | (b) | — | =CH$_2$ | (i) | —C(CH$_3$)$_{3(4)}$ | 1 |
| 66 | AD-068 | —CH$_3$ | (a) | —CH$_3$ | =O | (h) | — | — |
| 66 | AD-069 | —CH$_3$ | (a) | —CH$_3$ | =CH$_2$ | (h) | — | — |
| 67 | AD-071 | —CH$_2$CF$_3$ | (a) | —CH$_3$ | =CH$_2$ | (i) | — | 0 |
| 68 | AD-072 | —CH$_3$ | (a) | —CH$_3$ | =O | (i) | —F(3,5) | 2 |
| 68 | AD-073 | —CH$_3$ | (a) | —CH$_3$ | =CH$_2$ | (i) | —F(3,5) | 2 |
| 69 | AD-075 | —CH$_3$ | (a) | —CH$_3$ | =O | (i) | —F(3,4) | 2 |
| 69 | AD-076 | —CH$_3$ | (a) | —CH$_3$ | =CH$_2$ | (i) | —F(3,4) | 2 |

TABLE 2-3

AD Compounds

| Exp. | Comp. No. | $R^1$ | $R^2$ | $R^5$ | $R^3$ | $R^4$ | $R^8$ | m |
|---|---|---|---|---|---|---|---|---|
| 70 | AD-078 | —CH$_3$ | (a) | —Ph | =CH$_2$ | (i) | — | 0 |
| 71 | AD-080 | —CH$_3$ | (a) | —CH$_3$ | =O | (i) | —CH$_3$(4) | 1 |
| 71 | AD-080 | —CH$_3$ | (a) | —CH$_3$ | =CH$_2$ | (i) | —CH$_3$(4) | 1 |
| 72 | AD-083 | —CH$_3$ | (a) | —CH$_3$ | =O | (i) | —F(3) | 1 |
| 72 | AD-084 | —CH$_3$ | (a) | —CH$_3$ | =CH$_2$ | (i) | —F(3) | 1 |
| 73 | AD-086 | —CH$_3$ | (a) | —CH$_3$ | =O | (i) | —Cl(2,4) | 2 |
| 73 | AD-087 | —CH$_3$ | (a) | —CH$_3$ | =CH$_2$ | (i) | —Cl(2,4) | 2 |
| 74 | AD-089 | —CH$_3$ | (a) | —CH$_3$ | =C(CH$_3$)$_2$ | (i) | — | 0 |
| 75 | AD-091 | —CH$_3$ | (a) | —CH$_3$ | =C | (i) | —Cl(2) | 1 |
| 75 | AD-092 | —CH$_3$ | (a) | —CH$_3$ | =CH$_2$ | (j) | —Cl(2) | 1 |
| 76 | AD-094 | —CH$_3$ | (a) | —CH$_3$ | =O | (i) | —Cl(3,4) | 2 |
| 76 | AD-095 | —CH$_3$ | (a) | —CH$_3$ | =CH$_2$ | (i) | —Cl(3,4) | 2 |
| 77 | AD-097 | —CH$_3$ | (a) | —CH$_3$ | =O | (i) | —OCH$_3$(3) | 1 |
| 77 | AD-098 | —CH$_3$ | (a) | —CH$_3$ | =CH$_2$ | (i) | —OCH$_3$(3) | 1 |
| 78 | AD-100 | —CH$_3$ | (a) | —CH$_3$ | =O | (i) | —C$_5$H$_{10}$(4) | 1 |
| 78 | AD-101 | —CH$_3$ | (a) | —CH$_3$ | =CH$_2$ | (i) | —NC$_5$H$_{10}$(4) | 1 |
| 79 | AD-103 | —CH$_3$ | (a) | —CH$_3$ | =O | (i) | —CN(4) | 1 |
| 79 | AD-104 | —CH$_3$ | (a) | —CH$_3$ | =CH$_2$ | (i) | —CN(4) | 1 |
| 80 | AD-106 | —CH$_3$ | (a) | —CH$_3$ | =O | (i) | —COOC$_2$H$_5$(4) | 1 |
| 80 | AD-107 | —CH$_3$ | (a) | —CH$_3$ | =CH$_2$ | (i) | —COOC$_2$H$_5$(4) | 1 |
| 81 | AD-109 | —CH$_3$ | (a) | —CH$_3$ | =CH$_2$ | (i) | —COOH(4) | 1 |
| 82 | AD-110 | —C$_2$H$_5$ | (a) | —CH$_3$ | =CH$_2$ | (i) | — | 0 |
| 83 | AD-113 | —CH(CH$_3$)$_2$ | (a) | —CH$_3$ | =CH$_2$ | (i) | — | 0 |
| 84 | AD-115 | —C$_3$H$_5$ | (a) | —CH$_3$ | =CH$_2$ | (i) | — | 0 |

Example 1

Trans-2-[N-(6,6-dimethyl-2-hepten-4-ynyl)-N-methylamino]acetophenone; (Compound PR-1130), and its hydrochloride; (Compound PR-1254)

N,N-Dimethylformamide (DMF), (35 ml), was mixed with 3.27 g (21.6 mmol), of N-(6,6-dimethyl-2-hepten-4-ynyl)methylamine (Compound PR-1133), and 7.46g (540 mmol), of potassium carbonate and a solution of 3.98 g (20.0 mmol), of 2-bromoacetophenone in 50 ml of DMF was dropped while stirring in an ice bath. After the dropping, the mixture was stirred as it was and the temperature was slowly elevated to room temperature, and stirring was continued at room temperature for additional 12 hours.

The reaction mixture was poured in a saturated aqueous sodium hydrogen carbonate solution with ices therein to stop the reaction. The reaction mixture was extracted with 100 ml of ethyl acetate, and the organic extract was washed with a saturated aqueous sodium hydrogen carbonate solution and with saturated saline and dried with anhydrous sodium sulfate.

The solvent was distilled off under reduced pressure and the residue was purified by silica gel column chromatography (hexane:ethyl acetate=9:1) to obtain Compound PR-1130 (hereinafter, the step described above for obtaining Compound PR-1130 is sometimes referred to as "synthetic step A")

Synthetic Step A

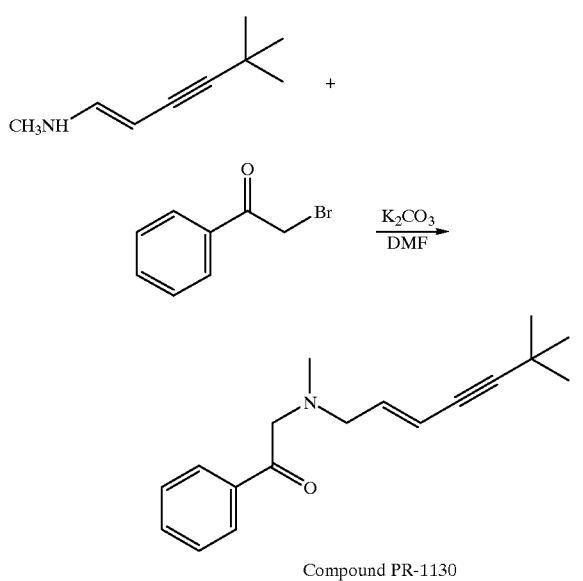

Compound PR-1130

The yield, % yield and NMR spectrum of Compound PR-1130 are as follows. Yield: 1.90 g, % yield: 32.2%.

$^1$H-NMR (CDCl$_3$, ppm) 1.24 (s, 9 H), 2.37 (s, 3 H), 3.21 (dd, J=6.89 Hz, 1.49 Hz, 2 H), 3.81 (s, 2 H), 5.66 (d, J=15.9 Hz, 1 H), 6.09 (d, t, J=15.9 Hz, 6.89 Hz, 1 H), 7.43~8.00 (m, 5 H)

0.51 g (1.89 mmol), of Compound PR-1130 was dissolved in 100 ml of diisopropyl ether (IPE), and 0.47 ml of 4N-hydrogen chloride- ethyl acetate was dropped while stirring at room temperature.

IPE (200 ml), was added and after 60 hours' stirring at room temperature, the crystals precipitated were collected by filtration, washed with IPE and dried under reduced pressure in a desiccator to obtain Compound PR-1254 as white crystals (this step corresponds to the step of hydrochlorination similar to Synthetic Step C described hereinbelow). Yield, % yield, melting point, NMR spectrum, and IR spectrum are as follows. Yield: 0.31 g, % yield: 53.6%, melting point: 160 to 162° C.

$^1$H-NMR (CDCl$_3$, ppm) 1.21 (s, 9 H), 3.04 (s, 3 H), 4.04 (d, J=7.56 Hz, 2 H), 4.5 7 (s, 2 H), 5.82 (d, J=15.9 Hz, 1 H), 6.31 (dt, J=15.9 Hz, 7.56 Hz, 1 H), 7.51~7.57 (m, 2 H), 7.69 (m, 1 H), 7.92 (m, 2 H) IR (KBr tablet, cm$^{-1}$): 3426, 2969, 2931, 1693, 1453, 1250, 969, 758

Example 2

Trans-N-(6,6-dimethyl-2-hepten-4-ynyl)-N-methyl-2-phenyl-2-propenylamine; (Compound PR-1257) and its hydrochloride; (Compound PR-1258)

Synthetic Method 2-1

Compound PR-1130 was obtained by Synthetic Step A shown in Example 1.

On the other hand, in 15 ml of tetrahydrofuran (THF), was suspended 1.75 g (4.90 mmol), of methyltriphenylphosphonium bromide and while stirring under nitrogen atmosphere at room temperature, 3.6 ml (5.94 mmol), of 1.65 M n-butyllithium-hexane solution was dropped and stirred at room temperature for 15 minutes.

This was cooled in an ice bath and a solution of 1.10 g (4.08 mmol), of Compound PR-1130 dissolved in 20 ml of THF was dropped. After dropping, stirring was continued for 1 hour in an ice bath and for 3 hours at room temperature, followed by pouring into ice water to stop the reaction.

The reaction mixture was extracted with 100 ml of diethyl ether and the organic extract was washed with a saturated aqueous sodium hydrogen carbonate solution and with saturated saline. After drying with anhydrous sodium sulfate, the solvent was distilled off under reduced pressure and the resulting residue was purified by silica gel column chromatography (hexane:ethyl acetate=9:1), to obtain Compound PR-1257 (hereinafter, the step of obtaining Compound PR-1257 from Compound PR-1130 is sometimes referred to as "Synthetic Step B"; Synthetic Step B is a step which utilizes Wittig reaction).

Synthetic Step B

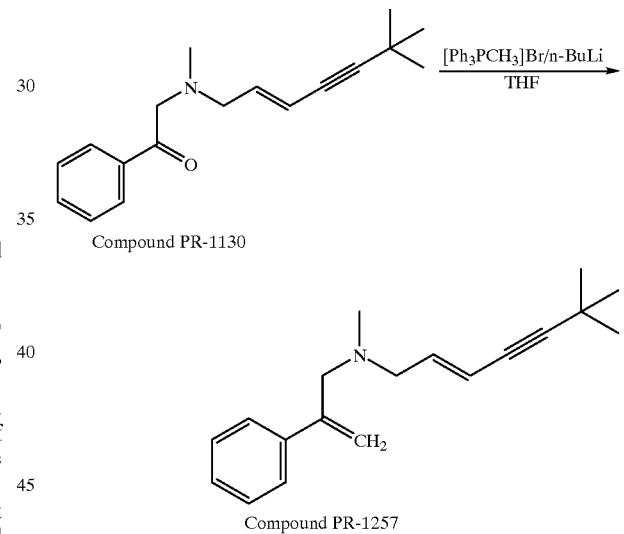

Compound PR-1130

Compound PR-1257

Yield, % yield and NMR spectrum of Compound PR-1257 are as follows. Yield: 0.39 g, % yield: 28.4%

$^1$H-NMR (CDCl$_3$, ppm) 1.24 (s, 9 H), 2.20 (s, 3 H), 3.05 (dd, J=1.08 Hz, 6.75 Hz, 2 H), 3.34 (s, 2 H), 5 24 (s, 1 H), 5.44 (s, 1 H), 5.61 (d, J=15.0 Hz, 1 H), 6.05 (dt, J=15.0 Hz, 6.75 Hz, 1 H) 7.29~7.50 (m, 5 H) 0.39 g (1.41 mmol), of Compound 1257 was dissolved in 100 ml of diisopropyl ether, and 0.32 ml of 4N-hydrogen chloride-ethyl acetate solution was dropped while stirring.

After dropping, 150 ml of IPE was added and stirring was continued at room temperature for 72 hours. Thereafter, crystals precipitated were collected by filtration. After washing with IPE, the crystals were dried in a desiccator under reduced pressure to obtain Compound PR-.1258 as white crystals (hereinafter, the step of obtaining, from Compound PR-1257, its hydrochloride, i.e., Compound PR-1258 is sometimes referred to as "Synthetic Step C").

Synthetic Step C

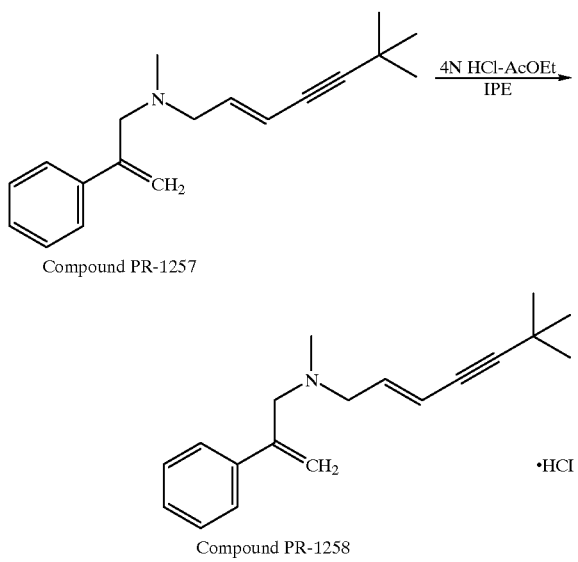

The yield, % yield, melting point, NMR spectrum and IR spectrum of Compound PR-1258 are as follows. Yield: 0.29 g, % yield: 65.4%, melting point: 183 to 185° C.

$^1$H-NMR (CDCl$_3$, ppm) 1.25 (s, 9 H), 2.58 (d, J=4.86 Hz, 3 H), 3.41~3.65 (m, 2 H), 4.00~4.15 (m, 2 H), 5.63 ( s, 1 H), 5.69 ( s, 1 H), 5.84 (d, J=8.91 Hz, 1 H), 6.23 (dt, J=15.7 Hz, 7.56 Hz, 1 H), 7.39~7.45 (m, 5 H), 12.8 (s, 1 H) IR (KBr tablet, cm$^{-1}$); 2971, 2930, 2906, 2690, 2672, 2632, 2570, 2502, 1465

Synthetic Method 2-2

N,N-Dimethylformamide (30 ml), was mixed with 3.36 g (22.2 mmol), of Compound PR-1133 and 4.19 g (30.3 mmol), of potassium carbonate and a solution of 3.88 g (19.7 mmol), of α-bromomethylstyrene (Compound PR-1392) obtained in Preparation Example 19 in 15 ml of DMF was dropped while stirring in an ice bath.

After dropping, the mixture was stirred for 12 hours at room temperature and the reaction mixture was poured in an ice water to stop the reaction. The reaction mixture was extracted with a mixed solvent containing 80 ml of diethyl ether and 20 ml of ethyl acetate, and the organic layer was washed with a saturated aqueous sodium hydrogen carbonate solution and with saturated saline and dried with anhydrous sodium sulfate.

The solvent was distilled off under reduced pressure and the residue was purified by silica gel column chromatography (hexane:ethyl acetate=20:1) to obtain Compound PR-1257. The yield, % yield and NMR are as follows. Yield: 2.76 g, % yield: 46.5%

$^1$H-NMR (CDCl$_3$, ppm) 11.24 (s, 9 H), 2.19 (s, 3 H), 3.05 (dd, J=1.35 Hz, 6.35 Hz, 2 H), 3.34 (s, 2 H), 5.23 (d, J=1.35 Hz, 1 H), 5.44 (s, J=1.35 Hz, 1 H), 5.61 (dt, J=15.7 Hz, 1.49 Hz, 1 H), 6.05 (dt, J=15.9 Hz, 6.48 Hz, 1 H), 7.23~7.50 (m, 5 H)

Example 3

Trans-2-[N-(6,6-dimethyl-2-hepten-4-ynyl)-N-methylamino]-2'-methylacetophenone (Compound PR-1531), trans-N-(6,6-dimethyl-2-hepten-4-ynyl)-N-methyl-[2-(o-tolyl)-2-propenyl]amine; (Compound PR-1532), and hydrochloride of Compound PR-1532 (Compound PR-1533)

In Synthetic Step A in Example 1,2-bromo-2'-methylacetophenone obtained in Preparation Example 6 was used instead of 2-bromoacetophenone, and otherwise the procedures in Synthetic Step A were followed to obtain Compound PR-1531. The yield, % yield, NMR spectrum of Compound PR-1531 are as follows. Yield: 1.74 g, % yield: 61.9%

$^1$H-NMR (CDCl$_3$, ppm) 1.24 (s, 9 H), 2.36 (s, 3 H), 2.49 (s, 3 H), 3.19 (dd, J=6.89 Hz, 1.35 Hz, 2 H), 3.73 (s, 2 H), 5.64 (d, J=15.9 Hz, 1 H), 6.06 (dt, J=15.9 Hz, 6.89 Hz, 1 H), 7.22~7.26 (m, 2 H), 7.36 (m, 1 H), 7.63 (m, 1 H), In Synthetic Step B in Example 2, Compound PR-1531 was used instead of Compound PR-1130 and, otherwise the procedures in Synthetic Step B were followed to obtain Compound PR-1532. The yield, % yield and NMR spectrum of Compound PR-1532 are as follows. Yield: 0.49 g, % yield: 28.4%

$^1$H-NMR (CDCl$_3$, ppm) 1.24 (s, 9 H), 2.24 (s, 3 H), 2.30 (s, 3 H), 3.05 (dd, J=6.49 Hz, 1.35 Hz, 2 H), 3.17 (s, 2 H), 5.04 (d, J=2.70 Hz, 1 H), 5.42 (d, J=2.16 Hz, 1 H), 5.58 (d, J=15.9 Hz, 1 H), 6.00 (dt, J=1 15.9 Hz, 6.49 Hz, 1 H), 7.08~7.36 (m, 4 H)

Further, in Synthetic Step C in Example 2, Compound PR-1532 was used instead of Compound PR-1257, and otherwise the procedures in Synthetic Step C were followed to obtain Compound PR-1533 as yellowish brown crystals. The yield, % yield, melting point, NMR spectrum, and IR spectrum of Compound PR-1533 are as follows. Yield: 0.13 g, % yield: 23.5%, melting point: 165 to 167° C.

$^1$H-NMR (CDCl$_3$, ppm) 1.23 (s, 9 H), 2.33 (s, 3 H), 2.63 (d J=4.59 Hz, 3 H), 3.44 (m, 2 H), 3.95 (s, 2 H), 5.44 (d, J=15.9 Hz, 1 H), 5.58 (s, 1 H), 5.98 (s, 1 H), 6.18 (dt, J=15.9 Hz, 7.29 Hz, 1 H), 7.13~7.31 (m 4 H), 12.8 (broad s, 1 H) IR (KBr tablet, cm$^{-1}$): 2967, 2636

Example 4

Trans-2-[N-(6,6-dimethyl-2-hepten-4-ynyl)-N-methylamino]-3'-methylacetophenone; (Compound PR-1538), trans-N-(6,6-dimethyl-2-hepten-4-ynyl)-N-methyl-[2-(m-tolyl)-2-propenyl]amine (Compound PR-1539), and hydrochloride of Compound PR-1539 (Compound PR-1540)

In Synthetic Step A in Example 1,2-bromo-3'-methylacetophenone obtained in Preparation Example 5 was used instead of 2-bromoacetophenone, and otherwise the procedures in Synthetic Step A were followed to obtain Compound PR-1538. The yield, % yield and NMR spectrum of Compound PR-1538 are as follows. Yield: 1.11 g, % yield: 39.5%

$^1$H-NMR (CDCl$_3$, ppm) 1.24 (s, 9 H), 2.37 (s, 3 H), 2.41 (s, 3 H), 3.21 (dd, J=7.02 Hz, 1.62 Hz, 2 H), 3.81 (s, 2 H), 5.66 (d J=15.9 Hz, 1 H), 6.10 (dt, J=15.9 Hz, 7.02 Hz, 1 H), 7.31~7.39 (m, 2 H), 7.76~7.78 (m, 2 H)

In Synthetic Step B in Example 2, Compound PR-1538 was used instead of Compound PR-1130 and otherwise the procedures in Synthetic Step B were followed to obtain Compound PR-1539. The yield, % yield and NMR spectrum of Compound PR-1539 are as follows. Yield: 0.31 g, % yield: 28.1%

$^1$H-NMR (CDCl$_3$, ppm) 1.24 (s, 9 H), 2.22 (s, 3 H), 2.36 (s, 3 H) 3.05 (dd, J=6.35 Hz, 1.35 Hz, 2 H), 3.32 (s, 2 H), 5.22 (s, 1 H), 5.41 (d, J=1.35 Hz, 1 H), 5.62 (d, J=15.9 Hz, 1 H), 6.05 (dt, J=15.9 Hz, 6.35 Hz, 1 H), 7.07~7.35 (m, 4 H)

Further, in Synthetic Step C in Example 2, Compound PR-1539 was used instead of Compound PR-1257, and otherwise the procedures in Synthetic Step C were followed to obtain Compound PR-1540 as pale yellow crystals. The yield, % yield, melting point, NMR spectrum and IR spectrum of Compound PR-1540 are as follows. Yield: 0.18 g, % yield: 51.5%, melting point: 145 to 147° C.

¹H-NMR (CDCl₃, ppm) 11.23 (s, 9 H), 2.39 (s, 3 H), 2.58 (d, J=5.13 Hz, 3 H), 3.38~3.67 (m, 2 H), 4.02~4.14 (m, 2 H), 5.62 (d, J=15.4 Hz, 1 H), 5.80 (s, 1 H×2 (=CH₂)), 6.23 (dt, J=15.4 Hz, 7.56 Hz, 1 H), 7.14~7.33 (m, 4 H), 12.7 (broad s, 1 H) IR (KBr tablet, cm⁻¹): 2970, 2927, 2969

Example 5

Trans-2-[N-(6,6-dimethyl-2-hepten-4-ynyl)-N-methylamino]-4'-methylacetophenone (Compound PR-1413), trans-N-(6,6-dimethyl-2-hepten-4ynyl)-N-methyl-[2-p-tolyl)-2-propenyl]amine (Compound PR-1414) and hydrochloride of Compound PR-1414 (Compound PR-1415)

In Synthetic Step A in Example 1, 2-bromo-4'-methylacetophenone obtained in Preparation Example 21 was used instead of 2-bromoacetophenone and triethylamine was used instead of potassium carbonate, and otherwise the procedures in Synthetic Step A were followed to obtain Compound PR-1413. The yield, % yield and NMR spectrum are as follows. Yield: 0.89 g, % yield: 31.4%

¹H-NMR (CDCl₃, ppm) 1.23 (s, 9 H), 2.36 (s, 3 H), 2.41 (s 33 H), 3.20 (dd, J=7.02 Hz, 1.08 Hz, 2 H), 3.79 (s, 2 H), 5.56 (d, J=15.66 Hz, 1 H), 6.09 (dt, J=15.66 Hz, 7.02 Hz, 1 H), 7.25 (d, J=8.37 Hz, 2 H), 7.89 (d, J=8.37 Hz, 2 H)

Further, in Synthetic Step B in Example 2, Compound PR-1413 was used instead of Compound PR-1130, and otherwise the procedures in Synthetic Step B were followed to obtain Compound PR-1414. The yield, % yield and NMR spectrum of Compound PR-1414 are as follows. Yield: 0.50 g, % yield: 56.6%

¹H-NMR (CDCl₃, ppm) 1.24 (s, 9 H), 2.18 (s, 3 H), 2.34 (s, 3 H), 3.04 (dd, J=6.48 Hz, 1.62 Hz, 2 H), 3.32 (s, 2 H), 5.18 (s, 2 H), 5.40 (s, 1 H), 5.61 (dt, J=15.93 Hz, 1.62 Hz, 1 H), 6.05 (dt, J=15.93 Hz, 6.48 Hz, 1 H), 7.13 (d, J=8.10 Hz, 2 H), 7.38 (d, J=8.10 Hz, 2 H)

Further, in Synthetic Step C in Example 2, Compound PR-1414 was used instead of Compound PR-1257 and otherwise the procedures in Synthetic Step C were followed to obtain Compound PR-1415 as crystals. The yield, % yield, melting point and NMR spectrum of Compound PR-1415 are as follows. Yield: 0.51 g, % yield: 90.3%, melting point: 169 to 170.5° C.

¹H-NMR (CDCl₃, ppm) 1.23 (s, 9 H), 2.37 (s, 3 H), 2.57 (d, J=4.05 Hz, 3 H), 3.33~3.68 (m, 2 H), 3.96~4.18 (m, 2 H), 5.67 (d, J=15.66 Hz, 1 H), 5.78 (s, 2 H), 6.23 (dt, J=15.66 Hz, 7.56 Hz, 1 H), 7.21 (d, J=8.10 Hz, 2 H), 7.27 (d, J=8.10 Hz, 2 H), 12.69 (broad, 1 H)

Example 6

Trans-2-[N-(6,6-dimethyl-2-hepten-4-ynyl)-N-methylamino]-2'-fluoacetophenone (Compound PR-1489) trans-N-(6,6'-dimethyl-2-hepten-4-ynyl)-N-methyl-[2-(2-fluorophenyl)-2-propenyl]amine (Compound PR-1490) and hydrochloride of Compound PR-1490 (Compound PR-1491)

In Synthetic Step A in Example 1,2-bromo-2'-fluoroacetophenone obtained in Preparation Example 2 was used instead of 2-bromoacetophenone, and otherwise the procedures in Synthetic Step A were followed to obtain Compound PR-1489. The yield, % yield and NMR spectrum of Compound PR-1489 are as follows. Yield: 0.58 g, % yield: 30.5%

¹H-NMR (CDCl₃, ppm) 1.23 (s, 9 H), 2.39 (s, 3 H), 3.22 (d, J=7.02 Hz, 2 H), 3.81 (d, J=2.97 Hz, 2 H), 5.63 (d, J=15.9 Hz, 1 H), 6.05 (dt, J=15.9 Hz, 7.02 Hz, 1 H), 7.09~7.26 (m, 2 H), 7.53 (m, 1 H), 7.87 (m, 1 H)

Further, in Synthetic Step B in Example 2, Compound PR-1489 was used instead of Compound PR-1130 and otherwise the procedures in Synthetic Step B were followed to obtain Compound PR-1490. The yield, % yield and NMR spectrum of Compound PR-1490 are as follows. Yield: 0.14 g, % yield: 24.3%

¹H-NMR (CDCl₃, ppm) 1.23 (s, 9 H), 2.18 (s, 3 H), 3.02 (d, J=6.21 Hz, 2 H), 3.34 (s, 2 H), 5.34 (s, 1 H), 5.43 (s, 1 H), 5.57 (d, J=15.9 Hz, 1 H), 5.98 (dt, J=15.9 Hz, 6.21 Hz, 1 H), 7.02~7.34 (m, 4 H)

Further, in Synthetic Step C in Example 2, Compound PR-1490 was used instead of Compound PR-1257 and otherwise the procedures in Synthetic Step C were followed to obtain Compound PR-1491 as white crystals. The yield, % yield, melting point, NMR spectrum, and IR spectrum of Compound PR-1491 are as follows. Yield: 0.09 g, % yield: 56.9%, melting point: 165 to 169° C.

¹H-NMR (CDCl₃, ppm) 1.23 (s, 9 H), 2.64 (d, J=4.32 Hz, 3 H), 3.50~ 3.64 (m, 2 H), 3.95~4.16 (m, 2 H), 5.67 (d, J=15.7 Hz, 1 H), 5.79 (s, 1 H), 6.09 (s, 1 H), 6.22 (dt, J=15.7 Hz, 2.16 Hz, 1 H), 7.09~7.39 (m, 4 H) IR (KBr tablet cm⁻¹): 2971, 2590, 2569, 2537, 2513, 2481, 1489, 1453, 1412, 768

Example 7

Trans-2-[N-(6,6-dimethyl-2-hepten-4-ynyl)-N-methylamino]-3'-fluoroacetophenone (Compound PR-1468), trans-N-(6,6-dimethyl-2-hepten-4-ynyl)-N-methyl-[2-(3-fluorophenyl)-2-propenyl]amine (Compound PR-1469), and hydrochloride of Compound PR-1469 (Compound PR-1470)

In Synthetic Step A in Example 1, 2-bromo-3'-fluoroacetophenone obtained in Preparation Example 22 was used instead of 2-bromoacetophenone and triethylamine was used instead of potassium carbonate, and otherwise the procedures in Synthetic Step A were followed to obtain Compound PR-1531. The yield, % yield and NMR spectrum of Compound PR-1468 are as follows. Yield: 1.06 g, % yield: 46.1%

¹H-NMR (CDCl₃, ppm) 1.25 (s, 9 H), 2.36 (s, 3 H), 3.19 (dd, J=6.75 Hz, 1.08 Hz, 2 H), 3.77 (s, 2 H), 5.65 (dt, J=15.93 Hz, 1.08 Hz, 1 H), 6.07 (dt, J=15.93 Hz, 6.75 Hz, 1 H), 7.27 (m, 1 H), 7.44 (m, 1 H), 7.69 (m, 1 H), 7.78 (m, 1 H)

Further, in Synthetic Step B in Example 2, Compound PR-1468 was used instead of Compound PR-1130 and otherwise the procedures in Synthetic Step B were followed to obtain Compound PR-1469. The yield, % yield and NMR spectrum of Compound PR-1469 are as follows. Yield: 0.60 g, % yield: 57.0%

¹H-NMR (CDCl₃, ppm) 1.24 (s, 9 H), 2.19 (s, 3 H), 3.04 (dd, J=6.48 Hz 1.62 Hz, 1 H), 3.31 (s, 2 H), 5.62 (s, 1 H), 5.46 (s, 1 H), 5.61 (dt, J=15.66 Hz, 1.62 Hz, 1 H), 6.04 (dt, J=15.66 Hz, 6.48 Hz, 1 H), 6.96 (m, 1 H), 7.18~7.38 (m, 3 H)

Further, in Synthetic Step C in Example 2, Compound PR-1469 was used instead of Compound PR-1257 and otherwise the procedures in Synthetic Step C were followed to obtain Compound PR-1470. The yield, % yield, melting point and NMR spectrum of Compound PR-1470 are as follows. Yield: 0.61 g, % yield: 90.1%, melting point: 174 to 175.5° C.

¹H-NMR (CDCl₃, ppm) 1.23 (s, 9 H), 2.61 (d, 3 H), J=4.59 Hz), 3.43~3.73 (m, 2 H), 3.98 (dd, J=13.77 Hz, 4.32 Hz, 1 H), 4.13 (dd, J=13.77 Hz, 2.97 Hz, 1 H), 5.71 (d, J=15.93 Hz, 1 H), 5.88 (s, 1 H), 5.96 (s 1 H), 6.22 (dt, J=15.93 Hz, 7.56 Hz, 1 H), 7.03~7.14 (m 2 H), 7.18 (d, J=7.83 Hz, 1 H), 7.40 (m, 1 H), 12.82 (broad, 1 H)

Example 8

Trans-2-[N-(6,6-dimethyl-2-hepten-4-ynyl)-N-methylamino]-4'-fluoroacetophenone (Compound PR-1428), trans-N-(6,6-dimethyl-2-hepten-4-ynyl)-N-methyl-[2-(4-fluorophenyl)-2-propenyl]amine: (Compound PR-1429), and hydrochloride of Compound PR-1429 (Compound PR-1430)

In Synthetic Step A in Example 1,2-bromo-4'-fluorolacetophenone obtained in Preparation Example 1 was used instead of 2-bromoacetophenone and otherwise the procedures in Synthetic Step A were followed to obtain Compound PR-1428. The yield, % yield and NMR spectrum of Compound PR-1428 are as follows. Yield: 0.65 g, % yield: 34.2%

$^1$H-NMR (CDCl$_3$, ppm) 1.23 (s, 9 H), 2.35 (s, 3 H), 3.19 (dd, J=6.75 Hz, 1.35 Hz, 2 H), 3.76 (s, 2 H), 5.65 (dd, J=15.7 Hz, 1.35 Hz, 1 H), 6.09 (dt, J=15.7 Hz, 6.75 Hz, 1 H), 7.07~7.13 (m, 2 H), 8.01~8.08 (m, 2 )

Further, in Synthetic Step B in Example 2, Compound PR-1428 was used instead of Compound PR-1130 and otherwise the procedures in Synthetic Step B were followed to obtain Compound PR-1429. The yield, % yield and NMR spectrum of Compound PR-1429 are as follows. Yield: 0.27 g, % yield: 41.9%

$^1$H-NMR (CDCl$_3$, ppm) 1.24 (s, 9 H), 2.18 (s, 3 H), 3.03 (dd, J=16.48 Hz, 1.62 Hz, 2 H), 3.30 (s, 2 H), 5.20 (d, J=0.81 Hz, 1 H), 5.38 (d, J=0.81 Hz, 1 H) 5.61 (dt, J=15.7 Hz, 1.62 Hz, 1 H), 6.03 (dt, J=15.7 Hz, 6.48 Hz, 1 H), 6.96~7.03 (m 2 H), 7.43~7.50 (m, 2 H)

Further, in Synthetic Step C in Example 2, Compound PR-1429 was used instead of Compound PR-1257 and otherwise the procedures in Synthetic Step C were followed to obtain Compound PR-1430 as white crystals. The yield, % yield, melting point, NMR spectrum and IR spectrum of Compound PR-1430 are as follows. Yield: 0.14 g, % yield: 45.8%, melting point: 194 to 196° C.

$^1$H-NMR (CDCl$_3$, ppm) 1.23 (s,9 H), 2.60 (d, 3 H, J=4.05 Hz), 3.49~3.65 (m, 2 H), 3.95~4.14 (m, 2 H), 5.67 (s, 1 H), 5.73 (s, 1 H), 5.82 (d, J=16.7 Hz, 1 H), 6.22 (dt, J=16.7 Hz, 7.56Hz), 7.08~7.16 (m, 2 H), 7.36~7.41 (m, 2 H), 12.8 (broad s, 1 H ) IR (KBr tablet, cm$^{-1}$): 2972, 2956, 2692, 2637, 1511, 1234, 1225, 841

Example 9

Trans-2'-bromo-2-[N-(6,6-dimethyl-2-hepten-4-ynyl)-N-methylamino]acetophenone (Compound PR-1503), trans-N-(6,6-dimethyl-2-hepten-4-ynyl)-N-methyl-[2-(2-bromophenyl)-2-propenyl]amine (Compound PR-1504) and hydrochloride of Compound PR-1504 (Compound PR-1505)

In Synthetic Step A in Example 1,2,2'-dibromoacetophenone obtained in Preparation Example 3 was used instead of 2-bromoacetophenone and otherwise the procedures in Synthetic Step A were followed to obtain Compound PR-1503. The yield, % yield, and NMR spectrum of Compound PR-1503 are as follows. Yield: 1.91 g, % yield: 55.3%

$^1$H-NMR (CDCl$_3$, ppm) 1.24 (s 9 H), 2.39 (s, 3 H), 3.20 (dd, J=6.48 Hz, 1.62 Hz, 2 H), 3.74 (s, 2 H), 5.62 (d, J=15.9 Hz, 1 H), 6.02 (dt, J=15.9 Hz, 6.8 Hz, 1 H), 7.26~7.61 (m, 4 H)

Further, in Synthetic Step B in Example 2, Compound PR-1503 was used instead of Compound PR-1130 and otherwise the procedures in Synthetic Step B were followed to obtain Compound PR-1504. The yield, % yield and NMR spectrum of Compound PR-1504 are as follows. Yield: 0.30 g, % yield: 15.8%

$^1$H-NMR (CDCl$_3$, ppm) 1.22 (s, 9 H), 2.24 (s, 3 H), 3.06 (dd, J=1.62 Hz, 6.48 Hz, 2 H), 3.29 (s, 2 H), 5.15 (s, 1 H), 5.47 (d, J=1.89 Hz, 1 H), 5.57 (d, J=15.9 Hz, 1 H), 5.99 (dt, J=15.9 Hz, 6.48 Hz, 1 H), 7.09~7.57 (m, 4 H)

Further, in Synthetic Step C in Example 2, Compound PR-1504 was used instead of Compound PR-1257 and otherwise the procedures in Synthetic Step C were followed to obtain Compound PR-1505 as yellowish brown crystals. The yield, % yield, melting point, NMR spectrum, and IR spectrum of Compound PR-1505 are as follows. Yield: 0.24 g, % yield: 72.4%, melting point: 127 to 132° C.

$^1$H-NMR (CDCl$_3$, ppm) 1.23 (s, 9 H), 2.68 (d, J=4.86 Hz, 3 H), 3.49~3.66 (m, 2 H), 3.93~4.08 (m, 2 H), 5.59 (d, J=15.9 Hz, 1 H), 5.71 (d, J=1.89 Hz, 1 H), 6.12 (s, 1 H), 6.21 (dt, J=15.9 Hz, 7.02 Hz, 1 H), 7.22~7.65 (m, 4 H), 12.7 (broad s, 1 H) IR (KBr tablet, cm$^{-1}$): 2969, 2628, 2612, 2499, 1471

Example 10

Trans-3'-bromo-2-[N-(6,6-dimethyl-2-hepten-4-ynyl)-N-methylamino]acetophenone (Compound PR-1482), trans-N-(6,6-dimethyl-2-hepten-4-ynyl)-N-meth yl-[2-(3-bromophenyl)-2-propenyl]amine (Compound PR-1483), and hydrochloride of Compound PR-1483; (Compound PR-1484)

In Synthetic Step A in Example 1,2',3'-dibromoacetophenone obtained in Preparation Example 4 was used instead of 2-bromoacetophenone and otherwise the procedures in Synthetic Step A were followed to obtain Compound PR-1482. The yield, % yield and NMR spectrum of Compound PR-1482 are as follows. Yield: 1.20 g, % yield: 43.4%

$^1$H-NMR (CDCl$_3$, ppm) 1.26 (s 9 H), 2.35 (s, 3 H), 3.19 (dd, J=1.35 Hz, 6.75 Hz, 2 H), 3.76 (s, 2 H), 5.65 (dd, J=15.8 Hz, 1.35 Hz, 1 H), 6.07 (dt, J=15.8 Hz, 6.75 Hz), 7.34 (t, J=7.83 Hz, 1 H), 7.69 (m, 1 H), 7.92 (m, 1 H), 8.13 (m, 1 H)

Further, in Synthetic Step B in Example 2, Compound PR-1482 was used instead of Compound PR-1130 and otherwise the procedures in Synthetic Step B were followed to obtain Compound PR-1483. The yield, % yield and NMR spectrum of Compound PR-1483 are as follows. Yield: 0.82 g, % yield: 68.6%

$^1$H-NMR (CDCl$_3$, ppm) 1.24 (s, 9 H), 2.18 (s, 3 H), 3.04 (dd, J=1.35 Hz, 6.75 Hz, 2 H), 3.29 (s, 2 H), 5.26 (d, J=1.35 Hz, 1 H), 5.44 (d, J=1.35 Hz, 1 H), 5.62 (dt, J=15.7 Hz, 1.35 Hz, 1 H), 6.35 (dt, J=15.7 Hz, 1.35 Hz, 1 H), 7.18 (t, J=7.83 Hz, 1 H), 7.33~7.43 (m, 2 H), 7.63 (t, J=1.89 Hz, 1 H)

Further, in Synthetic Step C in Example 2, Compound PR-1483 was used instead of Compound PR-1257 and otherwise the procedures in Synthetic Step C were followed to obtain Compound PR-1484 as white crystals. The yield, % yield, melting point, NMR spectrum and IR spectrum of Compound PR-1484 are as follows. Yield: 0.70 g, % yield: 77.2%, melting point: 169 to 171° C.

$^1$H-NMR (CDCl$_3$, ppm) 1.24 (s, 9 H), 2.61 (d, J=4.32 Hz, 3 H), 3.49~3.66 (m, 2 H), 3.93~4.14 (m, 2 H), 5.70 (d, J=15.9 Hz, 1 H), 5.86 (s, 1 H), 5.96 (s, 1 H), 6.23 (dt, J=15.9 Hz, 7.29 Hz, 1 H), 7.30~7.54 (m, 4 H), 12.9 (broad s, 1 H) IR (KBr tablet, cm$^{-1}$): 2970, 2487

Example 11 trans-4'-bromo-2-[N-(6,6-dimethyl-2-hepten-4-ynyl)-N-methylamino]acetophenone (Compound PR-1437), trans-N-(6,6-dimethyl-2-hepten-4-ynyl)-N-methyl-[2-(4-bromophenyl)-2-propenyl]amine (Compound PR-1438), and hydrochloride of Compound PR-1438; (Compound PR-1439)

In Synthetic Step A in Example 1,2,4'-dibromoacetophenone (manufactured by Aldrich Company)

was used instead of 2-bromoacetophenone and otherwise the procedures in Synthetic Step A were followed to obtain Compound PR-1437. The yield, % yield and NMR spectrum of Compound PR-1437 are as follows. Yield: 0.92 g, % yield: 40.0%

$^1$H-NMR (CDCl$_3$, ppm) 11.23 (s, 9 H), 2.36 (s, 3 H), 3.21 (d, 2 H, J=6.75Hz), 3.77 (s, 2 H), 5.65 (d, J=15.9 Hz, 1 H), 6.06 (dt, 1 H, J=15.9 Hz, 6.75 Hz), 7.60 (d, J=6.75 Hz, 2 H), 7.87 (d, J=6.75 Hz, 2 H)

Further, in Synthetic Step B in Example 2, Compound PR-1437 was used instead of Compound PR-1130 and otherwise the procedures in Synthetic Step B were followed to obtain Compound PR-1438. The yield, % yield and NMR spectrum of Compound PR-1438 are as follows. Yield: 0.32 g, % yield: 35.0%

$^1$H-NMR (CDCl$_3$, ppm) 1.24 (s, 9 H), 2.13 (s, 3 H), 3.02 (dd, J=6.48 Hz, 1.35 Hz, 2 H), 3.30 (s, 3 H), 5.23 (d, J=0.81 Hz, 1 H), 5.43 (d, J=0.81 Hz, 1 H), 5.60 (dt, J=15.7 Hz, 1.49 Hz, 1 H), 6.01 (dt, J=15.7 Hz, 6.48 Hz, 1 H), 7.35 (d, J=8.37 Hz, 2 H), 7.44 (d, J=8.37 Hz, 2 H)

Further, in Synthetic Step C in Example 2, Compound PR-1438 was used instead of Compound PR-1257 and otherwise the procedures in Synthetic Step C were followed to obtain Compound PR-1439 as white crystals. The yield, % yield, melting point, NMR spectrum and IR spectrum of Compound PR-1439 are as follows. Yield: 0.30 g, % yield: 84.8%, melting point: 174.3 to 178.3° C.

1.22 (s, 9 H), 2.58 (s, 3 H), 3.42~3.65 (m, 2 H), 3.98~4.12 (m, 2 H), 5.70 (d, J=15.7 Hz, 1 H), 5.83~5.91 (m, 2 H), 6.12 (m, 1 H), 7.24~7.57 (m, 4 H) IR (KBr tablet, cm$^{-1}$): 2969, 2631, 1467, 1395, 1070, 964, 932, 831

Example 12

Trans-2'-chloro-2-[N-(6,6-dimethylhepten-4-ynyl)-N-methylamino]acetophenone (Compound PR-1496), trans-N-(6,6-dimethyl-2-hepten-4-ynyl)-N-methyl-[2-(2-chlorophenyl)-2-propenyl]amine (Compound PR-1497), and hydrochloride of Compound PR-1497; (Compound PR-1498)

In Synthetic Step A in Example 1, 2-bromo-2'-chloroacetophenone obtained in Preparation Example 23 was used instead of 2-bromoacetophenone and otherwise the procedures in Synthetic Step A were followed to obtain Compound PR-1496. The yield, % yield and NMR spectrum of Compound PR-1496 are as follows. Yield: 1.08 g, % yield: 35.6%

$^1$H-NMR (CDCl$_3$, ppm) 1.24 (s, 9 H), 2.37 (s 3 H), 3.19 (dd, J=6.75 Hz, 1.35 Hz, 2 H), 3.76 (s, 2 H), 5.61 (dt, J=15.66 Hz, 1.35 Hz, 1 H), 6.01 (dt, J=15.66 Hz, 6.75 Hz, 1 H), 7.25~7.48 (m, 4 H)

Further, in Synthetic Step B in Example 2, Compound PR-1496 was used instead of Compound PR-1130 and otherwise the procedures in Synthetic Step B were followed to obtain Compound PR-1469. The yield, % yield and NMR spectrum of Compound PR-1497 are as follows. Yield: 0.49 g, % yield: 45.7%

$^1$H-NMR (CDCl$_3$, ppm) 1.23 (s 9 H ), 2.22 (, 3 H), 3.04 (dd, J=6.48 Hz, 1.62 Hz, 2 H), 3.31 (s, 2 H), 5.17 (s, 1 H), 5.46 (s, 1 H), 5.56 ( dt, J=15.93 Hz, 1.62 Hz, 1 H), 5.98 (dt, J=15.93 Hz, 6.48 Hz, 1 H), 7.21 (m, 3 H), 7.35 (m, 1 H)

Further, in Synthetic Step C in Example 2, Compound PR-1497 was used instead of Compound PR-1257 and otherwise the procedures in Synthetic Step C were followed to obtain Compound PR-1498 as crystals. The yield, % yield, melting point, and NMR spectrum of Compound PR-1498 are as follows. Yield: 0.45 g, % yield: 81.9%, melting point: 157 to 159° C.

$^1$H-NMR (CDCl$_3$, ppm) 1.23 (s, 9 H), 2.67 (d, J=5.13 Hz, 3 H), 3.42~3.70 (m, 2 H), 4.01 (dd, J=14.31 Hz, 4.32 Hz, 1 H), 4.10 (dd, J=14.31 Hz, 3.51 Hz, 1 H), 5.60 (d, J=15.93 Hz, 1 H), 5.71 (s, 1 H), 6.13 (s, 1 H), 6.21 (dt, J=15.93 Hz, 7.56 Hz, 1 H), 7.28~7.37 (m, 3 H), 7.45 (dd, J=8.64 Hz, 3.78 Hz, 1 H), 12.81 (broad, 1 H)

Example 13

Trans-4'-chloro-2-[N-(6,6-dimethyl-2-hepten-4-ynyl)-N-methylamino]acetophenone (Compound PR-1416),trans-N-(6,6-dimethyl-2-hepten-4-ynyl)-N-methyl-[2-(4-chlorophenyl)-2-propenyl]amine (Compound PR-1417), and hydrochloride of Compound PR-1417 (Compound PR-1418)

In Synthetic Step A in Example 1,2-bromo-4'-chloroacetophenone obtained in Preparation Example 6 was used instead of 2-bromoacetophenone and otherwise the procedures in Synthetic Step A were followed to obtain Compound PR-1416. The yield, % yield and NMR spectrum of Compound PR-1416 are as follows. Yield: 1.80 g, % yield: 59.7%

$^1$H-NMR (CDCl$_3$, ppm) 1.24 (s, 9 H), 2.35 (s, 3 H), 3.19 (dd, J=7.02 Hz, 1.35 Hz, 2 H), 3.75 (s, 2 H), 5.65 (dd, J=15.7 Hz, 1.35 Hz, 1 H), 6.21 (dt, J=15.9 Hz, 7.02 Hz, 1 H), 7.43 (d, J=8.91 Hz, 2 H), 7.95 (d, J=8.91 Hz, 2 H)

Further, in Synthetic Step B in Example 2, Compound PR-1416 was used instead of Compound PR-1130 and otherwise the procedures in Synthetic Step B were followed to obtain Compound PR-1417. The yield, % yield and NMR spectrum of Compound PR-1417 are as follows.

Yield: 0.89 g, % yield: 49.8%

$^1$H-NMR (CDCl$_3$, ppm) 1.24 (s, 9 H), 2.17 (s, 3 H), 3.03 (dd, J=6.48 Hz, 1.62 Hz, 2 H), 3.31 (s, 2 H), 5.23 (s, 1 H), 5.43 (s, 1 H), 5.61 (d J=15.9 Hz, 1 H), 6.02 (dt, J=15.9 Hz, 6.48 Hz, 1 H), 7.26~7.44 (m, 4 H)

Further, in Synthetic Step C in Example 2, Compound PR-1417 was used instead of Compound PR-1257 and otherwise the procedures in Synthetic Step C were followed to obtain Compound PR-1418 as white crystals. The yield, % yield, melting point, NMR spectrum and IR spectrum of Compound PR-1418 are as follows. Yield: 0.62 g, % yield: 62.1%, melting point: 180.0 to 182.5° C.

$^1$H-NMR (CDCl$_3$, ppm) 1.19 (s, 9 H), 2.60 (d, J=4.86 Hz, 3 H), 3.48~3.66 (m, 2 H), 3.94~4.10 (m, 2 H), 5.66 (s, 1 H), 5.73 (s, 1 H), 5.88 (d, J=15.4 Hz, 1 H), 6.21 (dt, J=15.4 Hz, 7.29 Hz, 1 H) 7.33 (d, J=3.65Hz, 2 H), 7.40 (d, J=3.65 Hz, 2 H) IR (KBr tablet, cm$^{-1}$): 2970, 2629, 2502, 1493, 1467, 1396, 964, 835

Example 14

Trans-2-[N-(6,6-dimethyl-2-hepten-4-ynyl)-N-methylamino]-2'-methoxyacetophenone (Compound PR-1632), trans-N-(6,6-dimethyl-2-hepten-4-ynyl)-N-methyl-[2-(2-methoxyphenyl)-2-propenyl]amine (Compound PR-1633), and hydrochloride of Compound PR-1633 (Compound PR-1634)

In Synthetic Step A in Example 1, 2-bromo-2'-methoxyacetophenone obtained in Preparation Example 7 was used instead of 2-bromoacetophenone and sodium carbonate was used instead of potassium carbonate, and otherwise the procedures in Synthetic Step A were followed to obtain Compound PR-1632. The yield, % yield and NMR spectrum of Compound PR-1632 are as follows. Yield: 0.65 g, % yield: 14.8%

$^1$H-NMR (CDCl$_3$, ppm) 1.24 (s, 9 H), 3.56 (s, 3 H), 3.20 (dd, J=6.89Hz, 1.49 Hz, 2 H), 3.82 (s, 2 H), 3.91 (s, 3 H), 5.61 (dd, J=15.9 Hz, 1.49 Hz, 1 H), 6.06 (dt, J=15.9 Hz, 6.89 Hz, 1 H), 6.94~7.03 (m, 2 H), 7.46 (m, 1 H), 7.70 (m, 1 H)

Further, in Synthetic Step B in Example 2, Compound PR-1632 was used instead of Compound PR-1130 and otherwise the procedures in Synthetic Step B were followed to obtain Compound PR-1633. The yield, % yield and NMR spectrum Compound PR-1633 are as follows. Yield: 0.17,% yield: 30.6%

$^1$H-NMR (CDCl$_3$, ppm) 1.21 (s, 9 H), 2.16 (s, 3 H), 2.99 (dd, J=6.48 Hz, 1.62 Hz, 2 H), 3.3 6 (s. 2 H), 3.83 (s, 3 H), 5.16 (d, J=2.43 Hz, 1 H), 5.32 (d, J=2.43 Hz, 1 H), 5.53 (dt, J=15.9 Hz, 1.62 Hz, 1 H), 5.96 (dt, J=15.9 Hz, 6.48 Hz, 1 H), 6.85~6.94 (m, 2 H), 7.15~7.28 (m, 2 H)

Further, in Synthetic Step C in Example 2, Compound PR-1633 was used instead of Compound PR-1257 and otherwise the procedures in Synthetic Step C were followed to obtain Compound PR-1634 as white crystals. The yield, % yield, melting point, NMR spectrum and IR spectrum of Compound PR-1634 are as follows. Yield: 0.17 g, % yield: 89.2%, melting point: 148 to 150° C.

$^1$H-NMR (CDCl$_3$, ppm) 1.23 (s, 9 H), 2.61 (d, J=4.86 Hz, 3 H), 3.45~3.47 (m, 2 H), 3.87 (s, 3 H), 4.13 (d, J=3.78 Hz, 2 H), 5.46 (d, J=15.9 Hz, 1 H), 5.61 (s, 1 H), 5.79 (s, 1 H), 6.21 (dt, J=15.9 Hz, 7.29 Hz, 1 H), 6.91~7.02 (m, 2 H), 7.18~7.40 (m, 2 H ), 12.5 (broad s, 1 H) IR (KBr tablet, cm$^{-1}$): 2966, 2933, 1459, 1256, 757

Example 15

Trans-2-[N-(6,6-dimethyl-2-hepten-4-ynyl)-N-methylamino]-3'-methoxyacetophenone (Compound PR-1388), trans-N-(6,6-dimethyl-2-hepten-4-ynyl)-N-methyl-(2-(3-methoxyphenyl)-2-propenyl]amine (Compound PR-1389), and hydrochloride of Compound PR-1389; (Compound PR-1390)

In Synthetic Step A in Example 1, 2-bromo-3'-methoxyacetophenone (manufacutred by Aldrich Company) was used instead of 2-bromoacetophenone and triethylamine was used instead of potassium carbonate, and otherwise the procedures in Synthetic Step A were followed to obtain Compound PR-1388. The yield, % yield and NMR spectrum of Compound PR-1388 are as follows. Yield: 2.58 g, % yield: 65.1%

$^1$H-NMR (CDCl$_3$, ppm) 1.23 (s, 9 H), 2.37 (s, 3 H), 3.21 (dd, J=6.75 Hz, 1.35 Hz, 1 H), 3.80 (s, 2 H), 3.8 6 (s, 3 H), 5.66 (dt, J=15.66 Hz, 1.35 Hz, 1 H), 6.09 (dt, J=15.66 Hz, 6.75 Hz, 1 H), 7.11 (ddd, J=7.83, 1.62 Hz, 1.08 Hz, 1 H), 7.36 (t, J=7.83 Hz, 1 H), 7.51 (dd, J=2.43 Hz, 1.62 Hz, 1 H), 7.57 (ddd, J=7.83 Hz, 2.43 Hz, 1.08 Hz, 1 H)

Further, in Synthetic Step B in Example 2, Compound PR-1388 was used instead of compound PR-1130 and otherwise the procedures in Synthetic Step B were followed to obtain Compound PR-1389. The yield, % yield and NMR spectrum of Compound PR-1389 are as follows. Yield: 0.44 g, % yield: 17.2%

$^1$H-NMR (CDCl$_3$, ppm) 1.24 ( s, 9 H), 2.20 (s, 3 H), 3.05 (dd, J=6.48 Hz, 1.35 Hz), 3.31 ( s, 2 H), 3.83 ( s, 3 H), 5.23 ( s, 1 H), 5.44 ( s, 1 H), 5.62 (dt, J=15.93 Hz, 1.35 Hz, 1 H), 96.0 (dt, J=15.93 Hz, 6.48 Hz, 1 H), 6.82 (ddd, J=7.83 Hz, 1.62 Hz, 1.08 Hz, 1 H), 7.03~7.10 (m, 2 H), 7.24 (t, J=7.83 Hz)

Further, in Synthetic Step C in Example 2, Compound PR-1389 was used instead of Compound PR-1257 and otherwise the procedures in Synthetic Step C were followed to obtain Compound PR-1390 as crystals. The yield, % yield, melting point, NMR spectrum of Compound PR-1390 are as follows. Yield: 0.44 g, % yield: 89.1%, melting point: 142 to 144° C.

$^1$H-NMR (CDCl$_3$, ppm) 1.23 (s, 9 H), 2.59 (d, J=5.13 Hz, 3 H), 3.45 (m, 1 H), 3.61 (m, 1 H), 3.85 (s, 3 H), 3.96~4.16 (m, 2 H), 5.66 (d, J=15.93 Hz, 1 H), 5.83 (s, 1 H), 5.85 (s, 1 H), 6.23 (dt, J=15.93 Hz, 7.56 Hz, 1 H), 6.86~6.98 (m, 3 H), 7.33 (t, J=7.83 Hz, 1 H), 12.75 (broad, 1 H)

Example 16

Trans-2-[N-(6,6-dimethyl-2-hepten-4-ynyl)-N-methylamino]-2'-nitroacetophenone (Compound PR-1639), trans-N-( 6,6-dimethyl-2-hepten-4-ynyl)-N-methyl-[2-(2-nitrophenyl)-2-propenyl]amine (Compound PR-1640), and hydrochloride of Compound PR-1640; (Compound PR-1641U In Synthetic Step A in Example 1, 2-bromo-2'-nitroacetophenone was used instead of 2-bromoacetophenone and otherwise the procedures in Synthetic Step A were followed to obtain Compound PR-1639.

Further, in Synthetic Step B in Example 2, Compound PR-1639 was used instead of Compound PR-1130 and sodium carbonate was used instead of potassium carbonate, and otherwise the procedures in Synthetic Step B were followed to obtain Compound PR-1640. The yield, % yield and NMR spectrum of Compound PR-1640 are as follows. Yield: 0.43 9,% yield: 10.6%

$^1$H-NMR (CDCl$_3$, ppm) 1.23 (s, 9 H), 2.16 (s 3 H), 2.98 (dd, J=6.35 Hz, 1.49 Hz, 2 H), 3.24 (s, 2 H), 5.18 (d, J=0.81 Hz, 1 H), 5.38 (d, J=0.81 Hz, 1 H) 5.53 (dt, J=15.9 Hz, 1.49 Hz, 1 H), 5.90 (dt, J=15.9 Hz, 6.35 Hz, 1 H), 7.33~7.44 (m, 2 H), 7.54 (m, 1 H), 7.86 (m, 1 H)

Further, in Synthetic Step C in Example 2, Compound PR-1640 was used instead of Compound PR-1257 and otherwise the procedures in Synthetic Step C were followed to obtain Compound PR-1641 as pale brown crystals. The yield, % yield, melting point, NMR spectrum and IR spectrum of Compound PR-1641 are as follows. Yield: 0.09 g, % yield: 90.0%, melting point: 162 to 163° C.

$^1$H-NMR (CDCl$_3$, ppm) 1.19 (s, 9 H), 2.78 (s, 3 H), 3.72~4.06 (m, —CH$_2$—X$_2$), 5.60 (s 1 H), 5.73 (d J=15.9 Hz, 1 H), 6.23 (dt, J=15.9 Hz, 7.29 Hz, 1 H) 7.48 ~7.60 (m, 2 H), 7.70 (m, 1 H), 8.07 (m, 1 H), 12.9 (broad s, 1 H) IR (KBr tablet, cm$^{-1}$): 3448, 3426, 2968, 2927, 2866 2687 2664 2632, 2657, 2655, 2495, 1527, 1465, 1408, 1343, 969, 764

Example 17

Trans-2-[N-(6,6-dimethyl-2-hepten-4-ynyl)-N-methylamino]-3'-nitroacetophenone (Compound PR-1646), trans-N-(6,6-dimethyl-2-hepten-4-ynyl)-N-methyl-[2-(3-nitrophenyl)-2-propenyl]amine (Compound PR-1647), and hydrochloride of Compound PR-1647 (Compound PR-1648)

In Synthetic Step A in Example 1, 2-bromo-3'-nitroacetophenone obtained in Preparation Example 9 was used instead of 2-bromoacetophenone and sodium carbonate was used instead of potassium carbonate, and otherwise the procedures in Synthetic Step A were followed to obtain Compound PR-1646.

Further, in Synthetic Step B in Example 2, Compound PR-1646 was used instead of Compound PR-1130 and otherwise the procedures in Synthetic Step B were followed to obtain Compound PR-1647. The yield, % yield and NMR spectrum of Compound PR-1647 are as follows. Yield: 0.61 g, % yield: 16.2%

$^1$H-NMR (CDCl$_3$, ppm) 1.24 (s, 9 H), 2.19 (s, 3 H), 3.05 (dd, J=6.48 Hz, 1.35 Hz, 2 H), 3.37 (s, 2 H), 5.36 (d, J=1.08 Hz, 1 H), 5.5 7 ( s, 1 H), 5.62 (d, J=15.7 Hz, 1 H), 6.03 (dt, J=15.7 Hz, 6.48 Hz, 1 H), 7.49 (t, J=7.83 Hz, 1 H), 7.83 (d, J=7.02 Hz, 1 H), 8.13 (d, J=5.94 Hz, 1 H), 8.38 (t, J=2.03 Hz, 1 H)

Further, in Synthetic Step C in Example 2, Compound PR-1647 was used instead of Compound PR-1257 and otherwise the procedures in Synthetic Step C were followed to obtain Compound PR-1648 as pale yellow crystals. The yield, % yield, melting point, NMR spectrum and IR spectrum of Compound PR-1648 are as follows. Yield: 0.12 9,% yield: 89.1%, melting point: 161 to 164° C.

$^1$H-NMR (CDCl$_3$, ppm) 1.24 (s, 9 H), 2.67 (d, J=4.86 Hz, 3 H), 3.54~3.63 (m, 2 H), 3.94~4.21 (m, 2 H), 5.64 (d, J=15.9 Hz, 1 H), 5.99 (s, 1 H), 6.12 (s, 1 H), 6.22 (dt, J=15.9 Hz, 7.70 Hz, 1 H), 7.65 (t, J=8.10 Hz, 1 H), 7.8 1 (m, 1 H), 8.24~8.27 (m, 2 H), 13.0 (broad s, 1 H) IR (KBr tablet, cm$^{-1}$): 2971, 2631, 1534, 1347

Example 18

Trans-2-[N-(6,6-dimethyl-2-hepten-4-ynyl)-N-methylamino]-4'-nitroacetophenone (Compound PR-1393), trans-N-(6,6-dimethyl-2-hepten-4-ynyl)-N-methyl-[2-(4-nitrophenyl)-2-propenyl]amine (Compound PR-1394), and hydrochloride of Compound PR-1394 (Compound PR-1395)

In Synthetic Step A in Example 1, 2-bromo-4'-nitroacetophenone obtained in Preparation Example 9 was used instead of 2-bromoacetophenone and sodium carbonate was used instead of potassium carbonate, and otherwise the procedures in Synthetic Step A were followed to obtain Compound PR-1393.

Further, in Synthetic Step B in Example 2, Compound PR-1393 was used instead of Compound PR-1130 and otherwise the procedures in Synthetic Step B were followed to obtain Compound PR-1394. The yield, % yield and NMR spectrum of Compound PR-1394 are as follows. Yield: 0.18 g, % yield: 6.3%

$^1$H-NMR (CDCl$_3$, ppm) 1.22 (s 9 H), 2.18 (s, 3 H), 3.04 (dd, J=6.48 Hz, 1.22 Hz, 2 H), 3.61 (s 2 H), 5.40 (d, J=0.81 Hz, 1 H), 5.58 (s, 1 H), 5.61 (d, 1 H, J=14.3 Hz), 6.00 (dt, J=14.3 Hz, 6.48 Hz, 1 H), 7.65 (d, J=8.78 Hz, 2 H), 8.18 (d, J=8.78 Hz, 2 H)

Further, in Synthetic Step C in Example 2, Compound PR-1394 was used instead of Compound PR-1257 and otherwise the procedures in Synthetic Step C were followed to obtain Compound PR-1395 as yellowish brown crystals. The yield, % yield, melting point, NMR spectrum and IR spectrum of Compound PR-1395 are as follows. Yield: 0.14 g, % yield: 69.7%, melting point: 159 to 162° C.

$^1$H-NMR (CDCl$_3$, ppm) 1.24 (s, 9 H), 2.65 (d, 3 H), 3.58~3.66 (m, 2 H), 3.95~4.24 (m, 2 H), 5.75 (d, J=15.4 Hz, 2 H), 6.00 (s, 1 H 6.14 (s, 1 H), 6.21 (dt, J=15.4 Hz, 7.56 Hz, 2 H), 7.60 (d, J=8.64 Hz, 2 H), 8.29 (d, J=8.64 Hz, 2 H), 13.0 (broad s, 1 H) IR (KBr tablet, cm$^{-1}$): 3470, 2971, 2933, 2908, 2870, 2694, 2676, 2628, 2572, 2504, 1599, 1524, 1471, 1463, 1395, 1345, 963, 936, 859

Example 19

Trans-3'-cyano-2-[N-(6,6-dimethyl-2-hepten-4-ynyl)-N-methylamino]acetophenone (Compound PR-1552), trans-3-{1-]N-(6,6-dimethyl-2-hepten-4-ynyl)-N-methylamino]methyl}vinylbenzonitrile (Compound PR-1553), and hydrochloride of Compound PR-1553 (Compound PR-1554)

In Synthetic Step A in Example 1, 2-bromo-3'-cyanoacetophenone obtained in Preparation Example 13 was used instead of 2-bromoacetophenone and otherwise the procedures in Synthetic Step A were followed to obtain Compound PR-1552. The yield, % yield and NMR spectrum of Compound PR-1552 are as follows. Yield: 1.05 g, % yield: 56.6%

$^1$H-NMR (CDCl$_3$, ppm) 1.26 (s, 9 H), 2.34 (s 3 H), 3.18 (dd, J=6.89 Hz, 1.49 Hz, 2 H), 3.76 (s, 2 H), 5.66 (d, 1 H, J=15.9 Hz), 6.04 (dt, J=15.9 Hz, 1.62 Hz, 1 H), 7.60 (t, J=8.10 Hz, 1 H), 7.85 (m, 1 H), 8.25 (m, 1 H), 8.33 (d, 1 H, J=1.35 Hz)

Further, in Synthetic Step B in Example 2, Compound PR-1552 was used instead of Compound PR-1130 and otherwise the procedures in Synthetic Step B were followed to obtain Compound PR-1553. The yield, % yield and NMR spectrum of Compound PR-1553 are as follows. Yield: 0.21 g, % yield: 20.0%

$^1$H-NMR (CDCl$_3$, ppm) 1.24 (s, 9 H), 2.17 (s, 3 H), 3.03 (dd, J=1.35 Hz, 6.62 Hz, 2 H), 3.33 (s, 2 H), 5.32 (s, 1 H), 5.49 (s, 1 H), 5.60 (dd, J=15.9 Hz, 1.35 Hz, 1 H), 6.01(dt, J=15.9 Hz, 6.62 Hz, 1 H), 7.42 (t, 1 H, J=7.56 Hz)), 7.55 (dt, J=7.29 Hz, 1.35 Hz, 1 H), 7.72 (dt, J=8.10 Hz, 1.35 Hz, 1 H), 7.80 (d, J=1.35 Hz, 1 H)

Further, in Synthetic Step C in Example 2, Compound PR-1553 was used instead of Compound PR-1257 and otherwise the procedures in Synthetic Step C were followed to obtain Compound PR-1554 as white crystals. The yield, % yield, melting point, NMR spectrum and IR spectrum of Compound PR-1554 are as follows. Yield: 0.23 g, % yield: 97.4%, melting point: 150 to 153° C.

$^1$H-NMR (CDCl$_3$, ppm) 1.24 (s, 9 H), 2.66 (d, J=4.59 Hz, 3 H), 3.53~3.67 (m, 2 H), 3.92~4.20 (m, 2 H), 5.75 (d, J=15.1 Hz, 1 H), 5.92 (S, 1 H), 6.08 (s, 1 H), 6.21 (dt, J=15.9 Hz, 7.56 Hz, 1 H), 7.57 (m, 1 H), 7.69 (m, 1 H), 12.9 (broad s, 1 H) IR (KBr tablet, cm$^{-1}$): 3425, 2972, 2934, 2908, 2871, 2692, 2676, 2595, 2574, 2530, 2501 2231, 1469, 1421, 1408, 1395, 963, 935, 802

Example 20

Trans-4'-cyano-2-[N-(6,6-dimethyl-2-hepten-4-ynyl)-N-methylamino]acetophenone (Compound PR-1559), trans-4-{1-[N-(6,6-dimethyl-2-hepten-4-ynyl)-N-methylamino]methyl}vinylbenzonitrile (Compound PR-1560), and hydrochloride of Compound PR-1560 (Compound PR-1561)

In Synthetic Step A in Example 1, 2-bromo-4'-cyanoacetophenone obtained in Preparation Example 24 was used instead of 2-bromoacetophenone and triethylamine was used instead of potassium carbonate, and otherwise the procedures in Synthetic Step A were followed to obtain Compound PR-1559. The yield, % yield and NMR spectrum of Compound PR-1559 are as follows. Yield: 0.52 g, % yield: 17.7%

$^1$H-NMR (CDCl$_3$, ppm) 1.24 (s, 9 H), 2.34 (s, 3 H), 3.17 (dd, J=6.75 Hz, 1.35 Hz, 1 H), 3.76 (s, 2 H), 5.65 (dt, J=15.66 Hz, 1.35 Hz, 1 H), 6.03 (dt, J=15.66 Hz, 6.75 Hz, 1 H), 7.76 (d, J=7.02 Hz, 2 H), 8.10 (d, J=7.02 Hz, 2 H)

Further, in Synthetic Step B in Example 2, Compound PR-1559 was used instead of Compound PR-1130 and otherwise the procedures in Synthetic Step B were followed to obtain Compound PR-1560. The yield, % yield and NMR spectrum of Compound PR-1560 are as follows. Yield: 0.21 g, % yield: 40.7%

$^1$H-NMR (CDCl$_3$, ppm) 1.26 (s, 9 H), 2.17 (s, 3 H), 3.03 (dd, J=6.75 Hz, 1.35 Hz, 1 H), 3.34 (s, 2 H), 5.36 (s, 1 H), 5.54 (s, 1 H), 5.60 (dt, J=15.66 Hz, 1.35 Hz, 1 H), 6.00 (dt, J=15.66 Hz, 1.35 Hz, 1 H), 7.51 (s, 4 H)

Further, in Synthetic Step C in Example 2, Compound PR-1560 was used instead of Compound PR-1257 and otherwise the procedures in Synthetic Step C were followed to obtain Compound PR-1561 as crystals. The yield, % yield, melting point, and NMR spectrum of Compound PR-1561 are as follows. Yield: 0.23 g, % yield: 97.4%, melting point: 190 to 191.5° C.

¹H-NMR (CDCl₃, ppm) 1.24 (s, 9 H), 2.64 (d, J=4.32 Hz, 3 H), 3.45~3.75 (m, 2 H), 3.97 (dd, J=14.04 Hz, 5.40 Hz, 1 H), 4.18 (dd, J=14.04 Hz, 3.78 Hz, 1 H), 5.75 (d, J=15.66 Hz, 1 H), 5.96 (s, 1 H), 6.10 (s, 3 H), 6.20 (dt, J=15.66 Hz, 7.29 Hz, 1 H), 7.54 (d, J=8.37 Hz, 2 H), 7.72 (d, J=8.37 Hz, 2 H), 12.91 (broad, 1 H)

Example 21

Ethyl trans-4-{2-[N-(6,6-dimethyl-2-hepten-4-ynyl)-N-methylamino]acetyl}benzoate (Compound PR-1685), ethyl trans-4-{1-[N-(6,6-dimethyl-2-hepten-4-ynyl)-N-methylamino]methyl}vinylbenzoate (Compound PR-1686), and hydrochloride of Compound PR-1686; (Compound PR-1687)

In Synthetic Step A in Example 1, ethyl 4-(2-bromoacetyl)benzoate obtained in Example 25 was used instead of 2-bromoacetophenone and triethylamine was used instead of potassium carbonate, and otherwise the procedures in Synthetic Step A were followed to obtain Compound PR-1685. The yield, % yield and NMR spectrum of Compound PR-1685 are as follows. Yield: 0.56 g, % yield: 11.8%

¹H-NMR (CDCl₃, ppm) 1.24 (s, 9 H), 1.42 (t, J=7.02 Hz, 3 H), 2.36 (s, 3 H), 3.21 (dd, J=6.75 Hz, 1.35 Hz, 2 H), 3.82 (s, 2 H), 4.41 (q, J=7.02 Hz, 2 H), 5.66 (dt, J=15.66 Hz, 1.35 Hz, 1 H), 6.07 (dt, J=15.66 Hz, 6.75 Hz), 8.03 (d, J=8.91 Hz, 2 H), 8.12 (d, J=8.91 Hz, 2 H)

Further, in Synthetic Step B in Example 2, Compound PR-1685 was used instead of Compound PR-1130 and otherwise the procedures in Synthetic Step B were followed to obtain Compound PR-1686. The yield, % yield and NMR spectrum of Compound PR-1686 are as follows. Yield: 0.14 g, % yield: 25.1%

¹H-NMR (CDCl₃, ppm) 1.24 (s, 9 H), 1.39 (t, J=7.02 Hz, 3 H), 2.18 (s, 3 H), 3.04 (dd, J=6.48 Hz, 1.62 Hz, 2 H), 3.35 (s, 2 H), 3.37 (q, J=7.02 Hz, 2 H), 5.32 (s, 1 H), 5.52 (s, 1 H), 5.61 (dt, J=15.66 Hz, 1.62 Hz, 1 H), 6.02 (dt, J=15.66 Hz, 6.48 Hz, 1 H), 5.54 (d, J=8.37 Hz, 2 H), 7.99 (d, J=8.37 Hz, 2 H)

Further, in Synthetic Step C in Example 2, Compound PR-1686 was used instead of Compound PR-1257 and otherwise the procedures in Synthetic Step C were followed to obtain Compound PR-1687 as crystals. The yield, % yield, melting point, and NMR spectrum of Compound PR-1687 are as follows. Yield: 92 mg, % yield: 59.3%, melting point: 136.5 to 138° C.

¹H-NMR (CDCl₃, ppm) 1.23 (s, 9 H), 1.41 (t, J=7.02 Hz, 3 H), 2.61 (d, J=4.86 Hz, 3 H), 3.49 (m, 1 H), 3.67 (m, 1 H), 4.04 (dd, J=13.77 Hz, 4.86 Hz, 1 H), 4.18 (dd, J=13.77 Hz, 3.78 Hz, 1 H), 4.39 (q, J=7.02 Hz, 2 H), 5.70 (d, J=15.66 Hz, 1 H), 5.93 (s, 1 H), 6.02 (s, 1 H), 6.22 (dt, J=15.66 Hz, 7.29 Hz, 1 H), 7.47 (d, J=8.37 Hz, 2 H), 8.09 (d, J=8.37 Hz, 2 H), 12.87 (broad, 1 H)

Example 22

Trans-2',4'-dichloro-2[N-(6,6-dimethyl-2-hepten-4-ynyl)-N-methylamino]acetophenone (Compound PR-1517), trans-N-(6,6-dimethyl-2-hepten-4-ynyl)-N-methyl-[2-(2,4-dichlorophenyl)-2-propenyl]amine (Compound PR-1518), and hydrochloride of Compound PR-1518 (Compound PR-1519)

In Synthetic Step A in Example 1, 2-bromo-2',4'-dichloroacetophenone obtained in Example 26 was used instead of 2-bromoacetophenone and triethylamine was used instead of potassium carbonate, and otherwise the procedures in Synthetic Step A were followed to obtain Compound PR-1517. The yield, % yield and NMR spectrum of Compound PR-1517 are as follows. Yield: 0.93 g, % yield: 27.8%

¹H-NMR (CDCl₃, ppm) 1.24 (s, 9 H), 2.34 (s, 3 H), 3.16 (dd, J=6.75 Hz, 1.35 Hz, 2 H), 3.72 (s, 2 H), 5.60 (dt, J=15.93 Hz, 1.35 Hz, 1 H), 5.98 (dt, J=15.93 Hz, 6.75 Hz, 1 H), 7.31 (dd, J=8.37 Hz, 1.62 Hz, 1 H), 7.43 (d, J=1.62 Hz, 1 H), 7.44 (d, J=8.37 Hz, 1 H)

Further, in Synthetic Step B in Example 2, Compound PR-1517 was used instead of Compound PR-1130 and otherwise the procedures in Synthetic Step B were followed to obtain Compound PR-1518. The yield, % yield and NMR spectrum of Compound PR-1518 are as follows. Yield: 0.25 g, % yield: 27.0%

¹H-NMR (CDCl₃, ppm) 1.24 (s, 9 H), 2.20 (s, 3 H), 3.02 (dd, J=6.48 Hz, 1.62 Hz, 2 H), 3.28 (s, 2 H), 5.16 (s, 1 H), 5.46 (s, 1 H), 5.55 (dt, J=15.66 Hz, 1.62 Hz, 1 H), 5.95 (dt, J=15.66 Hz, 6.48 Hz, 1 H), 7.13 (d, J=7.83 Hz, 1 H), 7.20 (dd, J=7.83 Hz, 1.89 Hz, 1 H), 7.37 (d, J=1.89 Hz, 1 H)

Further, in Synthetic Step C in Example 2, Compound PR-1518 was used instead of Compound PR-1257 and otherwise the procedures in Synthetic Step C were followed to obtain Compound PR-1519 as crystals. The yield, % yield, melting point, and NMR spectrum of Compound PR-1519 are as follows. Yield: 0.24.g, % yield: 86.5%, melting point: 179 to 180° C.

¹H-NMR (CDCl₃, ppm) 1.23 (s, 9 H), 2.68 (d, J=4.59 Hz, 3 H), 3.45~3.75 (m, 2 H), 3.94 (dd, J=14.31 Hz, 4.86 Hz, 1 H), 4.08 (dd, J=14.31 Hz, 3.51 Hz, 1 H), 5.67 (d, J=15.66 Hz, 1 H), 5.71 (s, 1 H), 6.18 (s, 1 H), 6.20 (dt, J=15.66 Hz, 7.56 Hz, 1 H), 7.27 (d, J=8.10 Hz, 1 H), 7.33 (dd, J=8.10 Hz, 1.89 Hz, 1 H), 7.46 (d, J=1.89 Hz, 1 H), 12.88 (broad, 1 H)

Example 23

Trans-3', 4'-dichloro-2-[N-(6,6-dimethyl-2-hepten-4-ynyl)-N-methylamino]acetophenone (Compound PR-1510), trans-N-(6,6-dimethyl-2-hepten-4-ynyl)-N-methyl-[2-(3,4-dichlorophenyl)-2-propenyl]amine (Compound PR-1511), and hydrochloride of Compound PR-1511 (Compound PR-1512)

In Synthetic Step A in Example 1, 2-bromo-3',4'-dichloroacetophenone obtained in Preparation Example 27 was used instead of 2-bromoacetophenone and triethylamine was used instead of potassium carbonate, and otherwise the procedures in Synthetic Step A were followed to obtain Compound PR-1510. The yield, % yield and NMR spectrum of Compound PR-1510 are as follows. Yield: 0.92 g, % yield: 27.2%

¹H-NMR (CDCl₃, ppm) 1.23 (s, 9 H), 2.33 (s, 3 H), 3.18 (dd, J=6.75 Hz, 1.62 Hz, 1 H), 3.72 (, 2 H), 5.66 (dt, J=15.66 Hz, 1.62 Hz, 1 H), 6.05 (dt, J=15.66 Hz, 6.75 Hz, 1H), 7.52 (d, J=8.37 Hz, 1 H), 7.83 (dd, J=8.37 Hz, 1.89 Hz, 1 H), 8.11 (d, J=1.89 Hz, 1 H)

Further, in Synthetic Step B in Example 2, Compound PR-1510 was used instead of Compound PR-1130 and otherwise the procedures in Synthetic Step B were followed to obtain Compound PR-1511. The yield, % yield and NMR spectrum of Compound PR-1511 are as follows. Yield: 0.32 g, % yield: 35%

¹H-NMR (CDCl₃, ppm) 1.24 (s, 9 H), 2.17 (s, 3 H), 3.03 (dd, J=6.75 Hz, 1.62 Hz, 1 H), 3.28 (s, 2 H), 2.62 (s, 1 H), 5.45 (s, 1 H), 5.62 (dt, J=15.66 Hz, 1.62 Hz, 1 H), 6.02 (dt, J=15.66 Hz, 6.75 Hz, 1 H), 7.32 (dd, J=8.37 Hz, 1.89 Hz, 1 H), 7.38 (d, J=15.66 Hz, 1 H), 7.59 (d, J=1.89 Hz, 1 H)

Further, in Synthetic Step C in Example 2, Compound PR-1511 was used instead of Compound PR-1257 and otherwise the procedures in Synthetic Step C were followed to obtain Compound PR-1512 as crystals. The yield, % yield, melting point, and NMR spectrum and of Compound PR-1512 are as follows. Yield: 0.29 g, % yield: 81.7%, melting point: 202.5 to 205.5° C.

$^1$H-NMR (CDCl$_3$, ppm) 1.24 (s 9 H), 2.64 (d J=3.78 Hz, 3 H), 3.47~3.73 (m, 2 H), 3.96 (m, 1 H), 4.12 (m, 1 H), 5.74 (d, J=15.93 Hz, 1 H), 5.88 (s, 1 H), 6.00 (s, 1 H), 6.22 (dt, J=15.93 Hz, 7.56 Hz, 1 H), 7.27 (dd, J=8.37 Hz, 1.89 Hz, 1 H), 7.49 (d, J=1.89 Hz, 1 H), 7.50 (d, J=8.37 Hz, 1 H), 12.89 (broad, 1 H)

Example 24

Trans-2',4'-dimethyl-2-[N-(6,6-dimethyl-2-hepten-4-ynyl)-N-methylamino]acetophenone (Compound PR-1710), trans-N-(6,6-dimethyl-2-hepten-4-ynyl)-N-methyl-[2-(2,4-dimethylphenyl)-2-propenyl] amine (Compound PR-1711), and hydrochloride of Compound PR-1711 (Compound PR-1712)

In Synthetic Step A in Example 1, 2-bromo-2',4'-dimethylacetophenone obtained in Preparation Example 11 was used instead of 2-bromoacetophenone and sodium carbonate was used instead of potassium carbonate, and otherwise the procedures in Synthetic Step A were followed to obtain Compound PR-1710. The yield, % yield and NMR spectrum of Compound PR-1710 are as follows. Yield: 1.07 g, % yield: 57.1%

$^1$H-NMR (CDCl$_3$, ppm) 1.24 (s, 9 H), 2.35 (s 3 H×2), 2.48 (s, 3 H), 3.18 (dd, J=6.89 Hz, 0.95 Hz, 2 H), 3.68 (s, 2 H), 5.63 (d, J=15.9 Hz, 1 H), 6.06 (dt, J=15.9 Hz, 6.89 Hz, 1 H), 7.03~7.06 (m, 2 H), 7.57 (d, J=8.64 Hz, 1 H)

Further, in Synthetic Step B in Example 2, Compound PR-1710 was used instead of Compound PR-1130 and otherwise the procedures in Synthetic Step B were followed to obtain Compound PR-1711. The yield, % yield and NMR spectrum of Compound PR-1711 are as follows. Yield: 0.21 g, % yield: 19.7%.

$^1$H-NMR (CDCl$_3$, ppm) 1.24 (s, 9 H), 2.23 (s, 3 H), 2.27 (s, 3 H) 2.30 (s, 3 H), 3.04 (dd, J=6.48 Hz, 1.08 Hz, 2 H), 3.16 (s, 2 H), 5.02 (d, J=1.89 Hz, 1 H), 5.40 (d, J=1.89 Hz, 1 H), 5.58 (d, J=15.9 Hz, 1 H), 6.00 (dt, J=15.9 Hz, 6.48 Hz, 1 H), 6.94~7.02 (m, 3 H)

Further, in Synthetic Step C in Example 2, Compound PR-1711 was used instead of Compound PR-1257 and otherwise the procedures in Synthetic Step C were followed to obtain Compound PR-1712 as white crystals. The yield, % yield, melting point, NMR spectrum and IR spectrum of Compound PR-1712 are as follows. Yield: 0.19 g, % yield: 80.5%, melting point: 180 to 183° C.

$^1$H-NMR (CDCl$_3$, ppm) 1.23 (s, 9 H), 2.29 (s, 3 H), 2.33 (s, 3 H) 2.61 (d, J=4.86 Hz, 3 H), 3.39~3.52 (m, 2 H), 3.93~3.94 (m, 2 H), 5.47 (d, J=15.7 Hz, 1 H), 5.54 (s, 1 H), 5.92 (s, 1 H), 6.18 (dt, J=15.9 Hz, 7.29 Hz, 1 H), 7.03~7.06 (m, 3 H ), 12.8 (broad s, 1 H) IR (KBr tablet, cm$^{-1}$): 3457, 2968, 2950, 2924, 2868, 2698, 2638, 1460, 969, 819

Example 25

Trans-3',4'-dimethyl-2-[N-(6,6-dimethyl-2-hepten-4-ynyl)-N-methylamino]acetophenone (Compound PR-1703), trans-N-(6,6-dimethyl-2-hepten-4-ynyl)-N-methyl-[2-(3,4-dimethylphenyl)-2-propenyl] amine (Compound PR-1704), and hydrochloride of Compound PR-1704 (Compound PR-1705)

In Synthetic Step A in Example 1, 2-bromo-3',4'-dimethylacetophenone obtained in Preparation Example was used instead of 2-bromoacetophenone and sodium carbonate was used instead of potassium carbonate, and otherwise the procedures in Synthetic Step A were followed to obtain Compound PR-1703. The yield, % yield and NMR spectrum of Compound PR-1703 are as follows. Yield: 0.88 g, % yield: 46.4%

$^1$-H-NMR (CDCl$_3$, ppm) 1.23 (s, 9 H), 2.31 (s, 3H×2), 2.38 (s, 3 H), 3.23 (dd, J=6.62 Hz, 1.49 Hz, 2 H), 3.80 (s, 2 H), 5.66 (d, J=15.9 Hz, 1 H), 6.10 (dt, J=15.9 Hz, 6.62 Hz, 1 H), 7.20 (d, J=7.29 Hz, 1 H), 7.70~7.74 (m, 2 H)

Further, in Synthetic Step B in Example 2, Compound PR-1703 was used instead of Compound PR-1103 and otherwise the procedures in Synthetic Step B were followed to obtain Compound PR-1704. The yield, % yield and NMR spectrum of Compound PR-1704 are as follows. Yield: 0.57 g, % yield: 66.1%

$^1$H-NMR (CDCl$_3$, ppm) 1.24 (s, 9 H), 2.19 (s, 3 H), 2.25 (s, 3 H) 2.27 (s, 3 H), 3.04 (dd, J=6.48 Hz, 1.62 Hz, 2 H), 3.31 (s, 2 H), 5.17 (d, J=1.35 Hz, 1 H), 5.38 (d, J=1.35 Hz, 1 H), 5.64 (dt, J=15.9 Hz, 1.49 Hz, 1 H), 6.06 (dt, J=15.9 Hz, 6.48 Hz, 1 H), 7.08 (d, J=7.83 Hz, 1 H) 7.20~7.38 (m, 2 H)

Further, in Synthetic Step C in Example 2, Compound PR-1704 was used instead of Compound PR-1257 and otherwise the procedures in Synthetic Step C were followed to obtain Compound PR-1705 as white crystals. The yield, % yield, melting point, NMR spectrum and IR spectrum of Compound PR-1705 are as follows. Yield: 0.52 g, % yield: 81.2%, melting point: 155 to 156° C.

$^1$H-NMR (CDCl$_3$, ppm). 1.23 (s, 9 H), 2.28 (s, 3 H), 2.29 (s, 3 H) 2.57 (d, J=3.51 Hz, 3 H), 3.41~3.67 (broad m, 2 H), 4.06 (broad s, 2 H), 5.63 (d, J=15.4 Hz, 1 H), 5.73 (s, 1 H), 5.76 (s, 1 H), 6.23 (dt, J=15.4 Hz, 2.30 Hz, 1 H), 7.08~7.26 (m, 3 H), 12.7 (broad s, 1 H) IR (KBr tablet, cm$^{-1}$): 2969, 2931, 2696, 2645, 2623, 1462, 1397, 965, 928

Example 26

Trans-3',4'-difluoro-2-[N-(6,6-dimethyl-2-hepten-4-ynyl)-N-methylamino]acetophenone (Compound PR-2171), trans-N-(6,6-dimethyl-2-hepten-4-ynyl)-N-methyl-[2-(3,4-difluorophenyl)-2-propenyl]amine (Compound PR-2172), and hydrochloride of Compound PR-2172 (Compound PR-2173)

In Synthetic Step A in Example 1, 2-bromo-3',4'-difluoroacetophenone obtained in Preparation Example 18 was used instead of 2-bromoacetophenone and otherwise the procedures in Synthetic Step A were followed to obtain Compound PR-2171. The yield, % yield and NMR spectrum of Compound PR-2171 are as follows. Yield: 0.42 g, % yield: 27.3%

$^1$H-NMR (CDCl$_3$, ppm) 1.24 (s, 9 H), 2.33 (s, 3 H), 3.17 (dd, J=1.62 Hz, 6.75 Hz, 2 H), 3.71 (s, 2 H), 5.65 (d, J=15.7 Hz, 1 H), 6.05 (dt, J=15.7 Hz, 6.75 Hz, 1 H), 7.23 (m, 1 H), J=7.77~7.93 (m, 2 H)

Further, in Synthetic Step B in Example 2, Compound PR-2171 was used instead of Compound PR-1130 and otherwise the procedures in Synthetic Step B were followed to obtain Compound PR-2172. The yield, % yield and NMR spectrum of Compound PR-2172 are as follows. Yield: 0.18 g, % yield: 43.0%

$^1$H-NMR (CDCl$_3$, ppm) 1.24 (s, 9 H), 2.17 (s, 3 H), 3.03 (dd, J=6.75 Hz, 1.35 Hz, 2 H), 3.28 (s, 2 H), 5.23 (s, 1 H), 5.41 (s, 1 H), 5.61 (d, J=15.9 Hz, 1 H), 6.02 (dt, J=15.9 Hz, 6.75 Hz, 1 H), 7.09 (m, 1 H), 7.19~7.39 (m, 2 H)

Further, in Synthetic Step C in Example 2, Compound PR-2172 was used instead of Compound PR-1257 and otherwise the procedures in Synthetic Step C were followed to obtain Compound PR-2173 as white crystals. The yield, % yield, melting point, NMR spectrum and IR spectrum of Compound PR-2173 are as follows. Yield: 0.18 g, % yield: 89.4%, melting point: 197 to 199° C.

¹H-NMR (CDCl₃, ppm) 1.24 (s, 9 H), 2.63 (d, 3 H, J=4.32 Hz), 3.51~3.70 (m, 2 H), 3.89~4.14 (m, 2 H), 5.74 (d, J=15.4 Hz, 1 H), 5.83 (s, 1 H), 5.94 (s, 1 H), 6.21 (dt, J=15.4 Hz, 7.56 Hz, 1 H), 7.13~7.27 (m, 3 H), 12.9 (broad s, 1 H) IR (KBr tablet, cm⁻¹): 2974, 2695, 2639, 1519, 1398, 1271

Example 27

Trans-3',5'-difluoro-2-[N-(6,6-dimethyl-2-hepten-4-ynyl)-N-methylamino]acetophenone (Compound PR-2157), trans-N-(6,6-dimethyl-2-hepten-4-ynyl)-N-methyl-[2-(3,5-difluorophenyl)-2-propenyl]amine (Compound PR-2158), and hydrochloride of Compound PR-2158 (Compound PR-2159)

In Synthetic Step A in Example 1, 2-bromo-3',5'-difluoroacetophenone obtained in Preparation Example 17 was used instead of 2-bromoacetophenone and otherwise the procedures in Synthetic Step A were followed to obtain Compound PR-2157. The yield, % yield and NMR spectrum of Compound PR-2157 are as follows. Yield: 0.59 g, % yield: 30.7%

¹H-NMR (CDCl₃, ppm) 1.25 (s, 9 H), 2.35 (s, 3 H), 3.18 (dd, J=6.75 Hz, 1.35 Hz, 2 H), 3.72 (s 2 H), 5.65 (dd, J=15.7 Hz, 1.35 Hz, 1 H), 6.05 (dt, J=15.7 Hz, 6.75 Hz, 1 H), 7.02 (m, 1 H), 7.26~7.58 (m, 2 H)

Further, in Synthetic Step B in Example 2, Compound PR-2157 was used instead of Compound PR-1130 and otherwise the procedures in Synthetic Step B were followed to obtain Compound PR-2158. The yield, % yield and NMR spectrum of Compound PR-2158 are as follows. Yield: 0.14 g, % yield: 23.9%

¹H-NMR (CDCl₃, ppm) 1.24 (s, 9 H), 2.18 (s, 3 H), 3.04 (dd, J=6.48 Hz, 1.35 Hz, 2 H), 3.27 (s, 2 H), 5.29 (s, 1 H), 5.48 (d, J=0.81 Hz, 1 H), 5.61 (dt, J=15.7 Hz, 1.35 Hz, 1 H), 6.03 (dt, J=15.7 Hz, 6.48 Hz, 1 H), 6.70 (m, 1 H), 6.99~7.22 (m, 2 H)

Further, in Synthetic Step C in Example 2, Compound PR-2158 was used instead of Compound PR-1257 and otherwise the procedures in Synthetic Step C were followed to obtain Compound PR-2159 as white crystals. The yield, % yield, melting point, NMR spectrum and IR spectrum of Compound PR-2159 are as follows. Yield: 0.10 g, % yield: 63.8%, melting point: 182 to 184° C.

¹H-NMR (CDCl₃, ppm) 1.24 (s, 9 H), 2.64 (d, 3 H, J=4.86 Hz), 3.51~3.66 (m, 2 H), 3.71~4.13 (m, 2 H), 5.75 (d, J=15.1 Hz, 1 H), 5.92 (s, 1 H), 6.08 (d, J=2.97 Hz, 1 H), 6.22 (dt, J=15.1 Hz, 7.56 Hz, 1 H), 6.80~7.24 (m, 4 H), 13.0 (broad s, 1 H) IR (KBr tablet, cm⁻¹): 3450, 2974, 2935, 1622, 1589, 1398, 1336, 1121

Example 28

Trans-4'-tert-butyl-2-[N-(6,6-dimethyl-2-hepten-4-ynyl)-N-methylamino]acetophenone (Compound PR-1717), trans-N-(6,6-dimethyl-2-hepten-4-ynyl)-N-methyl-[2-(4-tert-butylphenyl)-2-propenyl]amine (Compound PR-1718), and hydrochloride of Compound PR-1718 (Compound PR-1719)

In Synthetic Step A in Example 1, 2-bromo-4'-tert-butylacetophenone obtained in Preparation Example 12 was used instead of 2-bromoacetophenone and sodium carbonate was used instead of potassium carbonate, and otherwise the procedures in Synthetic Step A were followed to obtain Compound PR-1717. The yield, % yield and NMR spectrum of Compound PR-1717 are as follows. Yield: 0.96 g, % yield: 39.7%

¹H-NMR (CDCl₃, ppm) 1.23 (s, 9 H), 1.34 (s, 9 H), 2.36 (s, 3 H), 3.21 (d, J=5.40 Hz, 2 H), 3.80 (s, 2 H), 5.65 (d, J=15.4 Hz, 1 H), 6.08 (dt, J=15.4 Hz, 5.40 Hz, 1 H), 7.47 (d, J=8.37 Hz, 2 H), 7.93 (d, J=8.37 Hz, 2 H)

Further, in Synthetic Step B in Example 2, Compound PR-1717 was used instead of Compound PR-1130 and otherwise the procedures in Synthetic Step B were followed to obtain Compound PR-1718. The yield, % yield and NMR spectrum Compound PR-1718 are as follows. Yield: 0.42 g, % yield: 43.7%

¹H-NMR (CDCl₃, ppm) 1.24 (s, 9 H), 1.33 (s, 9 H), 2.20 (s, 3 H) 3.05 (d, J=7.02 Hz, 2 H), 3.33 (s, 2 H), 5.19 (s, 1 H), 5.43 (s, 1 H), 5.61 (dd, J=15.8 Hz, 1.49 Hz, 1 H), 6.06 (dt, J=15.8 Hz, 7.02 Hz, 1 H), 7.34 (d, J=6.48 Hz, 2 H), 7.44 (d, J=6.48 Hz, 2 H)

Further, in Synthetic Step C in Example 2, Compound PR-1718 was used instead of Compound PR-1257 and otherwise the procedures in Synthetic Step C were followed to obtain Compound PR-1719 as white crystals. The yield, % yield, melting point, NMR spectrum and IR spectrum of Compound PR-1719 are as follows. Yield: 0.38 g, % yield: 81.4%, melting point: 157 to 160° C.

¹H-NMR (CDCl₃, ppm) 1.23 (s, 9 H), 1.33 (s, 9 H), 2.59 (d, J=4.86 Hz, 3 H), 3.38~3.65 (m, 2 H), 4.00~4.15 (m, 2 H), 5.59 (d, J=15.9 Hz, 1 H), 5.81 (8s 1 H×2), 6.23 (dt, J=15.9 Hz, 7.56 Hz, 1 H), 7.30 (d, J=8.91 Hz, 2 H), 7.42 (d, J=8.91 Hz, 2 H ), 12.4 (broad s, 1 H) IR (KBr tablet, cm⁻¹): 3437, 3427, 2966, 2933, 2906, 2868, 2625, 2604, 2574, 1463, 1363

Example 29

Trans-2-[N-(6,6-dimethyl-2-hepten-4-ynyl)-N-methylamino]-2'-hydroxyacetophenone (Compound PR-1619), and hydrochloride of Compound PR-1619 (Compound PR-1620)

In Example 1,2-bromo-2'-hydroxyacetophenone obtained in Preparation Example 16 was used instead of 2-bromoacetophenone and sodium carbonate was used instead of potassium carbonate, and otherwise the procedures in Example 1 were followed to obtain Compounds PR-1619 and PR-1620. Compound PR-1620 was obtained as pale orange crystals. The yield, % yield and NMR spectrum of Compounds PR-1619 are as follows. Yield: 0.73 g, % yield: 25.9%

¹H-NMR (CDCl₃, ppm) 1.22 (s, 9 H), 3.05 (s, 3 H), 4.08 (d, J=7.29 Hz, 2 H), 4.81 (s, 2 H), 5.92 (d, J=15.9 Hz, 1 H), 6.25 (dt, J=15.4 Hz, 7.56 Hz, 1 H), 6.93 (t, J=7.70 Hz, 1 H), 7.09 (d, J=8.37 Hz, 1 H), 7.51 (t, J=7.70 Hz, 1 H), 7.68 (d, J=8.37 Hz, 1 H)

The yield, % yield, melting point, NMR spectrum and IR spectrum of Compound PR-1620 are as follows. Yield: 0.62 g, % yield: 75.2%, melting point: 75 to 130° C.

¹H-NMR (CDCl₃, ppm) 1.21 (s, 9 H), 3.05 (s 3 H), 4.06 (d, J=7.02 Hz, 2 H), 4.66 (s, 2 H), 5.88 (d, J=15.7 Hz, 1 H), 6.29 (dt, J=15.9 Hz, 7.83 Hz, 1 H), 6.97 (dt, J=7.29 Hz, 1.08 Hz, 1 H), 7.48 (dd, J=8.51 Hz, 1.08 Hz, 1 H), 7.55~7.65 (m, 2 H), 11.3 (s, 1 H), 13.2 (s, 1 H) IR (KBr tablet, cm⁻¹): 3430, 2970, 2932, 1648, 1617, 1604, 1458, 1363, 1291

Example 30

Trans-4'-tert-butyldimethylsilyloxy-2-[N (6,6-dimethyl-2-hepten-4-ynyl)-N-methylamino] acetophenone (Compound PR-1604), trans-N-(6,6-dimethyl-2-hepten-4-ynyl)-N-methyl-[2-(4-tert-butyldimethylsilyloxyphenyl)-2-propenyl]amine (Compound PR-1605), and trans-N-(6,6-dimethyl-2-hepten-4-ynyl)-N-methyl-[2-(4-hydroxyphenyl)-2-propenyl]amine (Compound PR-1606) In Synthetic Step A in Example 1,2-bromo-4'-tert-butyldimethylsilyloxyacetophenone obtained in Preparation Examples 14 and 15 was used instead of 2-bromoacetophenone and otherwise the procedures in Synthetic Step A were followed to obtain Compound PR-1604. The yield, % yield and NMR spectrum of Compound PR-1604 are as follows. Yield: 1.22 g, % yield: 21.7%

NMR spectrum (CD₃CN): 0.00 (s, 3 H×2), 0.73 (s, 9 H), 0.97 (s, 9 H), 2.02 (s, 3 H), 2.90 (dd, J=6.48 Hz, 1.35 Hz, 2

H), 3.48 (s, 2 H), 5.40 (dd, J=15.7 Hz, 1.08 Hz, 1 H), 5.70~5.81 (m, 1 H), 6.69 (d, J=9.99 Hz, 2 H), 7.68 (d, J=9.99 Hz, 2 H)

Further, in Synthetic Step B in Example 2, Compound PR-1604 was used instead of Compound PR-1130 and otherwise the procedures in Synthetic Step B were followed to obtain Compound PR-1605. The yield, % yield and NMR spectrum of Compound PR-1605 are as follows. Yield: 0.61 g, % yield: 61.2%

$^1$H-NMR (CDCl$_3$, ppm) 0.00(s, 3 H×2), 0.80 (s, 9 H), 1.04 (s, 9 H), 1.99 (s, 3 H), 2.83 (dd, J=6.48 Hz, 1.62 Hz, 2 H), 3.09 (s, 2 H), 4.93 (d, J=1.08 Hz, 1 H), 5.16 (d, J=1.89 Hz, 1 H), 5.81 (dd, J=16.6 Hz, 1.35 Hz, 1 H), 5.84 (dt, J=16.6 Hz, 6.48 Hz, 1 H), 6.58 (d, J=8.91 Hz, 2 H), 7.17 (d, J=8.91 Hz, 2 H)

0.61 g (1.53 mmol), of Compound PR-1605 and 1.45 g (4.60 mmol), of tetrabutylammonium fluoride trihydrate were dissolved in 10 ml of THF, and the mixture was stirred at room temperature for 18 hours. The reaction mixture was poured into ice water and extracted with 100 ml of diethyl ether. The organic extract was washed with water and then with saturated saline and dried with anhydrous sodium sulfate.

The solvent was distilled off under reduced pressure and the residue was purified by silica gel column chromatography (developing solvent: hexane ethyl acetate=5:1), to obtain Compound PR-1606 as pale yellow crystals. The yield, % yield, melting point, NMR spectrum and IR spectrum of Compound PR-1606 are as follows. Yield: 0.32 g, % yield: 73.8%, melting point: 105.5 to 108° C.

$^1$H-NMR (CDCl$_3$, ppm) 1.24 (s, 9 H), 2.20 (s, 3 H), 3.08 (d, J=6.48 Hz, 2 H), 3.33 (s, 2 H), 5.13 (s, 1 H), 5.32 (d, J=1.35 Hz, 1 H), 5.63 (d, J15.9 Hz, 1 H), 6.06 (d t J=8.91 Hz, 1.62 Hz, 1 H), 6.62 (d, J=8.64 Hz, 2 H), 7.29 (d, J=8.64 Hz, 2 H) IR (KBr tablet, cm$^{-1}$): 3081, 3036, 2968, 2926, 2906, 2868, 2844, 2790, 2746, 2662, 2599, 1609 1513, 1458, 1373, 1314, 1271, 1243, 997, 961, 869, 830

Example 31

Trans-N-(6,6-dimethyl-2-hepten-4-ynyl)-N-methyl-[2-(2-aminophenyl)-2-propenyl]amine (Compound PR-1672)

0.43 g (1.38 mmol), of trans-N-(6,6-dimethyl-2-hepten-4-ynyl)-N-methyl-[2-(2-nitrophenyl)-2-propenyl]amine (Compound PR-1640), obtained in Example 16 and 0.27 g (4.13 mmol), of zinc powder were mixed in the solution containing 19 ml of acetic acid and 1 ml of Millipore water, and the solution was heated at 80° C. for 3 hours. After the solvent was distilled off under reduced pressure, the residue was neutralized with a saturated aqueous sodium hydrogen carbonate solution and extracted with 100 ml of diethyl ether. The organic extract was washed with a saturated aqueous sodium hydrogen carbonate solution and with saturated saline and dried with anhydrous sodium sulfate.

The solvent was distilled off under reduced pressure and the residue was purified by silica gel column chromatography (hexane:ethyl acetate=3:1) to obtain Compound PR-1672. The yield, % yield and NMR spectrum of Compound PR-1672 are as follows. Yield: 0.14 g, % yield: 35.9%

$^1$H-NMR (CDCl$_3$, ppm) 1.24 (s, 9 H), 2.27 (s, 3 H), 3.10 (dd, J=1.35 Hz, 6.48 Hz, 2 H), 3.18 (s, 2 H), 5.30 (d, J=1.89 Hz, 1 H), 5.38 (d, J=1.89 Hz, 1 H), 5.61 (d, J=15.7 Hz, 1 H), 5.53 (dt, J 15.7 Hz, 6.48 Hz, 1 H), 6.64~6.71 (m, 2 H), 7.01~7.09 (m, 2 H), IR (KBr tablet, cm$^{-1}$) 3444, 3381, 3216, 3199, 3152, 2969, 2929, 2790, 1616, 1494, 1452, 914, 742

Example 32

Trans-N-(6,6-dimethyl-2-hepten-4-ynyl)-N-methyl-[2-(3-aminophenyl)-2-propenyl]amine (Compound PR-1676), and hydrochloride of Compound PR-1676 (Compound PR-1725)

In Example 31, Compound PR-1646 obtained in Example 17 was used instead of Compound PR-1640 and otherwise the procedures in Example 31 were followed to obtain Compound PR-1676. The yield, % yield and NMR spectrum of Compound PR-1676 are as follows. Yield: 008 g, % yield: 18.0%

$^1$H-NMR (CDCl$_3$, ppm) 1.24 (s, 9 H), 2.17 (s, 3 H), 3.04 (dd, J=6.75 Hz, 1.35 Hz, 2 H), 3.29 (s, 2 H), 3.65 (ブロ-ドs, 2 H), 5.19 (d, J=1.62 Hz, 1 H), 5.40 (d, J=1.35 Hz, 1 H), 5.62 (d, J=15.9 Hz, 1 H), 6.06 (dt, J=15.9 Hz, 6.48 Hz, 1 H), 6.61 (m, 1 H), 6.82 (t, J=1.89 Hz, 1 H), 6.88 (dd, J=6.08 Hz, 1.08 Hz, 1 H), 7.11 (t, J=7.56 Hz, 1 H)

Further, in Synthetic Step C in Example 2, Compound PR-1676 was used instead of Compound PR-1257 and otherwise the procedures in Synthetic Step C were followed to obtain Compound PR-1725 as brown crystals. The yield, % yield, melting point, NMR spectrum and IR spectrum of Compound PR-1725 are as follows. Yield: 0.0467 g, % yield: 51.7%, melting point: 190 to 192° C.

$^1$H-NMR (CDCl$_3$, ppm) 1.23 (s, 9 H), 2.66 (s, 3 H), 3.72 (ブロ-ドs, 2 H), 4.20~4.29 (m, 2 H), 5.72 (s, 1 H), 5. 79 (s, 1 H), 5.85 (d, 1 H, J=15.9 Hz), 6.06 (dt, 1 H, J=15.9 Hz, 7.29 Hz), 7.38~7.40 (broad m, 2 H ), 7.58~7.59 (broad m, 1 H), 7.85 (broad s, 1 H ) IR (KBr tablet, cm$^{-1}$) 3421, 2969, 2937, 2903, 2868, 2732, 2707, 2625, 2602, 1460

Example 33

N-cinnamyl-N-methyl-2-phenyl-2-propenylamine (Compound PR-1806), and hydrochloride of Compound PR-1806; (Compound PR-1807)

0.66 g (6.55 mmol), of triethylamine was dropped in 20 ml of a 40% methylamine-methanol solution.

After dropping, the mixture was stirred at room temperature for 20 hours and excess methylamine and methanol were removed under reduced pressure. The residue was extracted with diethyl ether/2N hydrochloric acid (100 ml/100 ml), and the water extract after neutralization with an aqueous sodium hydroxide solution was extracted with 100 ml of chloroform.

The organic extract was washed with a saturated aqueous sodium hydrogen carbonate solution and with saturated saline. After the organic extract was dried with anhydrous sodium sulfate, the solvent was distilled off under reduced pressure to obtain N-cinnamylmethylamine as yellow oily substance. The NMR spectrum of N-cinnamylmethylamine is as follows. Yield: 0.80 g, % yield: 83.0%

$^1$H-NMR (CDCl$_3$, ppm) 2.48 (S, 3 H), 3.38 (dd, J=6.21 Hz, 1.22 H z, 2 H), 6.29 (dt, J=16.5 Hz, 6.21 Hz, 1 H), 6.54 (d, J=16.5 Hz, 1 H), 7.19~7.40 (m, 5 H)

In Synthetic Step A in Example 1, N-cinnamylmethylamine obtained above was used instead of Compound PR-1133, sodium carbonate was used instead of potassium carbonate, and α-bromomethylstyrene obtained in Preparation Example 19 was used instead of 2-bromoacetophenone, and otherwise the procedures in Synthetic Step A were followed to obtain Compound PR-1806. The yield, % yield and NMR spectrum of Compound PR-1806 are as follows. Yield: 0.34 g, % yield: 66.5%

$^1$H-NMR (CDCl$_3$ ppm) 2.25 (s, 3 H), 1.69 (dd, J=9.45 Hz, 6.35H z, 2 H), 3.40 (s, 2 H), 5.26 (d, J=1.35 Hz, 1 H), 5.45 (d, J=1.62 Hz, 1 H), 6.27 (dt, J=15.7 Hz, 6.48 Hz, 1 H), 6.5 1 (d, J=15.7 H z, 1 H), 7.19~7.39 (m, 8 H), 7.47~7.51 (m, 2 H)

Further, in Synthetic Step C in Example 2, Compound PR-1806 was used instead of Compound PR-1257 and otherwise the procedures in Synthetic Step C were followed to obtain Compound PR-1807 as white crystals. The yield, % yield, melting point, NMR spectrum and IR spectrum of Compound PR-1807 are as follows. Yield: 0.31 g, % yield: 80.1%, melting point: 137 to 139° C.

$^1$H-NMR(CDCl$_3$, ppm) 2.64 (d, J=7.56 Hz,3 H), 3.47~3.77 (m,2 H), 4.13~4.16 (m,2 H), 5.87 (d, J=9.99 Hz, 2 H), 6.39~6.48 (m, 1 H×2), 7.32~7.42 (m, 10 H) IR (KBr tablet, cm$^{-1}$) 2969, 2889, 2822, 2251, 2709, 2673, 2643, 2596, 1497, 1465, 1449, 1414, 977, 967, 944, 783, 743, 722

Example 34

Trans-N-(6,6-dimethyl-2-hepten-4-ynyl)-N-ethyl-2-phenyl-2-propenylamine (Compound PR-1853), and hydrochloride of Compound PR-1853 (Compound PR-1854)

N-ethyl-2-phenyl-2-propenylamine obtained in Preparation Example 20 was dissolved in 6 ml of DMF and 390 mg of sodium carbonate was added thereto. While stirring the mixture under ice cooling, a solution of 740 mg of 1-bromo-6,6-dimethylhepten-4-yn (trans:cis=3:1), in 2 m of DMF was dropped. After the temperature was elevated to room temperature, the mixture was stirred for 68 hours. DMF was concentrated, and the residue was extracted with 100 ml of ether after the water was added. The ether extract was washed with water and dried with magnesium sulfate, and the solvent was distilled off under reduced pressure. The residue was purified by silica gel chromatography (SiO$_2$ 20 g, hexane:ethyl acetate=30:1), to obtain Compound PR-1853. Yield: 0.35 g, % yield: 34.0%

$^1$H-NMR (CDCl$_3$, ppm) 1.01 (t, J=7.02 Hz, 3 H), 1.24 (s, 9 H), 2.53 (q, J=7.02 Hz, 2 H), 3.11 (dd, J=6.48H z, 1.62 Hz, 2 H), 3.40 (s, 2 H), 5.27 (s, 1 H), 5.42 (s, 1 H), 5.60 (dt, J=15.93 Hz, 1.62 Hz, 1 H), 6.03 (dt, J=15.93 Hz, 6.48 Hz, 1 H), 7.25~7.38 (m, 3 H), 7.49 (m, 2 H)

Further, in Synthetic Step C in Example 2, Compound PR-1853 was used instead of Compound PR-1257 and otherwise the procedures in Synthetic Step C were followed to obtain Compound PR-1854 as crystals.

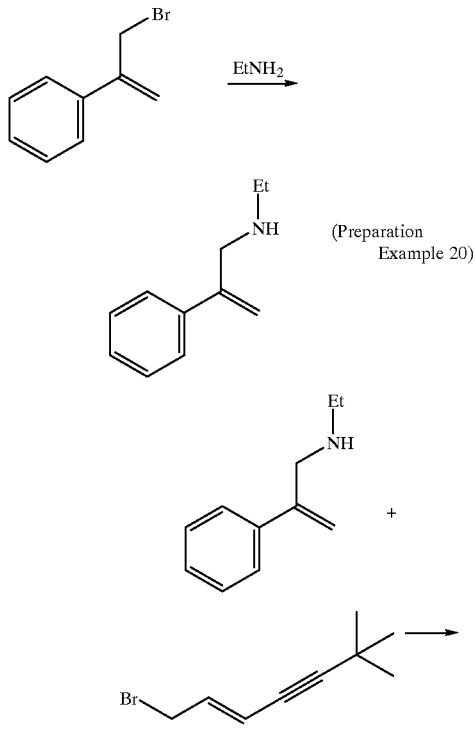

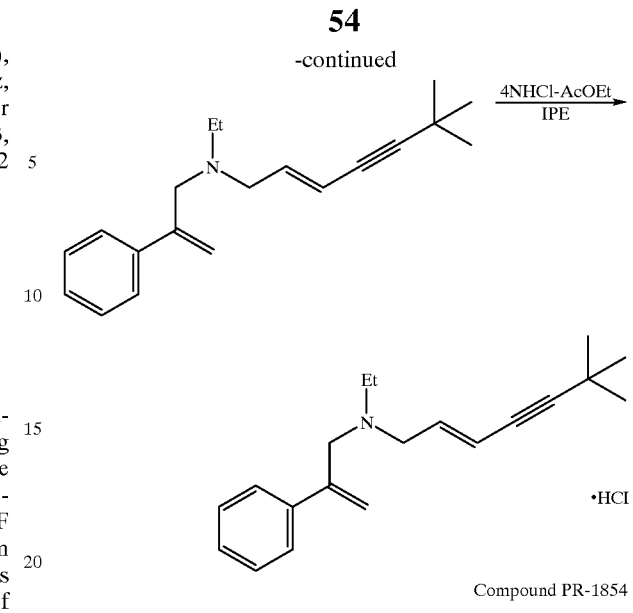

Compound PR-1854

(Et is the abbreviation of an ethyl group)

The yield, % yield, melting point and NMR spectrum of Compound PR-1854 are as follows. Yield: 0.34 g, % yield: 86.0%, melting point: 130.5 to 133° C.

1H-NMR (CDCl$_3$, ppm) 1.23 (s, 9 H), 1.39 (t, J=7.29 Hz, 3 H), 2.98 (m, 2 H), 3.55 (m, 2 H), 4.08 (m, 2 H), 5.61 (d, J=15.66 Hz, 1 H), 5.81 (d, J=1.35 H z, 1 H), 5.93 (d, J=2.97 Hz, 1 H), 6.24 (dt, J=15.66 Hz, 7.56 Hz, 1 H), 7.32~7.48 (m, 5 H), 12.56 (broad, 1 H)

Example 35

Trans-N-(6,6-dimethyl-2-hepten-4-ynyl)-N-isopropyl-2-phenyl-2-propenylamine (Compound PR-1855) and hydrochloride of Compound PR-1855 (Compound PR-1856)

In Example 34, N-isopropyl-2-phenyl-2-propenylamine obtained in Example 28 was used instead of N-ethyl-2-phenyl-2-propenylamine, and otherwise the procedures in Example 34 were followed to obtain Compound PR-1855, and its hydrochloride, Compound PR-1856. The yield, % yield and NMR spectrum of Compound PR-1855 are as follows. Yield: 0.48 g, % yield: 47.5%

$^1$H-NMR (CDCl$_3$, ppm) 0.97 (d, J=7.02 Hz, 6 H), 1.23 (s, 9 H), 3.01 (7 doublet, J=7.02 Hz, 1 H), 3.09 (dd, J=6.48 Hz, 1.62 Hz, 2 H), 3.37 (s, 2 H), 5.32 (s, 1 H), 5.38 (s, 1 H), 5.59 (dt, J=15.66 Hz, 1.62 Hz, 1 H), 5.97 (dt, J=15.66 Hz, 6.48 Hz, 1 H), 7.24~7.38 (m 3 H), 7.45 (m 2 H)

The yield, % yield, melting point and NMR spectrum of Compound PR-1856 are as follows. Yield: 0.49 g, % yield: 90.8%, melting point: 157.5 to 159.5° C.

$^1$H-NMR (CDCl$_3$, ppm) δ1.23 ( s, 9 H), 1.39 (d, J=7.02 Hz, 3 H), 1.42 (d, J=7.02 Hz, 3 H), 3.42~3.78 (m, 3 H), 3.90~4.10 (m, 2 H), 5.64 (dd, J=15.66 Hz, 1.35 Hz, 1 H), 5.86 (d, J=1.62 Hz, 1 H), 6.17 (d, J=2.97 Hz, 1 H), 6.43 (dt, J=15.66 Hz, 7.56 Hz, 1 H), 7.30~7.47 (m, 5 H ), 12.35 (broad, 1 H )

Example 36

Trans-N-cyclopropyl-N-(6,6-dimethyl-2-hepten-4-ynyl)-2-phenyl-2-propenylamine (Compound PR-1930) and hydrochloride of Compound PR-1930 (Compound PR-1931)

In Example 34, N-cyclopropyl-2-phenyl-2-propenylamine obtained in Preparation Example 29 was used instead of N-ethyl-2-phenyl-2-propenylamine and otherwise the procedures in Example 34 were followed to obtain Compound PR-1931 and its hydrochloride, Compound PR-1931. The yield, % yield and NMR spectrum of Compound PR-1930 are as follows. Yield: 0.77 g, % yield: 45.5%

$^1$H-NMR (CDCl$_3$, ppm) 0.30~0.44 (m, 4 H), 1.25 (s, 9 H), 1.83 (m, 1 H), 3.19 (dd, J=7.02 Hz, 1.62 Hz, 2 H), 3.61 (s, 2 H), 5.22 (s, 1 H), 5.39 (s, 1 H), 5.55 (dt, J=15.66 Hz, 1.62 Hz, 1 H), 6.09 (d t, J=15.66 Hz, 7.02 Hz, 1 H), 7.22~7.37 (m, 3 H), 7.44 (m, 2 H)

The yield, % yield, melting point and NMR spectrum of Compound PR-1931 are as follows. Yield: 0.71 g, % yield: 82.0%, melting point: 155 to 156.5° C. (decomp)

$^1$H-NMR (CDCl$^3$, ppm) 0.53 (m, 1 H), 0.80 (m, 1 H), 1.23 (s, 9 H), 1.45~1.65 (m, 2 H), 2.07 (m, 1 H), 3.51~3.77 (m, 2 H), 4.08~4.30 (m, 2 H), 5.58 (d, J=15.66 Hz, 1 H), 5.75 (s, 1 H), 5.79 (s, 1 H), 6.27 (dt, J=15.66 Hz, 7.5 6 Hz, 1 H), 7.40 (s, 5 H), 12.44 (broad, 1 H)

Example 37

2-[N-(4-tert-butylbenzyl)-N methylamino] acetophenone (Compound AD-001)

2.0 g (11.3 mmol) of N-(4-tert-butylbenzyl)methylamine obtained in Preparation Example 31 or 32 described above was dissolved in 15 ml of N,N-dimethylformamide (DMF), and 1.64 g(11.9 mmol), of potassium carbonate was added thereto. While stirring the solution in an ice bath, 5 ml of N,N-dimethylformamide solution containing 2.24 g (11.3 mmol) of 2-bromoacetophenone was dropped. After dropping, the mixture was stirred for 1 hour under ice cooling. The reaction mixture was poured into a mixture of ice and a saturated aqueous sodium hydrogen carbonate solution to stop the reaction. This was extracted with 200 ml and 100 ml, respectively, of ether and the ether extracts were washed with saturated saline and dried with anhydrous sodium sulfate. The solvent was distilled off under reduced pressure and the residue was purified by silica gel column chromatography (n-hexane : ethyl acetate=20:1), to obtain 2.24 g (yield: 67.2%), of Compound AD-001. The physical properties measured of Compound AD-001 were as follows.

$^1$H-NMR(CDCl$_3$, ppm) 1.31 (s, 9 H), 2.37 (s, 3 H), 3.65 (s, 2 H), 3.78 (s, 2 H), 7.25~7.60 (m, 7 H), 7.95 (d, J=7.02 Hz, 2 H)

Example 38

2-[N-(4-tert-butylbenzyl)-N-methylamino] acetophenone hydrochloride (Compound AD-002)

240 mg (0.81 mmol), of Compound AD-001 obtained in Example 37 above was dissolved in 1 ml of ethyl acetate, and 275 μl (1.1 mmol), of 4N hydrogen chloride-ethyl acetate solution was dropped while stirring at room temperature. After dropping, 10 ml of diethyl ether was added. The mixture was stirred at room temperature for 18 hours and crystals precipitated were collected by filtration. After the crystals were washed with diethyl ether, they were dried under reduced pressure in a desiccator to obtain 210 mg (yield: 77.9%), of Compound AD-002 as pale yellow crystals. The physical properties measured of Compound AD-002 were as follows. m.p. 178 to 180.50° C.

$^1$H-NMR (CDCl$_3$, ppm) 1.27 (s, 9 H), 3.11 (d, J=4.0 5 Hz, 3 H), 4.35 (d, J=17.28 Hz, 1 H), 4.47 (d, J=17.28 Hz, 1 H), 4.57 (d, J=5.40 Hz, 2 H), 7.39 (d, J=6.48 Hz, 2 H), 7.49 (t, J=7.56 Hz, 2 H), 7.54 (d, J=6.48 Hz, 2 H), 7.66 (t, J=7.56 Hz, 1 H), 7.80 (d, J=7.56 Hz, 2 H), 13.17 (br, 1 H)

Example 39

N-(4-tert-butylbenzyl)-N-methyl-2-phenyl-2-propenylamine (Compound AD-003)

1.7g (4.76 mmol) of methyltriphenylphosphonium-bromide was mixed with 20 ml of tetrahydrofuran, and 2.9 ml (4.76 mmol), of 1.65M n-butyl lithium-n-hexane solution was dropped while stirring at room temperature under nitrogen atmosphere. After dropping, the mixture was stirred for 1 hour, and then 3 ml of the tetrahydrofuran solution containing 1.0 g (3.39 mmol), of Compound AD-001 obtained in Example 37 above was dropped. After the mixture was stirred for 3 hours, it was poured into water with ice to stop the reaction. This was extracted with 150 ml of ethyl acetate, the organic extract was washed with saturated saline, and dried with anhydrous sodium sulfate. The solvent was distilled off under reduced pressure, and resulting residue was purified by silica gel column chromatography (n-hexane:ethyl acetate=5:1), to obtain 490 mg (yield: 49.3%), of Compound AD-003. The physical properties measured of Compound AD-003 were as follows.

$^1$H-NMR (CDCl$_3$, ppm) 1.31 (s, 9 H, 2.18 (s, 3 H), 3.37 (s, 2 H ), 3.48 (s, 2 H), 5.29 (s, 1 H), 5.46 (s, 1 H), 7.16 (d, J=8.37 Hz, 2 H), 7.25~7.38 (m, 5 H), 7.44 (d, J=8.37 Hz, 2 H)

Example 40

N-(4-tert-butylbenzyl)-N-methyl-2-phenyl-2-propenylamine hydrochloride (Compound AD-004)

Compound AD-003 obtained in Example 39 was used as a raw material and Compound AD-004 was obtained in the same manner as in Example 38. The physical properties measured of Compound AD-004 were as follows. m.p. 189 to 191.5° C.

$^1$H-NMR (CDCl$_3$, ppm) 1.30 (s, 9 H), 2.53 (d, J=5.40 Hz, 3 H), 3.95 (dd, J=12.96 Hz, 5.94 Hz, 1 H), 4.00~4.18 (m, 2 H), 4.19 (dd, J=14.04 Hz, 4.05 Hz, 1 H), 5.85 (s, 1 H), 5.8 8 (s, 1 H), 7.32~7.50 (m 9 H), 12.65 (br, 1 H)

Example 41

4'-bromo-2-[N-(4-tert-butylbenzyl)-N-methylamino] acetophenone (Compound AD-005), N-(4-tert-butylbenzyl)-N-methyl-[2-(4-bromophenyl-2-propenyl]amine (Compound AD-006), and hydrochloride of -Compound AD-006 (Compound AD-007)

4'-bromoacetophenone was used as a raw material and 2, 4'-dibromoacetophenone was obtained in the same manner as in Preparation Example 1. N-(4-tert-butylbenzyl) methylamine obtained in Preparation Example 31 or 32 and 2, 4'-dibromoacetophenone were used as raw materials and Compound AD-005 was obtained in the same manner as in Example 37. Compound AD-005 was used as a raw material and Compound AD-006 was obtained in the same manner as in Example 39. Compound AD-006 was used as a raw material and Compound AD-007 was obtained in the same manner as in Example 38. The physical properties measured of Compound AD-007 were as follows. m.p. 176 to 178° C. IR (KBr tablet, cm$^{-1}$) 2963, 2494, 1469, 834

$^1$H-NMR (CDCl$_3$, ppm) 1.31 (s, 9 H), 2.56 (d, J=5.13 Hz, 3 H), 3.93~4.20 (m, 2H×2), 5.86 (s, 1 H), 5.93 (s, 1 H), 7.15~7.59 (m, 8 H), 12.6 (br, 1 H)

Example 42

2-[N-(4-tert-butylbenzyl)-N-methylamino]-4'-chloroacetophenone (Compound AD-008), N-(4-tert-butylbenzyl)-N-methyl-[2-(4-chlorophenyl-2-propenyl]amine (Compound AD-009), and hydrochloride of Compound AD-009 (Compound AD-010)

4'-chloroacetophenone was used as a raw material and 2-bromo-4'-chloroacetophenone was obtained in the same manner as in Preparation Example 1. N-(4-tert-butylbenzyl) methylamine obtained in Preparation Example 31 or 32 and 2-bromo-4'-chloroacetophenone were used as raw materials and Compound AD-008 was obtained in the same manner as in Example 37. Compound AD-008 was used as a raw material and Compound AD-009 was obtained in the same manner as in Example 39. Compound AD-009 was used as a raw material and Compound AD-010 was obtained in the same manner as in Example 38. The physical properties measured of Compound AD-010 were as follows. m.p. 182 to 185.0° C. IR (KBr tablet, cm$^{-1}$) 2964, 2494, 1494, 1469, 838

$^1$H H-NMR (CDCl$_3$ppm) 1.31 (s, 9 H), 2.56 (d, J=5.13 Hz, 3 H), 3.9 3~4.20 (m, 2 H×2), 2 5.86 (s, 1 H), 5.93 (s, 1 H), 7.15~7.59 (m, 8 H), 12.6 (br, 1 H)

Example 43

2-[N-(4-tert-butylbenzyl)-N-methylamino]-4'-fluoroacetophenone (Compound AD-011), N-(4-tert-butylbenzyl)-N-methyl-[2-(4-fluorophenyl-2-propenyl]amine (Compound AD-012), and hydrochloride of Compound AD-012 (Compound AD-013)

N-(4-tert-butylbenzyl)methylamine obtained in Preparation Example 31 or 32 and 2-bromo-4'-fluoroacetophenone obtained in Preparation Example 1 were used as raw materials and Compound AD-011 was obtained in the same manner as in Example 37. Compound AD-011 was used as a raw material and Compound AD-012 was obtained in the same manner as in Example 39. Compound AD-012 was used as a raw material and Compound AD-013 was obtained in the same manner as in Example 38. The physical properties measured of Compound AD-013 were as follows. m.p. 182 to 185.0° C. IR (KBr tablet, cm$^{-1}$) 2421, 2404, 1601, 1510, 1463, 1425, 1407, 1225, 1162, 843, 805

$^1$H-NMR (CDCl$_3$, ppm) 1.27 (s, 9 H), 2.56 (d J=5.13 Hz, 3 H), 3.95~4.05 (m, 2 H), 4.11~4.22 (m, 2 H), 5.81 (s, 1 H), 5.87 (s, 1 H), 7.05~7.14 (m, 2 H), 7.27~7.56 (m, 6 H), 12.7 (brs, 1 H)

Example 44

2-[N-(4-tert-butylbenzyl)-N-methylamino]-2'-fluoroacetophenone (Compound AD-014), N-(4-tert-butylbenzyl)-N-methyl-[2-(2-fluorophenyl-2-propenyl]amine (Compound AD-015), and hydrochloride of Compound AD-015 (Compound AD-016)

N-(4-tert-butylbenzyl)methylamine obtained in Preparation Example 31 or 32 and 2-bromo-2'-fluoroacetophenone obtained in Preparation Example 2 were used as raw materials and Compound AD-014 was obtained in the same manner as in Example 37. Compound AD-014 was used as a raw material and Compound AD-015 was obtained in the same manner as in Example 39. Compound AD-015 was used as a raw material and Compound AD-016 was obtained in the same manner as in Example 38. The physical properties measured of Compound AD-016 were as follows. m.p. 152 to 153° C. IR (KBr tablet, cm$^{-1}$) 2964, 1489, 1449, 763

$^1$H-NMR (CDCl$_3$ ppm) 1.30 (s, 9 H), 5.89 (d, J=4.86 Hz, 3 H), 4.00~4.05 (m, 2 H), 4.13~4.17 (m, 2 H), 5.81 (s, 1 H), 6.10 (s, 1 H), 7.08~7.56 (m, 8 H)

Example 45

2-[N-(4-tert-butylbenzyl)-N-methylamino]-2'-bromoacetophenone (Compound AD-017), N-(4-tert-butylbenzyl)-N-methyl-[2-(2-bromophenyl-2-propenyl]amine (Compound AD-018), and hydrochloride of Compound AD-018 (Compound AD-019)

N-(4-tert-butylbenzyl)methylamine obtained in Preparation Example 31 or 32 and 2, 2'-dibromoacetophenone obtained in Preparation Example 3 were used as raw materials and Compound AD-017 was obtained in the same manner as in Example 37. Compound AD-017 was used as a raw material and Compound AD-018 was obtained in the same manner as in Example 39. Compound AD-018 was used as a raw material and Compound AD-019 was obtained in the same manner as in Example 38. The physical properties measured of Compound AD-019 were as follows. m.p. 142 to 144° C. IR (KBr tablet, cm$^{-1}$) 3421, 2961, 2910 2871, 2700, 2629, 1467, 1422, 767

$^1$H-NMR (CDCl$_3$, ppm) 1.30 (s, 9 H), 2.63 (d, J=4.86 Hz, 3 H), 4.00~4.17 (m, 2 H×2), 7.22~7.65 (m, 8 H), 12.6 (brs, 1 H)

Example 46

2-[N-(4-tert-butylbenzyl)-N-methylamino]-3'-bromoacetophenone (Compound AD-020), N-(4-tert-butylbenzyl)-N-methyl-[2-( 3-bromophenyl)-2-propenyl]amine (Compound AD-021), and hydrochloride of Compound AD-021 (Compound AD-022)

N-(4-tert-butylbenzyl)methylamine obtained in Preparation Example 31 or 32 and 2, 3'-dibromoacetophenone obtained in Preparation Example 4 were used as raw materials and Compound AD-020 was obtained in the same manner as in Example 37. Compound AD-020 was used as a raw material and Compound AD-021 was obtained in the same manner as in Example 39. Compound AD-021 was used as a raw material and Compound AD-022 was obtained in the same manner as in Example 38. The physical properties measured of Compound AD-022 were as follows. m.p. 155 to 157° C. IR (KBr tablet, cm$^{-1}$) 2961, 2517, 1469

$^1$H-NMR (CDCl$_3$, ppm) 1.31 (s, 9 H), 2.5 8 (d, J=4.86 Hz, 3 H), 3.94~4.20 (m, 2 H×2), 5.88 (s, 1 H), 5.97 (s, 1 H), 7.26~7.53 (m, 8 H), 12.7 (brs, 1 H)

Example 47

2-[N-(4-tert-butylbenzyl)-N-methylamino]-3'-methylacetophenone (Compound AD-023), N-(4-tert-butylbenzyl)-N-methyl-[2-(3-methylphenyl)-2-propenyl]amine (Compound AD-024), and hydrochloride of Compound AD-024 (Compound AD-025)

N-(4-tert-butylbenzyl)methylamine obtained in Preparation Example 31 or 32 and 2-bromo-3'-methylacetophenone obtained in Preparation Example 5 were used as raw materials and Compound AD-023 was obtained in the same manner as in Example 37. Compound AD-023 was used as a raw material and Compound AD-024 was obtained in the same manner as in Example 39. Compound AD-024 was used as a raw material and Compound AD-025 was obtained in the same manner as in Example 38. The physical properties measured of Compound AD-025 were as follows. m.p. 149 to 151° C. IR (KBr tablet, cm$^-$) 2961, 2910, 2624, 2501, 1465

$^1$H-NMR (CDCl$_3$, ppm) 1.30 (s, 9 H), 2.38 (s, 3 H), 2.54 (d, J=4.05 Hz, 3 H), 3.92~4.22 (m, 2 H×2), 5.82 (s, vinylproton, 1 H×2), 7.12~7.65 (m, 4 H), 12.6 (brs, 1 H)

Example 48

2-[N-(4-tert-butylbenzyl)-N-methylamino]-2'-methylacetophenone (Compound AD-026), N-(4-tert-butylbenzyl)-N-methyl-[2-(2-methylphenyl)-2-propenyl]amine (Compound AD-027), and hydrochloride of Compound AD-027 (Compound AD-028)

N-(4-tert-butylbenzyl)methylamine obtained in Preparation Example 31 or 32 and 2-bromo-2'-methylacetophenone obtained in Preparation Example 6 were used as raw materials and Compound AD-026 was obtained in the same manner as in Example 37. Compound AD-026 was used as a raw material and Compound AD-027 was obtained in the same manner as in Example 39. Compound AD-027 was used as a raw material and Compound AD-028 was obtained in the same manner as in Example 38. The physical properties measured of Compound AD-028 were as follows. m.p. 160 to 163° C. IR (KBr tablet, cm$^{-1}$) 3424, 2961, 2625, 2543, 1463

$^1$H-NMR (CDCl$_3$), ppm) 1.29 (s, 9 H), 2.15 (s, 3 H), 2.50 (d, J=4.86 Hz, 2 H), 3.88~4.05 (m, 2 H×2), 5.60 (s, 1 H), 5.99 (s, 1 H), 7.16~7.40 (m, 8 H), 12.6 (brs, 1 H)

Example 49

2-[N-(4-tert-butylbenzyl)-N-methylamino]-2'-methoxyacetophenone (Compound AD-029), N-(4-tert-butylbenzyl)-N-methyl-[2-(2-methoxyphenyl)-2-propenyl]amine (Compound AD-030), and hydrochloride of Compound AD-030 (Compound AD-031)

N-(4-tert-butylbenzyl)methylamine obtained in Preparation Example 31 or 32 and 2-bromo-2'-methoxyacetophenone obtained in Preparation Example 7 were used as raw materials and Compound AD-029 was obtained in the same manner as in Example 37. Compound AD-029 was used as a raw material and Compound AD-030 was obtained in the same manner as in Example 39. Compound AD-030 was used as a raw material and Compound AD-031 was obtained in the same manner as in Example 38. The physical properties measured of Compound AD-031 were as follows. m.p. 168 to 170° C. IR (KBr tablet, cm$^{-1}$) 3421, 2959, 2871, 2523, 1488, 1463, 1396, 1267, 1245, 928, 754

$^1$H-NMR (CDCl$_3$, ppm) 1.30 (s, 9 H), 2.56 (d, J=4.59 Hz, 3 H), 3.74 (s, 3 H), 3.94~4.17 (m, 2 H×2), 5.63 (s, 1 H), 5.81 (s, 1 H), 6.90 (d,J=11.9 Hz, 1 H), 7.02 (t, J=7.02 Hz, 1 H), 7.23~7.44 (m, 6 H), 12.3 (brs, 1 H)

Example 50

N-(4-tert-butylbenzyl)-N-methyl-[2-(2-nitrophenyl)-2-propenyl]amine (Compound AD-032), and hydrochloride of Compound AD-032 (Compound AD-033)

2'-nitroacetophenone was used as a raw material and 2-bromo-2'-nitroacetophenone was obtained in the same manner as in Preparation Example 1. N-(4-tert-butylbenzyl)methylamine obtained in Preparation Example 31 or 32 and 2-bromo-2'-nitroacetophenone were used as raw materials and reacted in the same manner as in Example 37 to obtain 2-[N-(4-tert-butylbenzyl)-N-methylamino]-2'-nitroacetophenone. This compound was unstable so that next reaction was proceeded without purifying it. By using the non-purified raw material, Compound AD-032 was obtained in the same manner as in Example 39. Compound AD-032 was used as a raw material and Compound AD-033 was obtained in the same manner as in Example 38. The physical properties measured of Compound AD-033 were as follows. m.p. 175 to 178° C. IR (KBr tablet, cm$^{-1}$) 3417, 2963, 1527, 1348 1H-NMR (CDCl$_3$, ppm) 1.31 (s, 9 H), 2.72 (d, J=4.32 Hz, 3 H), 3.80~3.87 (m, 2 H), 4.21 (d, J=5.67 Hz, 2 H), 5.62 (s, 1 H), 6.07 (s, 1 H), 7.40~7.71 (m, 7 H), 8.02 (dd, J=1.35 Hz, 8.10 Hz, 1 H), 12.7 (brs, 1 H)

Example 51

N-(4-tert-butylbenzyl)-N-methyl-[2-(4-nitrophenyl)-2-propenyl]amine (compound AD-034), and hydrochloride of Compound AD-034 (Compound-AD-0035)

N-(4-tert-butylbenzyl)methylamine obtained in Preparation Example 31 or 32 and 2-bromo-4'-nitroacetophenone obtained in Preparation Example 8 were used as raw materials and reacted in the same manner as in Example 37 to obtain 2-[N-(4-tert-butylbenzyl), -N-methylamino]-4'-nitroacetophenone. This compound was unstable so that next reaction was proceeded without purifying it. By using the non-purified raw material, Compound AD-034 was obtained in the same manner as in Example 39. Compound AD-034 was used as a raw material and Compound AD-035 was obtained in the same manner as in Example 38. The physical properties measured of Compound AD-035 were as follows. m.p. 183 to 185° C. IR (KBr tablet, cm$^{-1}$) 3426, 2965, 2682, 2628, 2556, 2519, 1598, 1521, 1468, 1413, 1345, 859

$^1$H-NMR (CDCl$_3$, ppm) 1.28 (s, 9 H), 2.63 (d, J=4.86 Hz, 3 H), 3.97 (dd, J=5.94 Hz, 14.0 Hz, 2 H), 4.16 (d, J=4.59 Hz, 2 H), 6.01 (s, 1 H), 6.15 (s, 1 H), 7.41~7.47 (m, 4 H), 7.54 (d, J=8.91 H z, 2 H), 8.25 (d, J=8.91 Hz, 2 H), 12.8 (br s, 1 H)

Example 52

N-(4-tert-butylbenzyl)-N-methyl-[2-(3-nitrophenyl)-2-propenyl]amine (Compound AD-036), and hydrochloride of Compound AD-036 (Compound AD-037)

N-(4-tert-butylbenzyl)methylamine obtained in Preparation Example 31 or 32 and 2-bromo-3'-nitroacetophenone obtained in Preparation Example 9 were used as raw materials and reacted in the same manner as in Example 37 to obtain 2-[N-(4-tert-butylbenzyl), -N-methylamino]-3'-nitroacetophenone. This compound was unstable so that next reaction was proceeded without purifying it. By using the non-purified raw material, Compound AD-036 was obtained in the same manner as in Example 39. Compound AD-036 was used as a raw material and Compound AD-037 was obtained in the same manner as in Example 38. The physical properties measured of Compound AD-037 were as follows. m.p. 155 to 157° C. IR (KBr tablet, cm$_{-1}$) 3436, 3425, 2964, 2911, 2874, 2676, 2626, 1530, 1467, 1393, 1347

$^1$H-NMR (CDCl$_3$, ppm) 1.32 (s, 9 H), 2.66 (d, J=5.13 Hz, 3 H), 3.89~3.96 (m, 2 H), 4.08~4.23 (m, 2 H), 5.99 (s, 1 H), 6.10 (s, 1 H), 7.44~751 (m, 4 H), 7.62 (t, J=8.10 Hz, 1 H), 7.75 (m, 1 H), 8.16 (t, J=1.76 Hz, 1 H), 8.24 (m, 1 H), 12.8 (brs, 1 H)

Example 53

N-(4-tert-butylbenzyl)-N-methyl-[2-3-aminophenyl)-2-propenyl]amine (Compound AD-038), and hydrochloride of Compound AD-038 (Compound AD-039)

Compound AD-032 (500 mg (1.48 mmol)), obtained in Example 50, 18 ml of acetic acid, 2 ml of purified water and 0.19 9 (2.95 mmol), of zinc powder were heated together at 90° C. for 1.5 hours. After neutralizing with a saturated aqueous sodium hydrogen carbonate, the reaction solution was extracted with 100 ml of diethyl ether, and the organic extract was washed with a saturated aqueous sodium hydrogen carbonate and with saturated saline. After drying with sodium sulfate, the solvent was distilled off under reduced pressure. The residue was purified by silica gel column chromatography (chloroform : methanol=30:1), to obtain Compound AD-038. Compound AD-038 was used as a raw material and Compound AD-039 was obtained in the same manner as in Example 38. The physical properties measured of Compound AD-039 were as follows. m.p. 206 to 208° C. IR (KBr tablet, cm$^{-1}$) 3422, 2960, 2906, 2870, 2597, 1465

$^1$H-NMR (CDCl$_3$, ppm) 1.27 (s, 9 H), 2.61 (s, 3 H), 4.06 (s, 2 H), 4.24 (s, 2 H), 4.3 6 (s, 2 H), 5.67 (s, 1 H), 5.73 (s, 1 H), 7.33~7.48 (m, 6 H), 7.62 (d, J=7.56 Hz, 1 H), 7.09 (s, 1 H)

Example 54

N-(4-tert-butylbenzyl)-N-methyl-[2-(2-aminophenyl)-2-propenyl]amine (Compound AD-040)

Compound AD-036 obtained in Example 52 was used as a raw material and reduced in the same manner as in Example 53 to obtain Compound AD-040. The physical properties measured of Compound AD-040 were as follows. IR (KBr tablet, cm$^{-1}$) 2963, 2904, 2869, 2790, 1613, 1494, 1453, 1262, 1095, 1019, 804, 748

$^1$H-NMR (CDCl$_3$, ppm) 1.31 (s, 9 H), 2.23 (s, 3 H), 3.25 (s, 2 H), 3.53 (s, 2 H), 4.52 (brs, 2 H), 5.33 (d, J=1.89 Hz, 1 H), 5.46 (d, J=0.81 Hz, 1 H), 6.53~6.72 (m, 2 H), 7.01~7.10 (m, 2 H), 7.16~7.32 (m, 6 H)

Example 55

2-[N-(4-tert-butylbenzyl)-N-methylamino]-3',4'-dimethylacetophenone (Compound AD-041), N-(4-tert-butylbenzyl)-N-methyl-[2-(3,4-dimethylphenyl)-2-propenyl]amine (Compound AD-042), and hydrochloride of Compound AD-042 (Compound AD-043)

N-(4-tert-butylbenzyl)methylamine obtained in Preparation Example 31 or 32 and 2-bromo-3',4'-dimethylacetophenone obtained in Preparation Example 10 were used as raw materials and Compound AD-041 was obtained in the same manner as in Example 37. Compound AD-041 was used as a raw material and Compound AD-042 was obtained in the same manner as in Example 39. Compound AD-042 was used as a raw material and Compound AD-043 was obtained in the same manner as in Example 38. The physical properties measured of Compound AD-043 were as follows. m.p. 172 to 175° C. IR (KBr tablet, cm$^{-1}$) 3488, 2961, 2528, 1463

$^1$H-NMR (CDCl$_3$, ppm) 1.30 (s, 9 H), 2.28 (s, 3 H×2), 2.52 (d, J=4.05 Hz, 3 H), 3.90~4.18 (m, 2 H×2), 5.76 (s, 1 H), 5.79 (s, 1 H), 7.08~7.17 (m, 3 H), 7.40~7.49 (m, 4 H), 12.6 (brs, 1 H)

Example 56

2-[N-(4-tert-butylbenzyl)-N-methylamino]-2',4'-dimethylacetophenone (compound AD-044), N-( 4-tert-butylbenzyl)-N-methyl-[2-(2,4-dimethylphenyl)-2-propenyl]amine (Compound AD-045), and hydrochloride of Compound AD-045 (Compound AD-046)

N-(4-tert-butylbenzyl )methylamine obtained in Preparation Example 31 or 32 and 2-bromo-2',4'-dimethylacetophenone obtained in Preparation Example 11 were used as raw materials and Compound AD-044 was obtained in the same manner as in Example 37. Compound AD-044 was used as a raw material and Compound AD-045 was obtained in the same manner as in Example 39. Compound AD-045 was used as a raw material and Compound AD-046 was obtained in the same manner as in Example 38. The physical properties measured of Compound AD-046 were as follows. white crystal IR (KBr tablet, cm$^{-1}$) 3426, 3011, 2962, 2925, 2869, 2704, 2625, 2545, 1464, 1416, 1365, 832, 816

$^1$H-NMR (CDCl$_3$, ppm) 1.29 (s, 9 H), 2.23 (s, 3 H), 2.34 (s, 3 H), 2.57 (s, 3 H), 3.8 8~4.01 (m, 2 H×2), 5.56 (s, 1 H), 5.94 (s, 1 H), 7.06 (s, 3 H), 7.33~7.43 (m, 4 H), 12.6 (brs, 1 H)

Example 57

4'-tert-butyl-2-[N-(4-tert-butylbenzyl)-N-methylamino]acetophenone (Compound AD-047), N-(4-tert-butylbenzyl)-N-methyl-[2-(4-tert-butylphenyl)-2-propenyl]amine (Compound AD-048), and hydrochloride of Compound AD-048 (Compound AD-049)

N-(4-tert-butylbenzyl)methylamine obtained in Preparation Example 31 or 32 and 2-bromo-4'-tert-buthylacetophenone obtained in Preparation Example 12 were used as raw materials and Compound AD-047 was obtained in the same manner as in Example 37. Compound AD-047 was used as a raw material and Compound AD-048 was obtained in the same manner as in Example 39. Compound AD-048 was used as a raw material and Compound AD-049 was obtained in the same manner as in Example 38. The physical properties measured of Compound AD-049 were as follows. white crystal m.p. 184 to 187° C. IR (KBr tablet, cm$^{-1}$) 3425, 2962, 2905, 2869, 1464

$^1$H-NM R (CDCl$_3$, ppm) 1.30 (s, 9 H), 1.33 (s, 9 H), 2.53 (d, J=4.86 Hz, 3 H), 3.88~4.21 (m, 2 H×2), 5.83 (s, 2 H), 7.20~7.48 (m, 8 H), 12.6 (brs 1 H)

Example 58

2-[N-(4-tert-butylbenzyl)-N-methylamino]-3'-cyanoacetophenone (Compound AD-050), 3-[1-{N-(4-tert-butylbenzyl)-N-methylamino}methyl]vinylbenzonitrile (Compound AD-051), and hydrochloride of Compound AD-051 (Compound AD-052)

N-(4-tert-butylbenzyl)methylamine obtained in Preparation Example 31 or 32 and 2-bromo-3'-cyanoacetophenone obtained in Preparation Example 13 were used as raw materials and Compound AD-050 was obtained in the same manner as in Example 37. Compound AD-050 was used as a raw material and Compound AD-051 was obtained in the same manner as in Example 39. Compound AD-051 was used as a raw material and Compound AD-052 was obtained in the same manner as in Example 38. The physical properties measured of Compound AD-052 were as follows. white crystal m.p. 140 to 143° C. IR (KBr tablet, cm$^{-1}$) 3423, 2965, 1466, 807

$^1$H-NMR (CDCl$_3$, ppm) 1.32 (s, 9 H), 2.63 (d, J=4.86 Hz, 3 H), 3.87~3.94 (m, 2 H), 4.13~4.18 (m, 2 H), 5.92 (s, 1 H), 6.07 (s, 1 H), 7.44~7.68 (m, 7 H), 12.8 (brs, 1 H)

Example 59

2-[N-(4-tert-butylbenzyl)-N-methylamino]-4'-tert-butyldimethylsilyloxyacetophenone (Compound AD-053), N-(4-tert-butylbenzyl)-N-methyl-[2-(4-tert-butyldimethylsilyloxyphenyl)-2-propenyl]amine (Compound AD-054)

N-(4-tert-butylbenzyl)methylamine obtained in Preparation Example 31 or 32 and 2-bromo-4'-tert-butyldimethylsilyloxyacetophenone obtained in Preparation Examples 14 and 15 were used as raw materials and Compound AD-053 was obtained in the same manner as in Example 37. Compound AD-053 was used as a raw material and Compound AD-054 was obtained in the same manner as in Example 39. The physical properties measured of Compound AD-054 were as follows.

$^1$H-NMR (CDCl$_3$, ppm) 0.10 (s, 3 H×2), 0.89 (s, 9 H), 1.17 (s, 9 H), 1.97 (s, 3 H 3.23 (s, 2 H), 3.30 (s, 2 H), 6.69 (d, J=8.37 Hz, 2 H), 6.98 (d, J=8.37 Hz, 2 H), 7.20 (d, J=8.37 Hz, 2 H), 7.25 (d, J=8.37 Hz, 2 H)

Example 60

N-(4-tert-butylbenzyl)-N-methyl-[2-(4-hydroxyphenyl)-2-propenyl]amine (Compound AD-055)

0.43 g (1.01 mmol) of Compound 54 and 0.96 g (3.04 mmol) of n-butylammonium fluoride were dissolved in 10 ml of tetrahydrofuran, and the mixture was stirred at room temperature for 18 hours. The reaction mixture was poured into ice water to stop the reaction and extracted with 50 ml of ethyl acetate. The organic extract was washed with saturated saline and dried with anhydrous sodium sulfate. The solvent was distilled off under reduced pressure and the residue was purified by silica gel column chromatography (n-hexane:ethyl acetate=4:1→0:10) to obtain 0.26 g (yield: 83.2%), of Compound AD-055 as brown oily substance. The physical properties measured of Compound AD-055 were as follows. IR (KBr tablet, cm.$^{-1}$) 3419, 2961, 1512, 1458, 1264, 835

$^1$H-NMR (CDCl$_3$, ppm) 1.29 (s, 9 H), 2.17 (s, 3 H), 3.33 (s, 2 H), 3.47 (s, 2 H), 5.18 (d, J=1.35 Hz, 1 H), 5.37 (d, J=1.35 Hz, 1 H), 6.74~6.78 (m, 2 H), 7.17 (d, J=7.83 Hz, 2 H), 7.29~7.37 (m, 4 H)

Example 61

2-[N-(4-tert-butylbenzyl)-N-methylamino]-2'-hydroxyacetophenone (Compound AD-056), and hydrochloride of Compound AD-056 (Compound AD-057)

N-(4-tert-butylbenzyl)methylamine obtained in Preparation Example 31 or 32 and 2-bromo-2'-hydroxyacetophenone obtained in Preparation Example 16 were used as raw materials and Compound AD-056 was obtained in the same manner as in Example 37. Compound AD-056 was used as a raw material and Compound AD-057 was obtained in the same manner as in Example 38. The physical properties measured of Compound AD-057 were as follows. yellowish white crystal IR (KBr tablet, cm$^{-1}$) 3480, 2963, 2906, 1652, 1617, 1603, 1457, 1366, 1292, 1238 m.p. 95 to 160° C. (After the start of melting, once foamed and swelled. At further increase in temperature, it was liquefied.)

$^1$H-NMR (CDCl$_3$, ppm) 1.27 (s, 9 H), 3.10 (s, 3 H), 4.36~4.56 (m, 2 H×2), 6.86~6.92 (m 1 H), 7.04~7.07 (m, 1 H), 7.36~7.44 (m, 3 H), 7.52~7.58 (m, 3 H), 11.4 (brs, 1 H), 13.2 (brs, 1 H)

Example 62

N-methyl-N-(1-naphthylmethyl)-2-phenyl-2-propenylamine (Compound AD-058), and hydrochloride of Compound AD-058 (Compound AD-059)

0.82 9 (4.80 mmol) of N-methyl-(1-naphthylmethyl) amine obtained in Preparation Example 33 and 0.73 g (6.86 mmol) of sodium carbonate were mixed with 20 ml of N,N-Dimethylformamide, and 15 ml of the N,N-dimethylformamide solution containing 0.90 g (4.57 mmol) of α-bromomethylstyrene obtained in Preparation Example 19 was dropped while stirring the mixture at room temperature. After stirring as it was at room temperature for 15 hours, the mixture was poured into a mixture of ice and a saturated aqueous sodium hydrogen carbonate solution to stop the reaction. The reaction mixture was extracted with 100 ml of ethyl acetate and the organic extract was washed with a saturated aqueous sodium hydrogen carbonate and with saturated saline and dried with anhydrous sodium sulfate. The solvent was distilled off under reduced pressure and the residue was purified by silica gel column chromatography (n-hexane ethyl acetate=30:1) to obtain 1.00 g (yield: 76.1%), of Compound AD-058 as white oily substance. The physical properties measured of Compound AD-058 were as follows.

$^1$H-NMR (CDCl$_3$, ppm) 2.18 (s, 3 H), 3.46 (s, 2 H), 3.89 (s, 2 H), 5.30 (d J=1.35 Hz, 1 H), 5.49 (d, J=1.62 Hz, 1 H), 7.20~7.30 (m, 4 H), 7.36~7.44 (m, 5 H), 7.70~7.82 (m, 2 H), 7.98 (d, J=8.37 Hz, 1 H)

Compound AD-058 was used as a raw material and Compound AD-059 was obtained in the same manner as in Example 38. The physical properties measured of Compound AD-059 were as follows. IR (KBr tablet, cm$^{-1}$) 3462, 3440, 2976, 2957, 2940, 2724, 2690, 2650, 1465, 1446, 899, 800, 781, 709, 690 m.p. 171.8~173.8° C.

$^1$H-NMR (CDCl$_3$, ppm) 2.49 (d, J=4.86 Hz, 3 H), 4.28 (d, J=3.51 Hz, 2 H), 4.51~4.68 (m, 2 H), 5.88 (s, 1 H×2), 7.38~7.44 (m, 5 H), 7.50 (m, 3 H), 7.65~7.73 (m, 1 H), 7.88~7.91 (m, 2 H), 8.09 (d, J=7.02 Hz, 1 H), 12.8 (brs, 1 H)

Example 63

N-methyl-N-(2-naphthylmethyl)-2-phenyl-2-propenylamine (Compound AD-060), and hydrochloride of Compound AD-060 (Compound AD-061)

N-methyl-(2-naphthylmethyl)amine obtained in Preparation Example 34 and α-bromomethylstyrene obtained in Preparation Example 19 were used as raw materials and Compound AD-060 was prepared in the same manner as in Example 62. Compound AD-060 was used as a raw material and Compound AD-061 was obtained in the same manner as in Example 38. The physical properties measured of Compound AD-061 were as follows. white crystal IR (KBr tablet, cm$^{-1}$) 3428, 3056, 2978, 2904, 2693, 2637, 2577, 2543, 1465, 1410, 915, 816, 780, 751, 707 m.p. 162~163.5° C.

$^1$H-NMR (CDCl$_3$, ppm) 2.59 (d, J=5.13 Hz,3 H), 4.07~4.34 (m, 2 H×2), 5.87 (s, 1 H), 5.89 (s, 1 H), 7.35~7.46 (m, 5 H), 7.50~7.65 (m, 2 H), 7.80~7.93 (m, 5 H), 12.9 (brs, 1 H)

Example 64

4'-tert-butyl-2-[N-methyl-N-(2-naphthylmethyl) amino]acetophenone (Compound AD-062), N-methyl-N-(2-naphthylmethyl)-[2-( 4-tert-butylphenyl)-2-propenyl]amine (Compound AD-063), and hydrochloride of Compound AD-063 (Compound AD-064)

N-methyl-(2-naphthylmethyl)amine obtained in Preparation Example 34 and 2-bromo-4'-tert-butylacetophenone obtained in Preparation Example 12 were used as raw materials and Compound AD-062 was obtained in the same manner as in Example 37. Compound AD-062 was used as a raw material and Compound AD-063 was obtained in the same manner as in Example 39. Compound AD-063 was used as a raw material and Compound AD-064 was obtained in the same manner as in Example 38. The physical properties measured of Compound AD-064 were as follows. white crystal IR (KBr tablet, cm$^{-1}$) 3438, 2961, 2904, 2868, 2625, 2547, 1463, 1403, 1364, 922, 840, 823 m.p. 205~206° C.

$^1$H-NMR (CDCl$_3$, ppm) 1.32 (s, 9 H), 2.60 (d, J=4.86 Hz, 2 H), 4.07~4.37 (m, 2 H×2), 5.8 6 (s, 1 H), 5.87 (s, 1 H), 7.28~7.44 (m, 4 H), 7.49~7.59 (m, 2 H), 7.76~7.92 (m, 5 H), 12.8 (brs, 1 H)

Example 65

4'-tert-butyl-2-[N-methyl-N-(1-naphthylmethyl) amino]acetophenone (Compound AD-065), N-methyl-N-(1-naphthylmethyl)-[2-(4-tert-butylphenyl)-2-propenyl]amine (Compound AD-066), and hydrochloride of Compound AD-066 (Compound AD-067)

N-methyl-(1-naphthylmethyl)amine obtained in Preparation Example 33 and 2-bromo-4'-tert-butylacetophenone obtained in Preparation Example 12 were used as raw materials and Compound AD-065 was obtained in the same manner as in Example 37. Compound AD-065 was used as a raw material and Compound AD-066 was obtained in the same manner as in Example 39. Compound AD-066 was used as a raw material and Compound AD-067 was obtained in the same manner as in Example 38. The physical properties measured of Compound AD-067 were as follows. white crystal IR (KBr tablet, cm$^{-1}$) 3439, 2963, 1464, 803, 776 m.p. 189~190° C.

$^1$H-NMR (CDCl$_3$, ppm) 1.33 (s, 9 H), 2.48 (d, J=5.13 Hz, 3 H), 4.29 (d, J=4.05 Hz, 2 H), 4.50~4.67 (m, 2 H), 5.82 (s, 1 H), 5.85 (s, 1 H), 7.35~7.66 (m, 8 H), 7.87~7.93 (m, 2 H), 8.11 (d, J=7.02 Hz, 1 H), 12.7 (brs, 1 H)

Example 66

2-[N-(4-tert-butylbenzyl)-N-methylamino]-2'-acetonaphthone (Compound AD-068), N-(4-tert-butylbenzyl)-N-methyl-[2-(2-naphthyl)-2-propenyl]amine (Compound AD-069), and hydrochloride of Compound AD-069 (Compound AD-070)

N-(4-tert-butylbenzyl)methylamine obtained in Preparation Example 31 or 32 and 2-bromo-2'-acetonaphtone obtained in Preparation Example 35 were used as raw materials and Compound AD-068 was obtained in the same manner as in Example 37. Compound AD-068 was used as a raw material and Compound AD-069 was obtained in the same manner as in Example 39. Compound AD-069 was used as a raw material and Compound AD-070 was obtained in the same manner as in Example 38. The physical properties measured of Compound AD-070 were as follows. white solid IR (KBr tablet, cm$^{-1}$) 3471, 3229, 2963, 2928, 1515, 1465, 863, 815, 755 m.p. 182~183° C.

$^1$(H-NMR (CDCl$_3$, ppm) 1.27 (s, 9 H), 2.55 (s, 3 H), 3.97~4.32 (m, 2 H×2), 5.96 (s, 1 H), 5.99 (s, 1 H), 7.38~7.47 (m, 4 H), 7.4 9~7.57 m, 3 H), 7.81~7.90 (m, 4 H), 12.6 (brs, 1 H)

Example 67

N-(4-tert-butylbenzyl)-N-(2,2,2-trifluoro ethyl)-2-phenyl-2-propenylamine (Compound AD-071)

N,N-dimethylformamide (10 ml) was mixed with 0.10 g (2.44 mmol), of sodium hydride (60% oily), and 7 ml of the N,N-dimethylformamide solution containing 0.50 g (2.32 mmol) of N-(2,2,2-trifluoroethyl)-2-phenyl-2-propenylamine obtained in Preparation Example 36 in was dropped while stirring in an ice bath, and the mixture was stirred at room temperature for 4 days. The reaction mixture was poured into a mixture of ice and a saturated aqueous sodium hydrogen carbonate solution to stop the reaction. The reaction mixture was extracted with 100 ml of ethyl acetate, and the organic extract was washed with a saturated aqueous sodium hydrogen carbonate and with saturated saline and dried with anhydrous sodium sulfate. The solvent was distilled off under reduced pressure, and the residue was purified twice by silica gel column chromatography (first time, n-hexane:ethyl acetated 20:1, second time, chloroform 100%) to obtain 0.15 g (yield: 18.8%) of Compound AD-071. The physical properties measured of Compound AD-071 were as follows. IR (KBr tablet, cm$^{-1}$) 2964, 1271, 1141, 1081

$^1$H-NMR (CDCl$_3$, ppm) 1.23 (s, 9 H), 3.01 (q, J=9.72 Hz, 2 H), 3.62 (s, 2 H), 3.68 (s, 2 H), 5.25 (d, J=1.62 Hz, 1 H), 5.40 (d, J=1.62 Hz, 1 H), 7.01 (d, J=8.37 Hz, 2 H), 7.19~7.29 (m, 7 H)

Example 68

2-[N-(4-tert-butylbenzyl)-N-methylamino]-3',5'-difluoroacetophenone (Compound AD-072), N-(4-tert-butylbenzyl)-N-methyl-[2-(3,5-difluorophenyl)-2-propenyl]amine (Compound AD-073), and hydrochloride of Compound AD-073 (Compound AD-074)

N-(4-tert-butylbenzyl)methylamine obtained in Preparation Example 31 or 32 and 2-bromo-3',5'-difluoroacetophenone obtained in Example 17 were used as raw materials and Compound AD-072 was obtained in the same manner as in Example 37. Compound AD-072 was used as a raw material and Compound AD-073 was obtained in the same manner as in Example 39. Compound AD-073 was used as a raw material and Compound AD-074 was obtained in the same manner as in Example 38. The physical properties measured of Compound AD-074 were as follows. white crystal IR (KBr tablet, cm$^{-1}$) 2966, 1622, 1587, 1468, 1386, 1116, 835 m.p. 191~193° C.

$^1$H-NMR (CDCl$_3$, ppm) 1.32 (s, 9 H), 2.60 (d, J=4.32 Hz, 3 H), 3.87~4.18 (m, 2 H×2), 5.93 (s, 1 H), 6.07 (s, 1 H), 6.79~6.87 (m, 3 H), 7.43~7.50 (m, 4 H), 12.8 (brs, 1 H)

Example 69

2-[N-(4-tert-butylbenzyl)-N-methylamino]-3',4'-difluoroacetophenone (Compound AD-075), N-(4-tert-butylbenzyl)-N-methyl-[2-(3,4-difluorophenyl)-2-propenyl]amine (Compound AD-076), and hydrochloride of Compound AD-076 (Compound AD-077)

N-(4-tert-butylbenzyl)methylamine obtained in Preparation Example 31 or 32 and 2-bromo-3',4'-difluoroacetophenone obtained in Preparation Example 18 were used as raw materials and Compound AD-075 was obtained in the same manner as in Example 37. Compound AD-075 was used as a raw material and Compound AD-076 was obtained in the same manner as in Example 39. Compound AD-076 was used as a raw material and Compound AD-077 was obtained in the same manner as in Example 38. The physical properties measured of Compound AD-077 were as follows. white crystal IR (KBr tablet, cm$^{-1}$) 3433, 3378, 2967, 2686, 2656, 2629, 1521, 1273 m.p. 183~184° C.

$^1$H-NMR (CDCl$_3$, ppm) 1.31 (s, 9 H), 2.60 (d, J=5.13 Hz, 3 H), 3.88~4.18 (m 2 H×2), 5.84 (s, 1 H), 5.96 (d, J=2.43 Hz 1 Hz), 7.09~7.22 (m, 3 H), 7.39~7.50 (m,4 H), 12.8 (brs, 1 H)

Example 70

N-[4-(1-methyl-1-phenylethyl)benzyl]-N-methyl-2-phenyl-2-propenylamine (Compound AD-078), and hydrochloride of Compound AD-078 (Compound AD-079)

Using N-methyl-4-(1-methyl-1-phenylethyl)benzylamine obtained in Preparation Example 37 or 38 and α-bromomethylstyrene obtained in Preparation Example 19 as raw materials, Compound AD-079 was obtained through Compound AD-078 in the same manner as in Example 62. The physical properties measured of Compound AD-079 were as follows. white crystal IR (KBr tablet, cm$^{-1}$) 3449, 3234, 2963, 2925, 1515, 1467, 1386, 1202 m.p. 140~141° C.

$^1$H-NMR (CDCl$_3$, ppm) 1.66 (s, 3 H×2), 2.52 (d, J=4.32 Hz, 3 H), 3.89~4.22 (m, 2 H×2), 5.84 (s, 1 H), 5.85 (s, 1 H), 7.15~7.44 (m, 14 H), 12.6 (brs, 1 H)

Example 71

2-[N-(4-tert-butylbenzyl)-N-methylamino]-4'-methylacetophenone (Compound AD-080), N-(4-tert-butylbenzyl)-N-methyl-[2-(4-methylphenyl)-2-propenyl]amine (Compound AD-081), and hydrochloride of Compound AD-081 (Compound AD-082)

2-bromo-4'-methylacetophenone obtained in Preparation Example 21 and N-(4-tert-butylbenzyl)methylamine obtained in Preparation Example 31 or 32 were used as raw materials and Compound AD-080 was obtained in the same manner as in Example 37. Compound AD-080 was used as a raw material and Compound AD-081 was obtained in the same manner as in Example 39. Compound AD-081 was used as a raw material and Compound AD-082 was obtained in the same manner as in Example 38. The physical properties measured of Compound AD-082 were as follows. m.p. 180.5~182.5° C.

$^1$H-NMR (CDCl$_3$, ppm) 1.30 (s, 9 H), 2.37 (s, 3 H), 2.52 (d, J=4.86 Hz, 3 H), 3.94 (dd, J=12.96 Hz, 6.21 Hz, 1 H), 4.05 (dd, J=13.77 Hz, 4.32 Hz, 1 H), 4.09~4.30 (m, 2 H), 5.81 (s, 2 H), 7.20 (d, J=8.10 Hz, 2 H), 7.27 (d, J=8.10 Hz, 2 H), 7.41 (d, J=6.48 Hz, 2 H), 7.47 (d, J=6.48 Hz, 2 H), 12.55 (br, 1 H)

Example 72

2-[N-(4-tert-butylbenzyl)-N-methylamino]-3'-fluoroacetophenone (Compound AD-083), N-(4-tert-butylbenzyl)-N-methyl-[2-(3-fluorophenyl)-2-propenyl]amine (Compound AD-084), and hydrochloride of Compound AD-084 (Compound AD-085)

2-bromo-3'-fluoroacetophenone obtained in Preparation Example 22 and N-(4-tert-butylbenzyl)methylamine obtained in Preparation Example 31 or 32 were used as raw materials and Compound AD-083 was obtained in the same manner as in Example 37. Compound AD-083 was used as a raw material and Compound AD-084 was obtained in the same manner as in Example 39. Compound AD-084 was used as a raw material and Compound AD-085 was obtained in the same manner as in Example 38. The physical properties measured of Compound AD-085 were as follows. m.p. 172.5~174° C.

$^1$H-NMR (CDCl$_3$, ppm) 1.31 (s, 9 H), 2.57 (d, J=4.86 Hz, 3 H), 3.92~4.23 (m, 4 H), 5.89 (s, 1 H), 5.98 (s, 1 H), 7.02~7.14 (m, 2 H), 7.16 (d, J=7.83 Hz, 1 H), 7.33~7.53 (m, 5 H), 12.69 (br, 1 H)

Example 73

2-[N-(4-tert-butylbenzyl)-N-methylamino]-2',4'-dichloroacetophenone (Compound AD-086), N-(4-tert-butylbenzyl)-N-methyl-[2-(2,4-dichlorophenyl)-2-propenyl]amine (Compound AD-087), and hydrochloride of Compound AD-087 (Compound AD-088)

2-bromo-2', 4'-dichloroacetophenone obtained in Preparation Example 26 and N-(4-tert-butylbenzyl)methylamine obtained in Preparation Example 31 or 32 were used as raw materials and Compound AD-086 was obtained in the same manner as in Example 37. Compound AD-086 was used as a raw material and Compound AD-087 was obtained in the same manner as in Example 39. Compound AD-087 was used as a raw material and Compound AD-088 was obtained in the same manner as in Example 38. The physical properties measured of Compound AD-088 were as follows. m.p. 186.5~188° C.

$^1$H-NMR (CDCl$_3$, ppm) 1.31 (s, 9 H), 2.63 (d, J=4.86 Hz, 3 H), 3.94 (dd, J=14.04 Hz, 4.59 Hz, 1 H), 4.01~4.18 (m, 3 H), 5.73 (s, 1 H), 6.17 (s, 1 H), 7.24~7.36 (m, 2 H), 7.42 (s, 4 H), 7.45 (d, J=1.35 Hz, 1 H), 12.72 (br, 1 H)

Example 74

N-(4-tert-butylbenzyl)-N-methyl-3-methyl-2-phenyl-2-butenylamine (Compound AD-089), and hydrochloride of Compound AD-089 (Compound AD-090)

Using Compound AD-001 obtained in Example 37 as a raw material and using isopropyltriphenylphosphoniumiodide instead of methyltriphenylphosphoniumbromide, Compound AD-089 was obtained in the same manner as in Example 39. Compound AD-089 was used as a raw material and Compound AD-090 was obtained in the same manner as in Example 38. The physical properties measured of Compound AD-090 were as follows. m.p. 163~165.5° C.

$^1$H-NMR (CDCl$_3$, ppm) 1.29 (s, 9 H), 1.74 (s, 3 H), 1.93 (s, 3 H)3 2.43 (d, J=5.13 Hz, 3 H), 3.80~3.98 (m, 3 H), 4.24 (dd, J=14.04 Hz, 3.24 Hz, 1 H), 7.20 (d, J=6.75 Hz, 2 H), 7.28~7.49 (m, 7 H), 12.18 (br, 1 H)

Example 75

2-[N-(4-tert-butylbenzyl)-N-methylamino]-2'-chloroacetophenone (Compound AD-091), N-(4-tert-butylbenzyl)-N-methyl-[2-(2-chlorophenyl)-2-propenyl]amine (Compound AD-092), and hydrochloride of Compound AD-092 (Compound AD-093)

2-bromo-2'-chloroacetophenone obtained in Preparation Example 23 and N-(4-tert-butylbenzyl)methylamine obtained in Preparation Example 31 or 32 were used as raw materials and Compound AD-091 was obtained in the same manner as in Example 37. Compound AD-091 was used as a raw material and Compound AD-092 was obtained in the same manner as in Example 39. Compound AD-092 was used as a raw material and Compound AD-093 was obtained in the same manner as in Example 38. The physical properties measured of Compound AD-093 were as follows. m.p. 184.5~187° C.

$^1$H-NMR (CDCl$_3$, ppm) 1.30 (s, 9 H), 2.61 (d, J=4.86 Hz, 3 H), 3.95~4.19 (m, 4 H), 5.73 (s, 1 H), 6.12 (s, 1 H), 7.30~7.50 (m, 8 H), 12.65 (br, 1 H)

Example 76

2-[N-(4-tert-butylbenzyl)-N-methylamino]-3',4'-dichloroacetophenone (Compound AD-094), N-(4-tert-butylbenzyl)-N-methyl-[2-(3,4-dichlorophenyl)-2-propenyl]amine (Compound AD-095), and hydrochloride of Compound AD-095 (Compound AD-096)

2-bromo-3',4'-dichloroacetophenone obtained in Preparation Example 27 and N-(4-tert-butylbenzyl)methylamine obtained in Preparation Example 31 or 32 were used as raw materials and Compound AD-094 was obtained in the same manner as in Example 37. Compound AD-094 was used as a raw material and Compound AD-095 was obtained in the same manner as in Example 39. Compound AD-095 was used as a raw material and Compound AD-096 was obtained in the same manner as in Example 38. The physical properties measured of Compound AD-096 were as follows. m.p. 181~183.5° C.

$^1$H-NMR (CDCl$_3$, ppm) 1.31 (s, 9 H), 2.61 (d, J=4.86 Hz, 3 H), 3.94 (dd, J=13.77 Hz, J=4.86 Hz, 1 H), 4.04~4.22 (m, 3 H), 5.89 (s, 1 H), 6.00 (s, 1 H), 7.23 (dd, J=8.37 Hz, J=2.43 Hz, 1 H), 7.40~7.53 (m, 8 H), 12.75 (br, 1 H)

Example 77

2-[N-(4-tert-butylbenzyl)-N-methylamino]-3'-methoxyacetophenone (Compound AD-097), N-(4-tert-butylbenzyl)-N-methyl-[2-(3-methoxyphenyl)-2-propenyl]amine (Compound AD-098), and hydrochloride of Compound AD-098 (Compound AD-099)

3'-methoxyacetophenone was used as a raw material and 2-bromo-3'-methoxyacetophenone was obtained in the same manner as in Preparation Example 1. 2-bromo-3'-methoxyacetophenone and N-(4-tert-butylbenzyl)methylamine were used as raw materials and Compound AD-097 was obtained in the same manner as in Example 37. Compound AD-097 was used as a raw material and Compound AD-098 was obtained in the same manner as in Example 39. Compound AD-098 was used as a raw material and Compound AD-099 was obtained in the same manner as in Example 38. The physical properties measured of Compound AD-099 were as follows. m.p. 135.5~137.5° C.

$^1$H-NMR (CDCl$_3$, ppm) 1.30 (s, 9 H), 2.54 (d, J=4.86 Hz, 3 H), 3.83 (s, 3 H), 3.90~4.22 (m, 4 H), 5.85 (s, 1 H), 5.87 (s, 1 H), 6.83~6.98 (m, 3 H), 7.33 (t, J=7.83 Hz, 1 H), 7.42 (d, J=6.48 Hz, 2 H), 7.46 (d, J=6.48 Hz, 2 H), 12.60 (br, 1 H)

Example 78

2-[N-(4-tert-butylbenzyl)-N-methylamino]-4'-piperidinoacetophenone (Compound AD-100), N-(4-tert-butylbenzyl)-N-methyl-[2-(4-piperidinophenyl)-2-propenyl]amine (Compound AD-101), and hydrochloride of Compound AD-101 (Compound AD-102)

4'-piperidinoacetophenone was used as a raw material and 2-bromo-4'-piperidinoacetophenone was obtained in the same manner as in Preparation Example 1. 2-bromo-4'-piperidinoacetophenone and N-(4-tert-butylbenzyl)methylamine were used as raw materials and Compound AD-100 was obtained in the same manner as in Example 37. Compound AD-100 was used as a raw material and Compound AD-101 was obtained in the same manner as in Example 39. Compound AD-101 was used as a raw material and Compound AD-102 was obtained in the same manner as in Example 38. The physical properties measured of Compound AD-102 were as follows. m.p. 126 to 128° C. (decomposition)

$^1$H-NMR (CDCl$_3$, ppm) 1.30 (s, 9 H), 1.50~1.85 (m, 6 H), 2.51 (s, 3 H), 3.23 (brs 4 H), 3.85~4.25 (m, 4 H), 5.66 (s, 1 H), 5.73 (s, 1 H), 6.94 (br, 1 H) 7.23~7.35 (m, 3 H), 7.42 (d, J=8.37 Hz, 2 H), 7.48 (d, J=8.37 Hz, 2 H), 12.41 (br, 1 H)

Example 79

2-[N-(4-tert-butylbenzyl)-N-methylamino]-4'-cyanoacetophenone (Compound AD-103), 4-[1-{N-(4-tert-butylbenzyl)-N-methylamino}methyl]-vinylbenzonitrile (Compound AD-104), and hydrochloride of Compound AD-104 (Compound AD-105)

2-bromo-4'-cyanoacetophenone obtained in Preparation Example 24 and N-(4-tert-butylbenzyl)methylamine obtained in Preparation Example 31 or 32 were used as raw materials and Compound AD-103 was obtained in the same manner as in Example 37. Compound AD-103 was used as a raw material and Compound AD-104 was obtained in the same manner as in Example 38. Compound AD-104 was used as a raw material and Compound AD-105 was obtained in the same manner as in Example 39. The physical properties measured of Compound AD-105 were as follows. m.p. 171 to 173 ° C.

$^1$H-NMR (CDCl$_3$, ppm) 1.32 (s, 9 H), 2.61 (d, J=4.32 Hz, 3 H), 3.95 (dd, J=14.04 Hz, J=5.94 Hz, 1 H), 4.05~4.28 (m, 3 H), 5.97 (s, 1 H), 6.11 (s, 1 H), 7.36~7.60 (m, 6 H), 7.70 (d, J=8.37 Hz, 2 H), 12.81 (br, 1 H)

Example 80 ethyl 4-[2-{N-(4-tert-butylbenzyl)-N-methylamino}acetyl]benzoate (compound AD-106), ethyl 4-[1-{N-(4-tert-butylbenzyl)-N-methylamino}methyl]vinylbenzoate (Compound AD-107), and hydrochloride of Compound AD-107 (Compound AD-108)

Ethyl 4-(2-bromoacetyl)benzoate obtained in Preparation Example 25 and N-(4-tert-butylbenzyl)methylamine obtained in Preparation Example 31 or 32 were used as raw materials and Compound AD-106 was obtained in the same manner as in Example 37. Compound AD-106 was used as a raw material and Compound AD-107 was obtained in the same manner as in Example 39. Compound AD-107 was used as a raw material and Compound AD-108 was obtained in the same manner as in Example 38. The physical properties measured of Compound AD-108 were as follows. m.p. 181 to 183° C.

$^1$H-NMR (CDCl$_3$, ppm)

1.31 (s, 9 H), 1.40 (t, J=7.02 Hz, 3 H), 2.55 (d, J=4.86 Hz, 3 H), 3.95~4.28 (m, 4 H) 4.39 (q, J=7.02 Hz, 2 H), 5.95 (s, 1 H) 6.03 (s, 1 H), 7.37~7.52 (m, 6 H) 8.07 (d, J=8.64 Hz, 2 H), 12.77 (br, 1 H)

Example 81

4-[1-{N-(4-tert-butylbenzyl)-N-methylamino}methyl]vinylbenzoic acid (Compound AD-109), and hydrochloride of Compound AD-109 (Compound AD-110)

470 mg (1.34 mmol) of Compound AD-107 obtained in Example 80 above was dissolved in 5 ml of methanol, and 5 ml of in sodium hydroxide was added thereto, and the mixture was heated under reflux for 3 hours. Then, the methanol was distilled off, and the residue was extracted with 50 ml and 30 ml, respectively, of ethyl acetate after adjusting to pH 7 with 1N hydrochloric acid. The organic extract was dried and concentrated under reduced pressure to obtain Compound AD-109. Compound AD-109 was used as a raw material and Compound AD-110 was obtained in the same manner as in Example 38. The physical properties measured of Compound AD-110 were as follows. m.p. 217 to 219° C. (Decomposition)

$^1$H-NMR (CDCl$_3$+CD$_3$OD, ppm) 1.31 (s, 9 H), 2.61 (s 3 H), 4.14 (brs, 4 H), 5.93 (s, 2 H), 7.36~7.45 (m, 4 H), 7.44 (d, J=8.37 Hz, 2 H), 8.06 (d, J=8.37 Hz, 2 H)

Example 82

N-(4-tert-butylbenzyl)-N-ethyl-2-phenyl-2-propenylamine (Compound AD-111), and hydrochloride of Compound AD-111 (Compound AD-112)

N-ethyl-2-phenyl-2-propenylamine obtained in Preparation Example 20 and 4-tert-butylbenzylbromide were used as raw materials and Compound AD-111 was obtained in the same manner as in Example 62. Compound AD-111 was used as a raw material and Compound AD-112 was obtained in the same manner as in Example 38. The physical properties measured of Compound AD-112 were as follows. m.p. 158 to 160.5° C.

$^1$H-NMR (CDCl$_3$, ppm) 1.30 (s, 9 H), 1.40 (t, J=7.29 Hz, 3 H), 2.96 (m, 2 H), 3.93~4.23 (m, 4 H), 5.83 (d, J=1.35 Hz, 1 H), 5.96 (d, J=1.35 Hz, 1 H), 7.30~7.46 (m, 7 H), 7.50 (d, J=7.83 Hz, 2 H), 12.37 (br, 1 H)

Example 83

N-(4-tert-butylbenzyl)-N-isopropyl-2-phenyl-2-propenylamine (Compound AD-113), and hydrochloride of Compound AD-113 (Compound AD-114)

N-isopropyl-2-phenyl-2-propenylamine obtained in Preparation Example 28 and 4-tert-butylbenzylamine obtained in Preparation Example 31 or 32 were used as raw materials and Compound AD-113 was obtained in the same manner as in Example 62. Compound AD-113 was used as a raw material and Compound AD-114 was obtained in the same manner as in Example 38. The physical properties measured of Compound AD-114 were as follows. Amorphous $^1$H-NMR (CDCl$_3$, ppm) 1.30 (s, 9 H), 1.40 (d J=6.75 Hz, 3 H), 1.44 (d, J=6.75 Hz, 3 H), 3.66 (m, 1 H), 3.88~4.18 (m, 4 H), 5.84 (s, 1 H), 6.24 (s, 1 H), 7.28~7.45 (m, 5 H), 7.40 (d, J=8.10 Hz, 2 H), 7.66 (d, J=8.10 Hz, 2 H), 12.15 (br, 1 H)

Example 84

N-(4-tert-butylbenzyl)-N-cyclopropyl-2-phenyl-2-propenylamine (Compound AD-115), and hydrochloride of Compound AD-115 (Compound AD-116)

N-cyclopropyl-2-phenyl-2-propenylamine obtained in Preparation Example 29 and 4-tert-butylbenzylamine obtained in Preparation Example 31 or 32 were used as raw materials and Compound AD-115 was obtained in the same manner as in Example 37. Compound AD-115 was used as a raw material and Compound AD-116 was obtained in the same manner as in Example 38. The physical properties measured of Compound AD-116 were as follows. m.p. 160.5 to 163.5° C. (Decomposition)

$^1$H-NMR (CDCl$_3$, ppm)

0.46 (m, 1 H), 0.57 (m, 1 H), 1.26 (m, 1 H), 1.31 (s, 9 H), 1.55 (m, 1 H), 2.00 (m, 1 H), 4.06~4.33 (m, 4 H), 5.84 (s, 2 H), 7.38 (s, 5 H), 7.40 (d, J=8.64 Hz, 2 H), 7.45 (d, J=8.64 Hz, 2 H), 12.28 (br, 1 H)

Examples of Composition of the Present Invention

Examples of composition of the invention containing the novel amine derivatives or salts thereof obtained in the examples described above will be described below.

Examples 85, 86

Haft of Toothbrush

According to the formulations shown in Table 3, small balls of polystyrene and Compound PR-1258 or PR-1540 were mixed and melt molded to produce a haft of toothbrush.

TABLE 3

(Formulation)

| Ingredient | Compounding Amount (part by weight) | |
|---|---|---|
| | Example 85 | Example 86 |
| Small balls of polystyrene | 99 | 99 |
| Compound PR-1258 | 1 | — |
| Compound PR-1540 | — | 1 |

Examples 87, 88

Haft of Toothbrush

According to the formulations shown in Table 4, small balls of polystyrene and Compound AD-007 or AD-010 were mixed and melt molded to produce a haft of toothbrush.

TABLE 4

(Formulation)

| Ingredient | Compounding Amount (part by weight) | |
|---|---|---|
| | Example 87 | Example 88 |
| Small balls of polystyrene | 99 | 99 |
| Compound AD-007 | 1 | — |
| Compound AD-010 | — | 1 |

Examples 89, 99

Ointment for athlete's foot (tinea pedis)

According to the formulations shown in Table 5, the respective formulation ingredients were weighed and mixed in a kneader to produce an ointment for athlete's food (tinea pedis).

TABLE 5

(Formulation)

| Ingredient | Compounding Amount (part by weight) | |
|---|---|---|
| | Example 89 | Example 90 |
| Vaseline | 99 | — |
| Water-absorbing ointment | — | 99 |
| Compound PP-1484 | 1 | — |
| Compound PR-1418 | — | 1 |

Examples 91, 92

Ointment for athlete's foot (tineapedis)

According to the formulations shown in Table 6, the respective formulation ingredients were weighed and mixed in a kneader to produce an ointment for athlete's food (tinea pedis).

TABLE 6

(Formulation)

| Ingredient | Compounding Amount (part by weight) | |
|---|---|---|
| | Example 91 | Example 92 |
| Vaseline | 99 | — |
| Water-absorbing ointment | — | 99 |
| Compound AD-013 | 1 | — |
| Compound AD-016 | — | 1 |

Examples 93, 94

Liquid Preparation

The formulation ingredients shown in Table 7 were stirred and solubilized to obtain a liquid preparation.

TABLE 7

(Formulation)

| Ingredient | Compounding Amount (part by weight) | |
|---|---|---|
| | Example 93 | Example 94 |
| Ethanol | 92 | 92 |
| Alkyl methacrylate copolymer | 2 | 2 |
| Propylene glycol | 5 | 5 |
| Compound PR-1554 | 1 | — |
| Compound PR-2159 | — | 1 |

Examples 95, 96

Liquid Preparation

The formulation ingredients shown in Table 8 were stirred and solubilized to obtain a liquid preparation.

TABLE 8

(Formulation)

| Ingredient | Compounding Amount (part by weight) | |
|---|---|---|
| | Example 95 | Example 96 |
| Ethanol | 92 | 92 |
| Alkylester methacrylate copolymer | 2 | 2 |
| Propylene glycol | 5 | 5 |
| Compound AD-019 | 1 | — |
| Compound AD-022 | — | 1 |

Test Example

The novel amine derivatives or salts thereof obtained in the examples described above in accordance with the present invention were evaluated for their antimycotic activity by test examples as follows.

Test Example 1

Measurement of Antimycotic Activity (Measurement of Minimum Inhibitory Concentration (MIC))

The antimycotic activity of the compounds of the invention against dermatophyte was examined.

More particularly, the test dermatophyte strains shown in Tables 9 and 10 below were cultivated in advance on a slant culture of Sabouraud's agar medium (manufactured by Nissui Seiyaku Co., Ltd.; 1.0% peptone, 4.0% glucose, 1.5% agar, pH=5.9) at 27° C. for 2 weeks to allow them to grow conidia sufficiently. Then, sterilized physiological saline containing 0.05 weight/volume % of Tween 80 was added to the culture and while rubbing the surface of the culture with a platinum loop, the conidia were separated and caused to float. Using a hemocytometer, the filtrate was adjusted with sterilized physiological saline such that the concentration of conidia was $10^6$ cells/ml, which was used as a test microbe liquid.

On the other hand, PR compounds and AD compounds (test drugs) of the present invention obtained in the examples described above were taken each in an amount of 10 mg, and 1 ml of dimethyl sulfoxide was added thereto to form a stock solution, of which 500 µl was taken and 500 µl of dimethyl sulfoxide was added thereto to prepare a 2-fold dilution. The same operation was repeated to prepare 13-stages ranging from 10 to 0.0025 mg/ml (final concentration of test system 100 to 0.025 µg/ml) of diluted drug solutions. Solutions with various diluted concentrations of test drug were each dispensed in sterilized petri dish with an amount of 100 µl. Then, 10 ml of sterile-dissolved Sabouraud's agar medium (1.0% peptone, 4.0% glucose, 1.5% agar, pH=5.9) was added, well mixed and solidified. Then, 5 µl of the test microbe solution previously adjusted were added using a microplanter, respectively.

The cultivation was carried out at 27° C. for 1 week and the minimum drug concentration (µg/ml) which clearly inhibits visible growth was regarded as an MIC value. The results are shown in Table 9 for PR compounds and in Table 10 for AD compounds, respectively. In the column of Compound No. in Tables 9 and 10, "PR-" or "AD-" were omitted.

TABLE 9-1

MIC values of PR Compounds against dermatophytes

| Dermatophyte\ | Minimum Inhibitory Concentration (µg/ml) | | | | | | |
|---|---|---|---|---|---|---|---|
| PR Compound No | 1258 | 1533 | 1540 | 1491 | 1430 | 1505 | 1484 |
| T. mentagrophytes IF05811 | 1.56 | 0.39 | 0.1 | 0.39 | 0.39 | 1.56 | 0.1 |
| T. mentagrophytes IF07552 | 0.78 | 1.56 | 0.39 | 0.39 | 0.39 | 1.56 | 0.2 |
| T. mentagrophytes TIMM1177 | 0.78 | 0.39 | 0.39 | 0.39 | 0.39 | 1.56 | 0.1 |
| T. mentagrophytes TIMM1189 | 0.78 | 0.39 | 0.1 | 0.39 | 0.39 | 1.56 | 0.39 |
| T. rubrum IF05808 | 0.39 | 0.39 | 0.1 | 0.1 | 0.39 | 0.39 | 0.1 |
| T. rubrum IF09185 | 0.78 | 0.39 | 0.1 | 0.39 | 0.39 | 1.56 | 0.1 |
| T. violaceum TIMM1264 | 1.56 | 0.39 | 0.1 | 0.39 | 0.39 | 0.39 | 0.1 |
| M. gypseum IF08231 | 1.56 | 6.25 | 1.56 | 6.25 | 6.25 | 6.25 | 0.39 |
| M. canis TIMM0760 | 0.39 | 0.39 | 0.1 | 0.1 | 0.39 | 0.39 | 0.1 |

TABLE 9-2

MIC values of PR Compounds against dermatophytes

| Dermatophyte\ | Minimum Inhibitory Concentration (µg/ml) | | | | | | |
|---|---|---|---|---|---|---|---|
| PR Compound No | 1439 | 1418 | 1641 | 1554 | 1712 | 1705 | 2173 |
| T. mentagrophytes IF05811 | 0.39 | 0.39 | 12.5 | 1.56 | 6.25 | 0.78 | 1.56 |
| T. mentagrophytes IF07552 | 0.39 | 0.39 | 12.5 | 0.78 | 6.25 | 1.56 | 1.56 |
| T. mentagrophytes TIMM1177 | 1.56 | 0.39 | 12.5 | 0.78 | 6.25 | 1.56 | 1.56 |
| T. mentagrophytes TIMM1189 | 0.39 | 0.39 | 25 | 1.56 | 12.5 | 1.56 | 0.78 |
| T. rubrum IF05808 | 0.39 | 0.1 | 6.25 | 0.39 | 1.56 | 0.2 | 1.56 |
| T. rubrum IF09185 | 0.39 | 0.39 | 6.25 | 0.39 | 1.56 | 0.39 | 0.78 |
| T. violaceum TIMM1264 | 0.39 | 0.1 | 25 | 1.56 | 6.25 | 0.78 | 1.56 |
| M. gypseum IF08231 | 6.25 | 6.25 | 25 | 0.78 | 6.25 | 1.56 | 6.25 |
| M. canis TIMM0760 | 0.39 | 0.1 | 12.5 | 0.39 | 3.12 | 0.39 | 0.39 |

TABLE 9-3

MIC values of PR Compounds against dermatophytes

| Dermatophyte\ | Minimum Inhibitory Concentration ($\mu$g/ml) | | | |
|---|---|---|---|---|
| PR Compound No | 2159 | 1620 | 1606 | 1672 |
| T. mentagrophytes IF05811 | 0.2 | 12.5 | 25 | 3.12 |
| T. mentagrophytes IF07552 | 0.2 | 6.25 | 50 | 1.56 |
| T. mentagrophytes TIMM1177 | 0.2 | 12.5 | 50 | 3.12 |
| T. mentagrophytes TIMM1189 | 0.1 | 12.5 | 50 | 3.12 |
| T. rubrum IF05808 | 0.1 | 6.25 | 25 | 0.78 |
| T. rubrum IF09185 | 0.1 | 12.5 | 50 | 1.56 |
| T. violaceum TIMM1264 | 0.2 | 12.5 | 50 | 3.12 |
| M. gypseum IF08231 | 0.2 | 25 | 25 | 3.12 |
| M. canis TIMM0760 | 0.05 | 12.5 | 25 | 1.56 |

TABLE 10-1

MIC values of AD Compounds against dermatophytes

| Dermatophyte\ | Minimum Inhibitory Concentration ($\mu$g/ml) | | | | | | |
|---|---|---|---|---|---|---|---|
| AD Compound No | 007 | 010 | 013 | 016 | 019 | 022 | 025 |
| T. mentagrophytes IF05811 | 1.56 | 1.56 | 1.56 | 0.39 | 3.12 | 0.39 | 0.1 |
| T. mentagrophytes IF07552 | 1.56 | 0.39 | 1.56 | 0.39 | 3.12 | 0.39 | 0.1 |
| T. mentagrophytes TIMM1177 | 1.56 | 1.56 | 1.56 | 0.39 | 3.12 | 0.1 | 0.1 |
| T. mentagrophytes TIMM1189 | 1.56 | 1.56 | 1.56 | 0.39 | 6.25 | 0.39 | 0.1 |
| T. rubrum IF05808 | 1.56 | 0.2 | 1.56 | 0.1 | 1.56 | 0.1 | 0.1 |
| T. rubrum IF09185 | 1.56 | 0.2 | 0.78 | 0.39 | 3.12 | 0.1 | 0.1 |
| T. violaceum TIMM1264 | 0.39 | 0.2 | 1.56 | 0.39 | 6.25 | 0.1 | 0.1 |
| M. gypseum IF08231 | 25 | 12.5 | 6.25 | 0.39 | 6.25 | 0.39 | 0.39 |
| M. canis TIMM0760 | 1.56 | 0.2 | 1.56 | 0.1 | 3.12 | 0.1 | 0.1 |

TABLE 10-2

MIC values of AD Compounds against dermatophytes

| Dermatophyte\ | Minimum Inhibitory Concentration ($\mu$g/ml) | | | | | | |
|---|---|---|---|---|---|---|---|
| AD Compound No | 028 | 033 | 037 | 043 | 046 | 052 | 057 |
| T. mentagrophytes IF05811 | 6.25 | 6.25 | 1.56 | 1.56 | 6.25 | 0.39 | 12.5 |
| T. mentagrophytes IF07552 | 3.12 | 6.25 | 1.56 | 1.56 | 6.25 | 0.78 | 12.5 |
| T. mentagrophytes TIMM1177 | 6.25 | 12.5 | 1.56 | 1.56 | 12.5 | 0.78 | 12.5 |
| T. mentagrophytes TIMM1189 | 6.25 | 12.5 | 3.12 | 1.56 | 12.5 | 0.78 | 12.5 |
| T. rubrum IF05808 | 3.12 | 3.12 | 0.78 | 0.2 | 1.56 | 0.39 | 3.12 |
| T. rubrum IF09185 | 3.12 | 3.12 | 0.78 | 0.78 | 3.12 | 0.39 | 6.25 |
| T. violaceum TIMM1264 | 6.25 | 12.5 | 3.12 | 1.56 | 12.5 | 1.56 | 6.25 |
| M. gypseum IF08231 | 6.25 | 12.5 | 3.12 | 1.56 | 12.5 | 0.39 | 12.5 |
| M. canis TIMM0760 | 3.12 | 6.25 | 0.78 | 0.78 | 6.25 | 0.39 | 6.25 |

TABLE 10-3

MIC values of AD Compounds against dermatophytes

| Dermatophyte\ | MIC ($\mu$g/ml) | | |
|---|---|---|---|
| AD Compound No | 074 | 077 | 079 |
| T. mentagrophytes IF05811 | 0.1 | 3.12 | 0.1 |
| T. mentagrophytes IF07552 | 0.2 | 3.12 | 0.1 |
| T. mentagrophytes TIMM1177 | 0.1 | 1.56 | 0.1 |
| T. mentagrophytes TIMM1189 | 0.1 | 1.56 | 0.1 |
| T. rubrum IF05808 | 0.1 | 1.56 | 0.05 |
| T. rubrum IF09185 | 0.1 | 1.56 | 0.1 |
| T. violaceum TIMM1264 | 0.39 | 1.56 | 0.2 |
| M. gypseum IF08231 | 0.2 | 12.5 | 0.1 |
| M. canis TIMM0760 | 0.1 | 1.56 | 0.1 |
| A. alternate TIMM1289 | — | — | 6.25 |

INDUSTRIAL APPLICABILITY

The amine derivative represented by general formula (1) and salts thereof of the present invention have an excellent antimycotic effect and are very useful as an antimycotic agent, an antimycotic composition, a pharmaceutical composition and so forth.

What is claimed is:

1. An amine compound selected from formula (1) below or salts thereof:

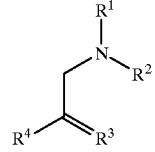

(1)

in the formula (1) above, $R^1$ represents a linear $C_{1-5}$ alkyl group, a branched $C_{1-5}$ alkyl group, or a cyclic $C_{1-5}$ alkyl group, said $C_{1-5}$ alkyl group may be halogenated;

$R^2$ represents a group represented by the formula (a), (b), (c), (d), or (e)

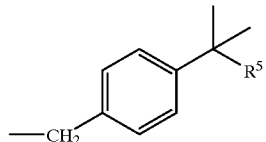

(a)

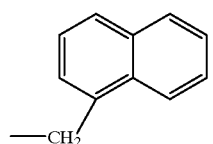

(b)

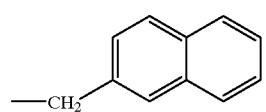

(c)

-continued

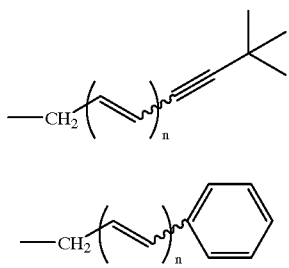
(d)

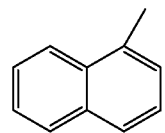
(e)

("~~~" indicates that the arrangement of double bond may be either cis or trans)

(provided that $R^5$ in the formula (a) is a linear $C_{1-4}$ alkyl group or a phenyl group and n in the formula (d) or (e) is an integer of 1 to 3);

$R^3$ is an oxygen atom or a group represented by the formula (f) below;

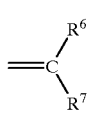
(f)

$R^6$ and $R^7$ independently represents a hydrogen atom, a linear $C_{1-4}$ alkyl group, a branched $C_{1-4}$ alkyl group or a cyclic $C_{1-4}$ alkyl group; R represents a group represented by the formula (g), (h), or (i),

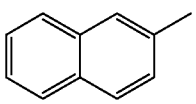
(g)

(h)

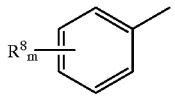
(i)

in the formula (i), $R^8$ is a substituent group which substitutes a hydrogen atom in the phenyl group in the formula (1) and represents a linear $C_{1-7}$ alkyl group, a branched $C_{1-7}$ alkyl group, a cyclic $C_{1-7}$ alkyl group, a halogen atom, a linear $C_{1-4}$ alkoxy group, a branched $C_{1-4}$ alkoxy group, a cyclic $C_{1-4}$ alkoxy group, a nitro group, an amino group optionally substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO—$; and $R^9$ represents a linear $C_{1-4}$ alkyl group, a branched $C_{1-4}$ alkyl group or a cyclic $C_{1-4}$ alkyl group, in which three of $R^9$ may be the same or different; and m of $R^8$ may be the same or different; m is an integer of 0 to 5.

2. An amine compound selected from formula (1) or salts thereof as claimed in claim 1, wherein $R^1$ is a linear $C_{1-5}$ alkyl group, a branched $C_{1-5}$ alkyl group or a cyclic $C_{1-5}$ alkyl group, $R^2$ is a group represented by the formula (d) or (e), and $R^4$ is a group represented by the formula (i).

3. An amine compound selected from formula (1) or salts thereof as claimed in claim 2, wherein represented by general formula (1) $R^1$ is a methyl group, an ethyl group, an iso-propyl group, or a cyclopropyl group, $R^3$ is a carbon atom to which an oxygen atom or two hydrogen atoms are added, and $R^8$ is a methyl group, a tert-butyl group, a fluorine atom, a chlorine atom, a bromine atom, a methoxy group, a nitro group, an amino group, a cyano group, an ethoxycarbonyl group, a hydroxyl group, or a tert-butyldimethylsilyl group.

4. An amine compound selected from formula (1) or salts thereof as claimed in claim 2, which is:

Trans-2-[N-(6,6-dimethyl-2-hepten-4-ynyl)-N-methylamino]acetophenone;

Trans-N-(6,6-dimethyl-2-hepten-4-ynyl)-N-methyl-2-phenyl-2-propenylamine;

Trans-2-[N-(6,6-dimethyl-2-hepten-4-ynyl)-N-methylamino]-2'-methylacetophenone;

Trans-N-(6,6-dimethyl-2-hepten-4-ynyl)-N-methyl-[2-(o-tolyl)-2-propenyl]amine;

Trans-2-[N-(6,6-dimethyl-2-hepten-4-ynyl)-N-methylamino]-3'-methylacetophenone;

Trans-N-(6,6-dimethyl-2-hepten-4-ynyl)-N-methyl-[2-(m-tolyl)-2-propenyl]amine;

Trans-2-[N-(6,6-dimethyl-2-hepten-4-ynyl)-N-methylamino]-4'-methylacetophenone;

Trans-N-(6,6-dimethyl-2-hepten-4-ynyl)-N-methyl-[2-(p-tolyl)-2-propenyl]amine;

Trans-2-[N-(6,6-dimethyl-2-hepten-4-ynyl)-N-methylamino]-2'-fluoroacetophenone;

Trans-N-(6,6-dimethyl-2-hepten-4-ynyl)-N-methyl-[2-(2-fluorophenyl)-2-propenyl]amine;

Trans-2-[N-(6,6-dimethyl-2-hepten-4-ynyl)-N-methylamino]-3'-fluoroacetophenone;

Trans-N-(6,6-dimethyl-2-hepten-4-ynyl)-N-methyl-[2-(3-fluorophenyl)-2-propenyl]amine;

Trans-2-[N-(6,6-dimethyl-2-hepten-4-ynyl)-N-methylamino]-4'-fluoroacetophenone;

Trans-N-(6,6-dimethyl-2-hepten-4-ynyl)-N-methyl-[2-(4-fluorophenyl)-2-propenyl]amine;

Trans-2'-bromo-2-[N-(6,6-dimethyl-2-hepten-4-ynyl)-N-methylamino]acetophenone;

Trans-N-(6,6-dimethyl-2-hepten-4-ynyl)-N-methyl-[2-(2-bromophenyl)-2-propenyl]amine;

Trans-3'-bromo-2-[N-(6,6-dimethyl-2-hepten-4-ynyl)-N-methylamino]acetophenone;

Trans-N-(6,6-dimethyl-2-hepten-4-ynyl)-N-methyl-[2-(3-bromophenyl)-2-propenyl]amine;

Trans-4'-bromo-2-[N-(6,6-dimethyl-2-hepten-4-ynyl)-N-methylamino]acetophenone;

Trans-N-(6,6-dimethyl-2-hepten-4-ynyl)-N-methyl-[2-(4-bromophenyl)-2-propenyl]amine;

Trans-2'-chloro-2-[N-(6, 6-dimethyl-2-hepten-4-ynyl)-N-methylamino]acetophenone;

Trans-N-(6,6-dimethyl-2-hepten-4-ynyl)-N-methyl-[2-(2-chlorophenyl)-2-propenyl]amine;

Trans-4'-chloro-2-[N-(6,6-dimethyl-2-hepten-4-ynyl)-N-methylamino]acetophenone;

Trans-N-(6,6-dimethyl-2-hepten-4-ynyl)-N-methyl-[2-(4-chlorophenyl)-2-propenyl]amine;

Trans-2-[N-(6,6-dimethyl-2-hepten-4-ynyl)-N-methylamino]-2'-methoxyacetophenone;
Trans-N-(6,6-dimethyl-2-hepten-4-ynyl)-N-methyl-[2-(2-methoxyphenyl)-2-propenyl]amine;
Trans-2-[N-(6,6-dimethyl-2-hepten-4-ynyl)-N-methylamino]-3'-methoxyacetophenone;
Trans-N-(6,6-dimethyl-2-hepten-4-ynyl)-N-methyl-[2-(3-methoxyphenyl)-2-propenyl]amine;
Trans-2-[N-(6,6-dimethyl-2-hepten-4-ynyl)-N-methylamine]-2'-nitroacetophenone;
Trans-N-(6,6-dimethyl-2-hepten-4-ynyl)-N-methyl-[2-(2-nitrophenyl)-2-propenyl]amine;
Trans-2-[N-(6,6-dimethyl-2-hepten-4-ynyl)-N-methylamine]-3'-nitroacetophenone;
Trans-N-(6,6-dimethyl-2-hepten-4-ynyl)-N-methyl-[2-(3-nitrophenyl)-2-propenyl]amine;
Trans-2-[N-(6,6-dimethyl-2-hepten-4-ynyl)-N-methylamine]-4'-nitroacetophenone;
Trans-N-(6,6-dimethyl-2-hepten-4-ynyl)-N-methyl-[2-(4-nitrophenyl)-2-propenyl]amine;
Trans-3'-cyano-2-[N-(6,6-dimethyl-2-hepten-4-ynyl)-N-methylamino]acetophenone;
Trans-3-{1-[N-(6,6-dimethyl-2-hepten-4-ynyl)-N-methylamino]methyl}vinylbenzonitrile;
Trans-4'-cyano-2-[N-(6,6-dimethyl-2-hepten-4-ynyl)-N-methylamino)acetophenone;
Trans-4-{1-[N-(6,6-dimethyl-2-hepten-4-ynyl)-N-methylamino]methyl}vinylbenzonitrile;
Ethyl trans-4-{2-[N-(6,6-dimethyl-2-hepten-4-ynyl)-N-methylamino]acetyl}benzoate;
Ethyl trans-4-{1-[N-(6,6-dimethyl-2-hepten-4-ynyl)-N-methylamino]methyl}vinylbenzoate;
Trans-2',4'-dichloro-2-[N-(6,6-dimethyl-2-hepten-4-ynyl)-N-methylamino]acetophenone;
Trans-N-(6,6-dimethyl-2-hepten-4-ynyl)-N-methyl-[2-(2,4-dichlorophenyl)-2-propenyl]amine;
Trans-3',4'-dichloro-2-[N-(6,6-dimethyl-2-hepten-4-ynyl)-N-methylamino]acetophenone;
Trans-N-(6,6-dimethyl-2-hepten-4-ynyl)-N-methyl-[2-(3,4-dichlorophenyl)-2-propenyl]amine;
Trans-2',4'-dimethyl-2-[N-(6,6-dimethyl-2-hepten-4-ynyl)-N-methylamino]acetophenone;
Trans-N-(6,6-dimethyl-2-hepten-4-ynyl)-N-methyl-[2-(2,4-dimethylphenyl)-2-propenyl]amine;
Trans-3',4'-dimethyl-2-[N-( 6,6-dimethyl-2-hepten-4-ynyl)-N-methylamino]acetophenone;
Trans-N-(6,6-dimethyl-2-hepten-4-ynyl)-N-methyl-[2-(3,4-dimethylphenyl)-2-propenyl]amine;
Trans-3',4'-difluoro-2-[N-(6,6-dimethyl-2-hepten-4-ynyl)-N-methylamino]acetophenone;
Trans-N-(6,6-dimethyl-2-hepten-4-ynyl)-N-methyl-[2-(3,4-difluorophenyl)-2-propenyl]amine;
Trans-3',5'-difluoro-2-[N-(6,6-dimethyl-2-hepten-4-ynyl)-N-methylamino]acetophenone;
Trans-N-(6,6-dimethyl-2-hepten-4-ynyl)-N-methyl-[2-(3,5-difluorophenyl)-2-propenyl]amine;
Trans-4'-tert-butyl-2-[N-(6,6-dimethyl-2-hepten-4-ynyl)-N-methylamino]acetophenone;
Trans-N-(6,6-dimethyl-2-hepten-4-ynyl)-N-methyl-[2-(4-tert-butylphenyl)-2-propenyl]amine;
Trans-2-[N-(6,6-dimethyl-2-hepten-4-ynyl)-N-methylamino]-2'-hydroxyacetophenone;
Trans-4'-tert-butyldimethylsilyloxy-2-[N-(6,6-dimethyl-2-hepten-4-ynyl)-N-methylamino]acetophenone;
Trans-N-(6,6-dimethyl-2-hepten-4-ynyl)-N-methyl-[2-(4-tert-butyldimethylsilyloxyphenyl)-2-propenyl]amine;
Trans-N-(6,6-dimethyl-2-hepten-4-ynyl)-N-methyl-[2-(4-hydroxyphenyl)-2-propenyl]amine;
Trans-N-(6,6-dimethyl-2-hepten-4-ynyl)-N-methyl-[2-(2-aminophenyl)-2-propenyl]amine;
Trans-N-(6,6-dimethyl-2-hepten-4-ynyl)-N-methyl-[2-(3-aminophenyl)-2-propenyl]amine;
N-Cinnamyl-N-methyl-2-phenyl-2-propenylamine;
Trans-N-(6,6-dimethyl-2-hepten-4-ynyl)-N-ethyl-2-phenyl-2-propenylamine;
Trans-N-(6,6-dimethyl-2-hepten-4-ynyl)-N-isopropyl-2-phenyl-2-propenylamine; and
Trans-N-cyclopropyl-N-(6,6-dimethyl-2-hepten-4-ynyl)-2-phenyl-2-propenylamine.

5. An amine compound selected from formula (1) or salts thereof as claimed in claim 1, wherein an $R^1$ is a linear $C_{1-4}$ alkyl group, a branched $C_{1-4}$ alkyl group or a cyclic $C_{1-4}$ alkyl group, said $C_{1-4}$ alkyl group may be halogenated, $R^2$ is a group represented by the formula (a), (b) or (c); $R^8$, when $R^4$ is represented by the formula (i), is a linear $C_{1-4}$ alkyl group, a branched $C_{1-4}$ alkyl group, a cyclic $C_{1-4}$ alkyl group, a halogen atom, a linear $C_{1-4}$ alkoxy group, a branched $C_{1-4}$ alkoxy group, a cyclic $C_{1-4}$ alkoxy group, a nitro group, an amino group may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO—$, and $R^9$ represents a linear $C_{1-4}$ alkyl group, a branched $C_{1-4}$ alkyl group or a cyclic $C_{1-4}$ alkyl group, in which three of $R^9$ may be the same or different; m is an integer of 0 to 5.

6. An amine compound selected from formula (1) or their salts as claimed in claim 5, wherein $R^1$ is a methyl group, an ethyl group, an isopropyl group, a cyclopropyl group, a 2,2,2-trifluoroethy group, $R^5$ is a methyl group or a phenyl group, $R^3$ is a carbon atom to which an oxygen atom and two hydrogen atoms are added or a carbon atom to which two methyl groups are added, and $R^8$ is a fluorine atom, a chlorine atom, a bromine atom, a methyl group, a tert-butyl group, a methoxy group, an hydroxyl group, a tert-butyldimethylsilyloxy group, a nitro group, a cyano group, an amino group, a piperidino group, a carboxyl group, or an ethoxycarbonyl group.

7. An amine compound selected from formula (1) or salts thereof as claimed in claim 2, which is selected from the following compounds:
2-[N-(4-tert-butylbenzyl)-N-methylamino]acetophenone;
N-(4-tert-butylbenzyl)-N-methyl-2-phenyl-2-propenylamine;
4'-bromo-2-[N-(4-tert-butylbenzyl)-N-methylamino]acetophenone;
N-(4-tert-butylbenzyl)-N-methyl-[2-(4-bromophenyl-2-propenyl]amine;
2-[N-(4-tert-butylbenzyl)-N-methylamino]-4'-chloroacetophenone;
N-(4-tert-butylbenzyl)-N-methyl-[2-(4 -chlorophenyl-2-propenyl]amine;
2-[N-(4-tert-butylbenzyl)-N-methylamino]-4'-fluoroacetophenone;
N-(4-tert-butylbenzyl)-N-methyl-[2-(4-fluorophenyl-2-propenyl]amine;
2-[N-(4-tert-butylbenzyl)-N-methylamino]-2'-fluoroacetophenone;

N-(4-tert-butylbenzyl)-N-methyl-[2-(2-fluorophenyl-2-propenyl]amine;
2-(N-(4-tert-butylbenzyl)-N-methylamino]-2'-bromoacetophenone;
N-(4-tert-butylbenzyl)-N-methyl-[2-(2-bromophenyl-2-propenyl]amine;
2-[N-(4-tert-butylbenzyl)-N-methylamino]-3'-bromoacetophenone;
N-(4-tert-butylbenzyl)-N-methyl-[2-(3-bromophenyl-2-propenyl]amine;
2-[N-(4-tert-butylbenzyl)-N-methylamino]-3'-methylacetophenone;
N-(4-tert-butylbenzyl)-N-methyl-[2-(3-methyophenyl)-2-propenyl]amine;
2-[N-(4-tert-butylbenzyl)-N-methylamino]-2'-methylacetophenone;
N-(4-tert-butylbenzyl)-N-methyl-[2-(2 -methylphenyl)-2-propenyl]amine;
2-[N-(4-tert-butylbenzyl)-N-methylamino]-2'-methoxyacetophenone;
N-(4-tert-butylbenzyl)-N-methyl-[2-(2-methoxyphenyl)-2-propenyl]amine;
N-(4-tert-butylbenzyl)-N-methyl-[2-(2-nitrophenyl)-2-propenyl]amine;
N-(4-tert-butylbenzyl)-N-methyl-[2-(4-nitrophenyl )-2-propenyl]amine;
N-(4-tert-butylbenzyl)-N-methyl-[2-(3-nitrophenyl)-2-propenyl]amine;
N-(4-tert-butylbenzyl)-N-methyl-[2-(3-aminophenyl)-2-propenyl]amine;
N-(4-tert-butylbenzyl )-N-methyl-[2-(2-aminophenyl)-2-propenyl]amine;
2-[N-(4-tert-butylbenzyl)-N-methylamino]-3',4'-dimethylacetophenone;
N-(4-tert-butylbenzyl)-N-methyl-[2-(3,4-dimethyiphenyl)-2-propenyl]amine;
2[N-(4-tert-butylbenzyl)-N-methylamino]-2',4'-dimethylacetophenone;
N-(4-tert-butylbenzyl)-N-methyl-[2-(2,4-dimethyiphphenyl)-2-propenyl]amine;
4'-tert-butyl-2-[N-(4-tert-butylbenzyl)-N-methylamino]acetophenone;
N-(4-tert-butylbenzyl)-N-methyl-[2-(4-tert-butylphenyl)-2-propenyl]amine;
2-[N-(4-tert-butylbenzyl)-N-methylamino]-3'-cyanoacetophenone;
3-[1-{N-(4-tert-butylbenzyl)-N-methylamino}methyl]vinylbenzonitrile (Compound AD-051);
2-(N-(4-tert-butylbenzyl)-N-methylamino]-4'-tert-butyldimethylsilyloxyacetophenone;
N-(4-tert-butylbenzyl)-N-methyl-[2-(4-tert-butyldimethylsilyloxyphenyl)-2-propenyl]amine;
N-(4-tert-butylbenzyl)-N-methyl-[2-(4-hydroxyphenyl)-2-propenyl]amine;
2-[N-(4-tert-butylbenzyl)-N-methylamino]-2'-hydroxyacetophenone;
N-methyl-N-(1-naphthylmethyl)-2-phenyl-2-propenylamine;
N-methyl-N-(2-naphthylmethyl)-2-phenyl-2-propenylamine;
4'-tert-butyl-2-[N-methyl-N-(2-naphthylmethyl)amino] acetophenone;
N-methyl-N-(2-naphthylmethyl)-[2-(4-tert-butylphenyl)-2-propenyl]amine;
4'-tert-butyl-2-[N-methyl-N-(1 -naphthylmethyl)amino] acetophenone;
N-methyl-N-(1-naphthylmethyl)-[2-(4-tert-butylphenyl)-2-propenyl]amine;
2-[N-(4-tert-butylbenzyl)-N-methylamino]-2'-acetonaphthone;
N-(4-tert-butylbenzyl)-N-methyl-[2-(2-naphthyl)-2-propenyl]amine;
N-(4-tert-butylbenzyl)-N-(2,2,2-trifluoroethyl)-2-phenyl-2-propenylamine;
2-[N-(4-tert-butylbenzyl)-N-methylamino]-3',5'-difluoroacetophenone;
N-(4-tert-butylbenzyl)-N-methyl-[2-(3',5'-difluorophenyl)-2-propenyl]amine;
2-[N-(4-tert-butylbenzyl)-N-methylamino]-3',4'-difluoroacetophenone;
N-(4-tert-butylbenzyl)-N-methyl-[2-(3,4-difluorophenyl)-2-propenyl]amine;
N-[4-(1-methyl-1-phenylethyl)benzyl)]-N-methyl-2-phenyl-2-propenylamine;
2-[N-(4-tert-butylbenzyl)-N-methylamino]-4'-methylacetophenone;
N-(4-tert-butylbenzyl )-N-methyl-[2-(4-methylphenyl)-2-propenyl]amine;
2-[N-(4-tert-butylbenzyl)-N-methylamino]-3'-fluoroacetophenone;
N-(4-tert-butylbenzyl)-N-methyl-2-(3-fluorophenyl)-2-propenyl]amine;
2-[N-(4-tert-butylbenzyl)-N-methylamino]-2',4'-dichloroacetophenone;
N-(4-tert-butylbenzyl)-N-methyl-[2-(2,4-dichlorophenyl)-2-propenyl]amine;
N-(4-tert-butylbenzyl)-N-methyl-3-methyl-2-phenyl-2-butenylamine;
2-[N-(4-tert-butylbenzyl)-N-methylamino]-2'-chloroacetophenone;
N-(4-tert-butylbenzyl)-N-methyl-[2-(2-chlorophenyl)-2-propenyl]amine;
2-[N-(4-tert-butylbenzyl)-N-methylamino]-3',4'-dichloroacetophenone;
N-(4-tert-butylbenzyl)-N-methyl-[2-(3,4-dichiorophenyl)-2-propenyl]amine;
2-[N-(4-tert-butylbenzyl)-N-methylamino]-3'-methoxyacetophenone;
N-(4-tert-butylbenzyl)-N-methyl-[2-(3-methoxyphenyl)-2-propenyl]amine;
2-[N-(4-tert-butylbenzyl)-N-methylamino]-4'-piperidinoacetophenone;
N-(4-tert-butylbenzyl)-N-methyl-[2-(4-piperidinophenyl)-2-propenyl]amine;
2-[N-(4-tert-butylbenzyl)-N-methylamino]-4'-cyanoacetophenone;
4-[1-{N-(4-tert-butylbenzyl)-N-methylamino}methyl]vinylbenzonitrile;
Ethyl 4-[2-{N-(4-tert-butylbenzyl)-N-methylamino}acetyl]benzoate;
Ethyl 4-[1-{N-(4-tert-butylbenzyl)-N-methylamino}methyl]vinylbenzoate;
4-[1-{N-(4-tert-butylbenzyl)-N-methylamino}methyl]vinylbenzoic acid;

N-(4-tert-butylbenzyl)-N-ethyl-2-phenyl-2-propenylamine;

N-(4-tert-butylbenzyl)-N-isopropyl-2-phenyl-2-propenylamine; and

N-(4-tert-butylbenzyl)-N-cyclopropyl-2-phenyl-2-propenylamine.

8. An amine compound selected from formula (1) or salts thereof as claimed in claim 1, wherein the salt is a hydrochloride.

9. A method for producing an amine compound represented by formula (1) or salts thereof

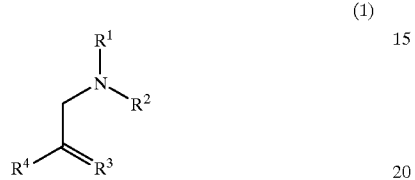

(1)

in the formula (1), $R^1$, $R^2$, $R^3$, and $R^4$ represent the same meanings as those in formulae (2) and (3) below comprising condensing a compound represented by general formula (2)

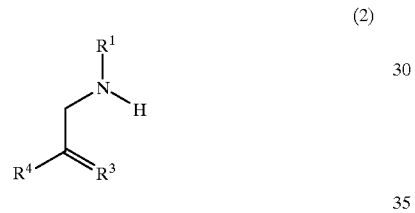

(2)

in the formula (2), $R^1$ represents a linear $C_{1-5}$ alkyl group, a branched $C_{1-5}$ alkyl group, or a cyclic $C_{1-5}$ alkyl group, said $C_{1-5}$ alkyl group may be halogenated; $R^3$ represents an oxygen atom or a group represented by the formula (f) below;

(f)

$R^6$ and $R^7$ independently represent a hydrogen atom, a linear $C_{1-4}$ alkyl group, a branched $C_{1-4}$ alkyl group or a cyclic $C_{1-4}$ alkyl group; $R^4$ represents a group represented by the formula (g), (h), or (i),

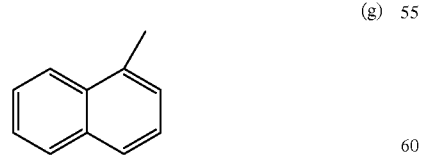

(g)

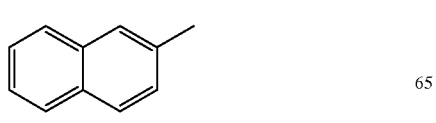

(h)

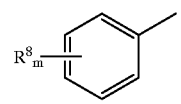

(i)

in the formula (i), $R^8$ is a substituent group which substitutes a hydrogen atom in the phenyl group in the formula and represents a linear $C_{1-7}$ alkyl group, a branched $C_{1-7}$ alkyl group, a cyclic $C_{1-7}$ alkyl group, a halogen atom, a linear $C_{1-4}$ alkoxy group, a branched $C_{1-4}$ alkoxy group, a cyclic $C_{1-4}$ alkoxy group, a nitro group, an amino group which may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO-$, $R^9$ represents a linear $C_{1-4}$ alkyl group, a branched $C_{1-4}$ alkyl group or a cyclic $C_{1-4}$ alkyl group, in which three of $R^9$ may be the same or different; and m of $R^8$ may be the same or different; m is an integer of 0 to 5, with a compound represented by general formula (3)

(3)

in the formula (3), $R^2$ represents a group represented by the formula (a), (b), (c), (d), or (e)

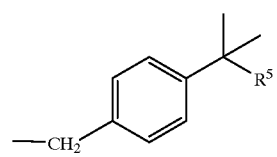

(a)

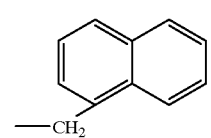

(b)

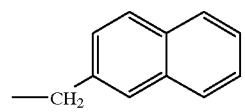

(c)

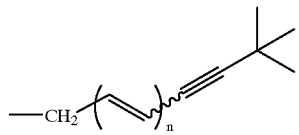

(d)

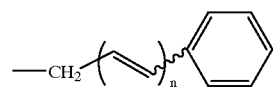

(e)

("∿∿∿" indicates that the arrangement of double bond may be either cis or trans)

(provided that $R^5$ in the formula (a) is a linear $C_{1-4}$ alkyl group or a phenyl group and n in the formula (d) or (e) is an integer of 1 to 3); and X represents a halogen atom).

10. A method for producing an amine compound represented by formula (1) or salt thereof

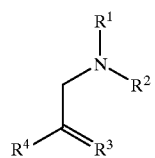
(1)

in the formula (1), $R^1$, $R^2$ $R^3$, and $R^4$ represent the same meanings as those in formulae (4) and (5) below comprising condensing a compound represented by general formula (4)

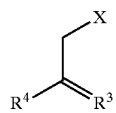
(4)

in the formula (4), $R^3$ represents an oxygen atom or a group represented by the formula (f) below;

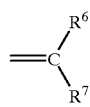
(f)

$R^6$ and $R^7$ independently represent a hydrogen atom, a linear $C_{1-4}$ alkyl group, a branched $C_{1-4}$ alkyl group or a cyclic $C_{1-4}$ alkyl group, $R^4$ is a group represented by the formula (g), (h), or (i),

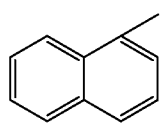
(g)

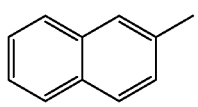
(h)

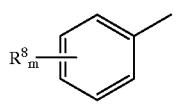
(i)

in the formula (i), $R^8$ is a substituent group which substitutes a hydrogen atom in the phenyl group in the formula (i) and represents a linear $C_{1-7}$ alkyl group, a branched $C_{1-7}$ alkyl group, a cyclic $C_{1-7}$ alkyl group, a halogen atom, a linear $C_{1-4}$ alkoxy group, a branched $C_{1-4}$ alkoxy group, a cyclic $C_{1-4}$ alkoxy group, a nitro group, an amino group may be substituted, a cyano group, a carboxyl group, a linear $C_{2-5}$ alkoxycarbonyl group, a branched $C_{2-5}$ alkoxycarbonyl group, a cyclic $C_{2-5}$ alkoxycarbonyl group, a hydroxyl group, or a group represented by $R^9{}_3SiO$—, $R^9$ represents a linear $C_{1-4}$ alkyl group, a branched $C_{1-4}$ alkyl group or a cyclic $C_{1-4}$ alkyl group, in which three of $R^9$ may be the same or different; m of $R^8$ may be the same or different; m is an integer of 0 to 5; and X represents a halogen atom, with a compound represented by general formula (5)

(5)

in the formula (5), $R^1$ represents a linear $C_{1-5}$ alkyl group, a branched $C_{1-5}$ alkyl group, or a cyclic $C_{1-5}$ alkyl group, said $C_{1-5}$ alkyl group may be halogenated; $R^2$ represents a group represented by the formula (a), (b), (c), (d), or (e)

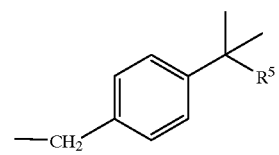
(a)

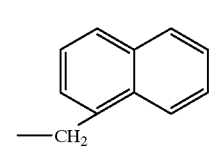
(b)

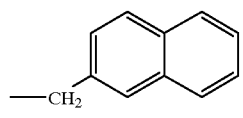
(c)

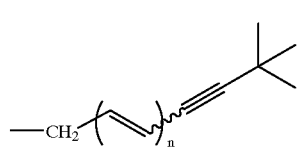
(d)

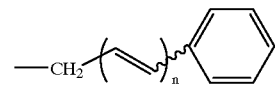
(e)

("⁓⁓⁓" indicates that the arrangement of double bond may be either cis or trans)

(provided that $R^5$ in the formula (a) is a linear $C_{1-4}$ alkyl group or a phenyl group and n in the formula (d) or (e) is an integer of 1 to 3).

11. An antimycotic composition comprising an antimycotic effective amount of at least one compound or salt thereof selected from formula 1 of claim 1 together with inert carrier.

12. The composition of claim 11 wherein the inner carrier is a pharmaceutically acceptable inner carrier.

13. A method of preventing or inhibiting the growth of fungi comprising contacting the subject or object in need thereof with an antimycotic effective amount of at least one compound or salt thereof selected from formula 1 in claim 1.

* * * * *

UNITED STATES PATENT AND TRADEMARK OFFICE
CERTIFICATE OF CORRECTION

PATENT NO. : 6,329,399 B1
DATED : December 11, 2001
INVENTOR(S) : Itoh et al.

It is certified that error appears in the above-identified patent and that said Letters Patent is hereby corrected as shown below:

Column 7,
Line 66, after "preferably" please add -- an oxygen atom, --.
Line 67, after "to which" please delete "an oxygen atom and".

Column 11,
Line 48, after "preferably" please delete -- an oxygen atom, --.
Line 49, after "to which" please delete "an oxygen atom and".

Column 16,
Line 22, after "so forth" please delete "," and insert -- . --.

Column 17,
Line 66, after "produced" please delete "by" and insert -- from --.

Column 20,
Line 3, after "poured" please delete "onto" and insert -- into --.
Line 18, please change "butydilmethylsilyloxyacetophenone"
to -- butyldilmethylsilyloxyacetophenone --.

Column 25,
Line 35, after "N-methyl-4-" please change "(1-1-methyl-phenylethyl)" to
-- (1-methyl-phenylethyl) --.
Line 61, after "(yield: 64.6%)" please add -- of --.

Column 26,
Line 6, after "hydrochloride" please delete "are also described" and
insert -- of the compounds --.
Line 7, after "2" please insert -- are also described --.
Line 19-20, after "Table 1 represents" please change "(6,6-dimethyl-2-hepten-4-ynyl
group" to -- 6, 6-dimethyl-2-hepten-4-ynyl group --.

Column 36,
Line 37, after "Compound" please change "PR-1531" to -- PR-1468 --.

Column 52,
Line 3, after "Yield:" please change "008 g" to -- 0.08g --.

Line 6, after 3.65, please change "(ブロード s, 2H)" to -- (broad s, 2H) --.

UNITED STATES PATENT AND TRADEMARK OFFICE
CERTIFICATE OF CORRECTION

PATENT NO. : 6,329,399 B1
DATED : December 11, 2001
INVENTOR(S) : Itoh et al.

It is certified that error appears in the above-identified patent and that said Letters Patent is hereby corrected as shown below:

<u>Column 52, (cont'd),</u>
Line 19, please change "(ブロ－ド s, 2H)" to -- (broad s, 2H) --.

<u>Column 55,</u>
Line 3, after "Compound" please change "PR-1931" to -- PR-1930 --.

<u>Column 65,</u>
Line 40, after "Example 36" please delete "in".

<u>Column 78,</u>
Line 9, after "$R^3$ is" please insert -- an oxygen atom or --.
Line 10, after "to which" please delete "an oxygen atom or".

<u>Column 80,</u>
Line 40, after "$R^3$ is" please insert -- an oxygen atom, --.
Line 40, after "to which" please delete "an oxygen atom and".

Signed and Sealed this

Thirty-first Day of May, 2005

JON W. DUDAS
*Director of the United States Patent and Trademark Office*